(12) United States Patent
Kumar-Singh

(10) Patent No.: US 11,713,337 B2
(45) Date of Patent: Aug. 1, 2023

(54) PEPTIDE, COMPOSITIONS AND METHOD FOR DELIVERY OF AGENTS INTO CELLS AND TISSUES

(71) Applicant: Trustees of Tufts College, Medford, MA (US)

(72) Inventor: Rajendra Kumar-Singh, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 17/646,496

(22) Filed: Dec. 30, 2021

(65) Prior Publication Data

US 2022/0204562 A1  Jun. 30, 2022

Related U.S. Application Data

(63) Continuation of application No. PCT/US2020/040720, filed on Jul. 2, 2020.

(60) Provisional application No. 62/869,831, filed on Jul. 2, 2019.

(51) Int. Cl.
| | |
|---|---|
| *C07K 7/08* | (2006.01) |
| *A61P 27/02* | (2006.01) |
| *A61K 47/42* | (2017.01) |
| *C07K 7/06* | (2006.01) |
| *C07K 14/47* | (2006.01) |
| *C07K 14/49* | (2006.01) |
| *C12N 15/86* | (2006.01) |
| *A61K 38/00* | (2006.01) |

(52) U.S. Cl.
CPC ............. *C07K 7/08* (2013.01); *A61K 47/42* (2013.01); *A61P 27/02* (2018.01); *C07K 7/06* (2013.01); *C07K 14/47* (2013.01); *C07K 14/49* (2013.01); *C12N 15/86* (2013.01); *A61K 38/00* (2013.01); *C12N 2750/14143* (2013.01)

(58) Field of Classification Search
None
See application file for complete search history.

(56) References Cited

U.S. PATENT DOCUMENTS

| | | | | |
|---|---|---|---|---|
| 5,211,657 A | * | 5/1993 | Yamada | A61L 27/227 514/17.7 |
| 6,921,663 B2 | * | 7/2005 | Mizuguchi | C12N 15/86 435/456 |
| 7,396,664 B2 | | 7/2008 | Daly | |
| 8,778,886 B2 | | 7/2014 | Kumar-Singh | |
| 2007/0238684 A1 | * | 10/2007 | Hallek | C07K 14/005 435/325 |
| 2010/0322862 A1 | * | 12/2010 | Ruoslahti | A61P 35/00 424/9.1 |
| 2013/0158103 A1 | * | 6/2013 | Mohan | A61K 38/1709 514/44 R |
| 2016/0302425 A1 | | 10/2016 | DiDonato | |
| 2017/0349628 A1 | | 12/2017 | Suh | |
| 2018/0055958 A1 | | 3/2018 | Somamoto | |

OTHER PUBLICATIONS

Anderson, C., et al. An alkali-burn injury model of corneal neovascularization in the mouse. J Vis Exp, 2014(86).
Arroyo, J.G., et al., 2005. Photoreceptor apoptosis in human retinal detachment. Am J Ophthalmol 139, 605-610.
Bechara, C., et al, 2013. Cell-penetrating peptides: 20 years later, where do we stand? FEBS Lett 587, 1693-1702.
Bennett, J., 2017. Taking Stock of Retinal Gene Therapy: Looking Back and Moving Forward. Mol Ther 25, 1076-1094.
Binder, C., et al. 2011. Nuclear targeted delivery of macromolecules to retina and cornea. J Gene Med 13, 158-170.
Birke, M.T., et al., 2014. AAV-mediated expression of human PRELP inhibits complement activation, choroidal neovascularizatio11 and deposition of membrane attack complex in mice. Gene Ther 21, 507-513.
Boyd, R.F., et al., 2016. Reduced retinal transduction and enhanced transgene-directed immunogenicity with intravitreal delivery of rAAV following posterior vitrectomy in dogs. Gene Ther 23, 548-556.
Bredrup, C., et al., Congenital stromal dystrophy of the cornea caused by a mutation in the decorin gene. Invest Ophthalmol Vis Sci, 2005. 46(2): p. 420-6.
Bron, A.J., The architecture of the corneal stroma. Br J Ophthalmol, 2001. 85(4): p. 379-81.
Cashman, S.M., et al. 2015. Adenovirus-mediated delivery of Factor H attenuates complement C3 induced pathology in the murine retina: a potential gene therapy for age-related macular degeneration. J Gene Med 17, 229-243.
Chan, F., et al. "Knock-in human rhodopsin-GFP fusions as mouse models for human disease and targets for gene therapy." Proceedings of the National Academy of Sciences 101.24 (2004): 9109-9114.
Chen, W.S., et al., Galectin-3 Inhibition by a Small-Molecule Inhibitor Reduces Both Pathological Corneal Neovascularization and Fibrosis. Invest Ophthalmol Vis Sci, 2017. 58(1): p. 9-20.
Chen, Y., et al., MK2 inhibitor reduces alkali burn-induced inflammation in rat cornea. Sci Rep, 2016. 6: p. 28145.

(Continued)

*Primary Examiner* — James D Schultz
*Assistant Examiner* — Kimberly A Aron
(74) *Attorney, Agent, or Firm* — Quarles & Brady

(57) ABSTRACT

Cell penetrating peptides that target many cells types including cells of the retina and cornea with high efficiency are provided herein. These peptides can be used to deliver cargo molecules across a plasma membrane, without the need for chemical conjugation. Compositions and viral vectors comprising these cell-penetrating peptides are also provided. Methods of using the peptides, compositions and viruses to deliver various agents to target cells and tissues are also provided.

25 Claims, 50 Drawing Sheets
(44 of 50 Drawing Sheet(s) Filed in Color)
Specification includes a Sequence Listing.

(56) References Cited

OTHER PUBLICATIONS

Chowdhury, S., et al., Pirfenidone nanoparticles improve corneal wound healing and prevent scarring following alkali burn. PLoS One, 2013. 8(8): p. e70528.
Christoforidis, J.B., et al., 2017. Systemic Biodistribution and Intravitreal Pharmacokinetic Properties of Bevacizumab, Ranibizumab, and Aflibercept in a Nonhuman Primate Model. Invest Ophthalmol Vis Sci 58, 5636-5645.
Clark, S.J., et al., 2011. Mapping the differential distribution of glycosaminoglycans in the adult human retina, choroid, and sclera. Invest Ophthalmol Vis Sci 52, 6511-6521.
Cottet, S., et al., 2009. Mechanisms of apoptosis in retinitis pigmentosa. Curr Mol Med 9, 375-383.
Dalkara, D., et al., 2013. In vivo-directed evolution of a new adeno-associated virus for therapeutic outer retinal gene delivery from the vitreous. Sci Transl Med 5, 189ra176.
De Coupade, C., et al., 2005. Novel human-derived cell-penetrating peptides for specific subcellular delivery of therapeutic biomolecules. Biochem J 390, 407-418.
Donnini, S., et al., 2009. Prevention of ischemic brain injury by treatment with the membrane penetrating apoptosis inhibitor, TAT-BH4. Cell Cycle 8, 1271-1278.
Du, S., et al., Decorin inhibits angiogenic potential of choroid-retinal endothelial cells by downregulating hypoxia-induced Met, Rac1, HIF-1alpha and VEGF expression in cocultured retinal pigment epithelial cells. Exp Eye Res, 2013, 116: p. 151-60.
Fish, R. et al. Management of ocular thermal and chemical injuries, including amniotic membrane therapy. Curr Opin Ophthalmol, 2010. 21(4 ): p. 317-21.
Glasgow, B.J., et al., Tear lipocalins: potential lipid scavengers for the corneal surface. Invest Ophthalmol Vis Sci, 1999. 40(13): p. 3100-7.
Grant, D.S., et al., Decorin suppresses tumor cell-mediated angiogenesis. Oncogene, 2002. 21(31): p. 4765-77.
Griffith, G.L., et al., Treatment of corneal chemical alkali burns with a cross/inked thiolated hyaluronic acid film. Burns, 2018. 44(5): p. 1179-1186.
Gubbiotti, M.A., et al. 2016. Decorin interacting network: A comprehensive analysis of decorin-binding partners and their versatile functions. Matrix Biol 55, 7-21.
Guidotti, G., et al. 2017. Cell-Penetrating Peptides: From Basic Research to Clinics. Trends Pharmacol Sci 38, 406-424.
Hollander, B.A., et al. 1999. Linkage of a nucleolin-related protein and casein kinase II with the detergent-stable photoreceptor cytoskeleton. Cell Motil Cytoskeleton 43, 114-127.
Hotchkiss, R.S., et al., 2006. TAT-BH4 and TAT-Bcl-xl peptides protect against sepsis-induced lymphocyte apoptosis in vivo. J Immunol 176, 5471-5477.
Hovanessian, A.G., et al., 2010. Surface expressed nucleolin is constantly induced in tumor cells to mediate calcium-dependent ligand internalization. PLoS One 5, e15787.
International Searching Authority. International Search Report and Written Opinion for application PCT/US2020/040720, dated Feb. 17, 2021. 9 pages.
Iozzo, R.V., et al., Decorin antagonizes IGF receptor I (IGF-IR) function by interfering with IGF-IR activity and attenuating downstream signaling. J Biol Chem, 2011. 286(40): p. 34712-21.
Jarvelainen, H., et al., 2015. Pivotal role for decorin in angiogenesis. Matrix Biol 43, 15-26.
Johnson, L.N., et al. 2008. Cell-penetrating peptide for enhanced delivery of nucleic acids and drugs to ocular tissues including retina and cornea. Mol Ther 16, 107-114.
Johnson, L.N., et al. 2010. Cell penetrating peptide POD mediates delivery of recombinant proteins to retina, cornea and skin. Vision Res 50, 686-697.
Jones, S. W., et al. 2005. Characterisation of cell-penetrating peptide-mediated peptide delivery. British journal of pharmacology, 145(8), 1093-1102.

Khabou, H. et al. 2016. Insight into the mechanisms of enhanced retinal transduction by the engineered AAV2 capsid variant-7m8. Biotechnol Bioeng 113, 2712-2724.
Kibbey, M.C., et al. 1995. A 110-kD nuclear shuttling protein, nucleolin, binds to the neurite-promoting IKVAV site of laminin-1. J Neurosci Res 42, 314-322.
Kotterman, M.A., et al. 2015. Antibody neutralization poses a barrier to intravitreal adeno-associated viral vector gene delivery to non-human primates. Gene Ther 22, 116-126.
Koutsioumpa, M., et al. 2014. Cell surface nucleolin as a target for anti-cancer therapies. Recent Pat Anticancer Drug Discov 9, 137-152.
Krilleke, D., et al. 2009. The heparin-binding domain confers diverse functions of VEGF-A in development and disease: a structure-function study. Biochem Soc Trans 37, 1201-1206.
Kumar, B., et al. Complement-Mediated Activation of the NLRP3 Inflammasome and Its Inhibition by AAV-Mediated Delivery of CD59 in a Model of Uveitis. Mol Ther, 2018. 26(6): p. 1568-1580.
Leaderer, D., et al. 2015. Topical application of a G-Quartet aptamer targeting nucleolin attenuates choroidal neovascularization in a model of age-related macular degeneration. Exp Eye Res 140, 171-178.
Leaderer, D., et al. 2016. G-quartet oligonucleotide mediated delivery of proteins into photoreceptors and retinal pigment epithelium via intravitreal injection. Exp Eye Res 145, 380-392.
Leonard, K.C., et al. 2007. XIAP protection of photoreceptors in animal models of retinitis pigmentosa. PLoS One 2, e314.
Libby, R.T., et al. 2000. Laminin expression in adult and developing retinae: evidence of two novel CNS laminins. J Neurosci 20, 6517-6528.
Maidana, D.E., et al., A Novel ImageJ Macro for Automated Cell Death Quantitation in the Retina. Invest Ophthalmol Vis Sci, 2015. 56(11): p. 6701-8.
Martin, D.F., et al., 2012. Ranibizumab and bevacizumab for treatment of neovascular age-related macular degeneration: two-year results. Ophthalmology 119, 1388-1398.
Michalska-Malecka, K., et al. 2016. Effects of intravitreal ranibizumab on the untreated eye and systemic gene expression profile in age-related macular degeneration. Clin Interv Aging 11, 357-365.
Mohan, R.R., et al., Decorin biology, expression, function and therapy in the cornea. Curr Mol Med, 2011. 11(2): p. 110-28.
Mohan, R.R., et al., Targeted decorin gene therapy delivered with adeno-associated virus effectively retards corneal neovascularization in vivo. PLoS One, 2011. 6(10): p. e26432.
Mongelard, F., et al. 2007. Nucleolin: a multiFACeTed protein. Trends Cell Biol 17, 80-86.
Ogura, S., et al., Sustained inflammation after pericyte depletion induces irreversible blood-retina barrier breakdown. JCI Insight, 2017. 2(3): p. e90905.
Paranthan, R.R., et al., A robust model for simultaneously inducing corneal neovascularization and retinal gliosis in the mouse eye. Mol Vis, 2011. 17: p. 1901-8.
Paschalis, E.I., et al., The Role of Microglia and Peripheral Monocytes in Retinal Damage after Corneal Chemical Injury. Am J Pathol , 2018. 188(7): p. 1580-1596.
Petrin, D., et al. 2003. Structural and functional protection of photoreceptors from MNU-induced retinal degeneration by the X-linked inhibitor of apoptosis. Invest Ophthalmol Vis Sci 44, 2757-2763.
Phulke, S., et al. 2017. Steroid-induced Glaucoma: An Avoidable Irreversible Blindness. J Curr Glaucoma Pract 11, 67-72.
Reichel, F.F., et al. 2017. AAV8 Can Induce Innate and Adaptive Immune Response in the Primate Eye. Mol Ther 25, 2648-2660.
Rong, Y.P., et al. 2009. The BH4 domain of Bcl-2 inhibits ER calcium release and apoptosis by binding the regulatory and coupling domain of the IP3 receptor. Proc Natl Acad Sci U S A 106, 14397-14402.
Shin, Y.J., et al., Chemical injury-induced corneal opacity and neovascularization reduced by rapamycin via TGF-beta1/ERK pathways regulation. Invest Ophthalmol Vis Sci, 2013. 54(7): p. 4452-8.
Strober, W., et al. The immunology of mucosal models of inflammation. Annu Rev Immunol, 2002. 20: p. 495-549.

(56) References Cited

OTHER PUBLICATIONS

Talreja, D., et al. 2018. G-quartet oligonucleotide mediated delivery of functional X-linked inhibitor of apoptosis protein into retinal cells following intravitreal injection. Exp Eye Res 175, 20-31.
Tashiro, K., et al. 1989. A synthetic peptide containing the IKVAV sequence from the A chain of laminin mediates cell attachment, migration, and neurite outgrowth. J Biol Chem 264, 16174-16182.
Tzeng, H.E., et al., Interleukin-6 induces vascular endothelial growth factor expression and promotes angiogenesis through apoptosis signal-regulating kinase 1 in human osteosarcoma. Biochem Pharmacol, 2013. 85(4): p. 531-40.
Wizeman, J.W. et al. Expression of peptidyiarginine deiminase 4 in an alkali injury model of retinal gliosis. Biochem Biophys Res Commun, 2017. 487(1): p. 134-139.
Zhang, G., et al. 2018. The role of Dexamethasone in clinical pharmaceutical treatment for patients with cataract surgery. Exp Ther Med 15, 2177-2181.
Zhou, C., et al., Sustained Subconjunctival Delivery of Infliximab Protects the Cornea and Retina Following Alkali Burn to the Eye. Invest Ophthalmol Vis Sci, 2017. 58(1): p. 96-105.

\* cited by examiner

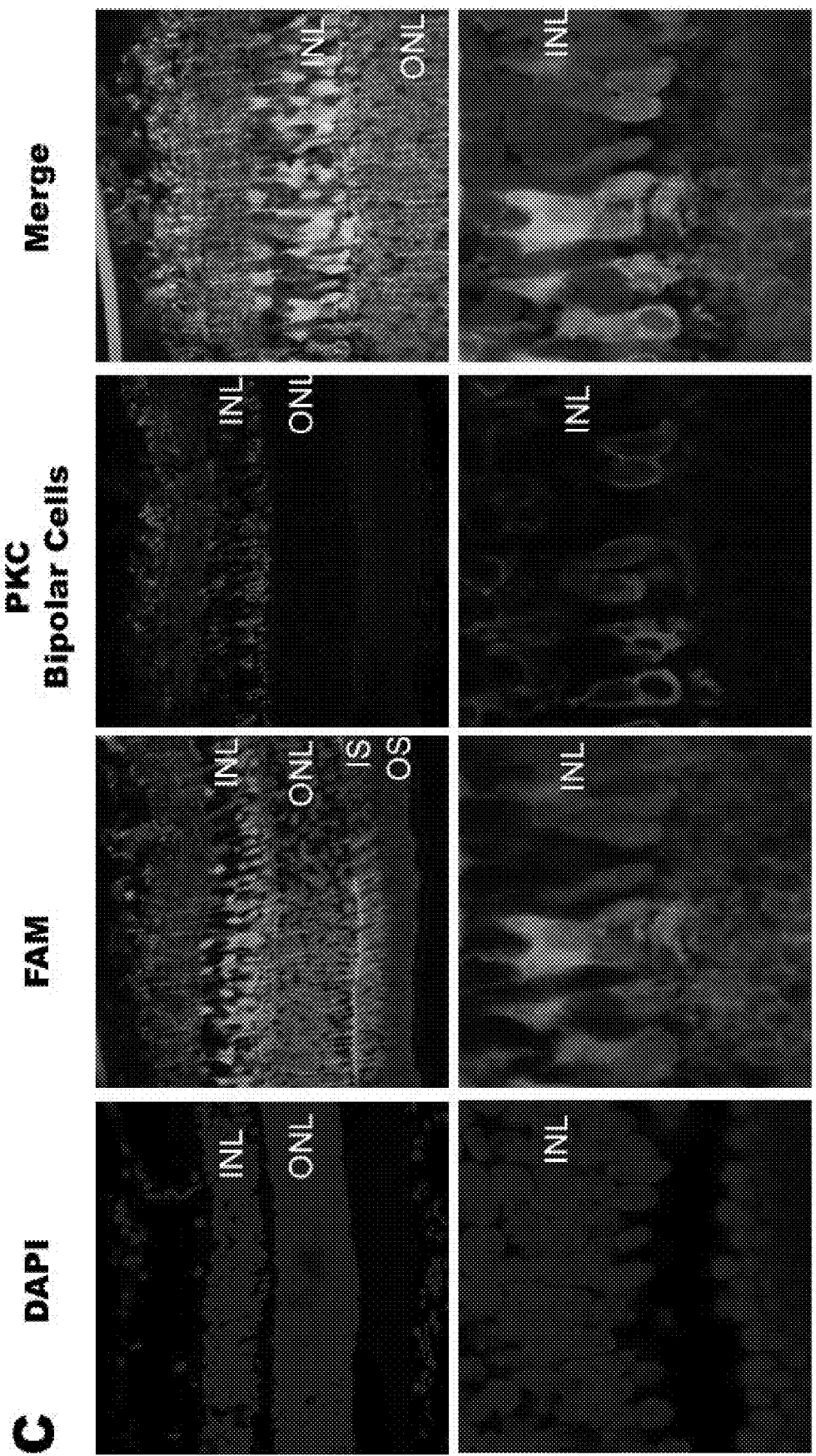

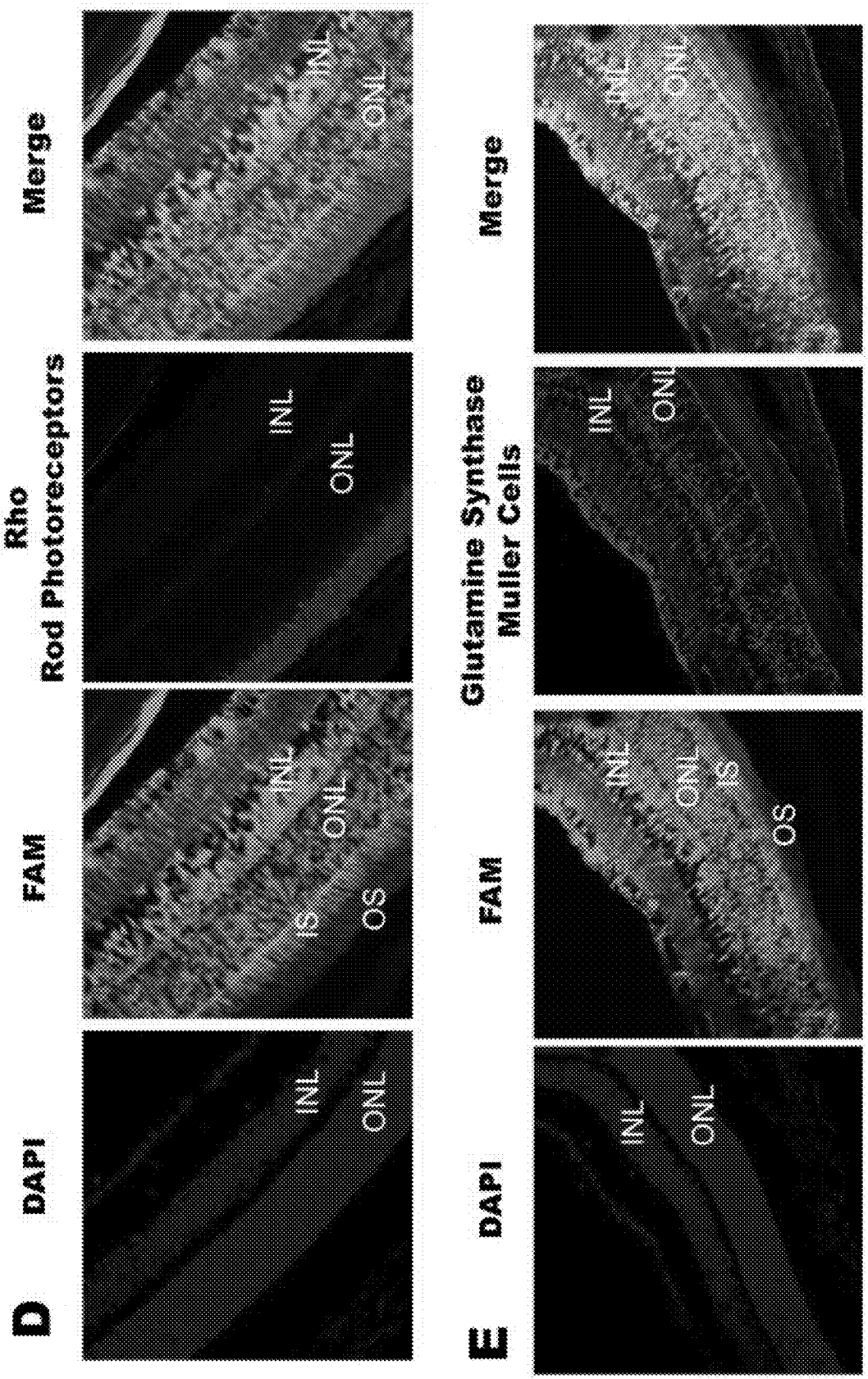

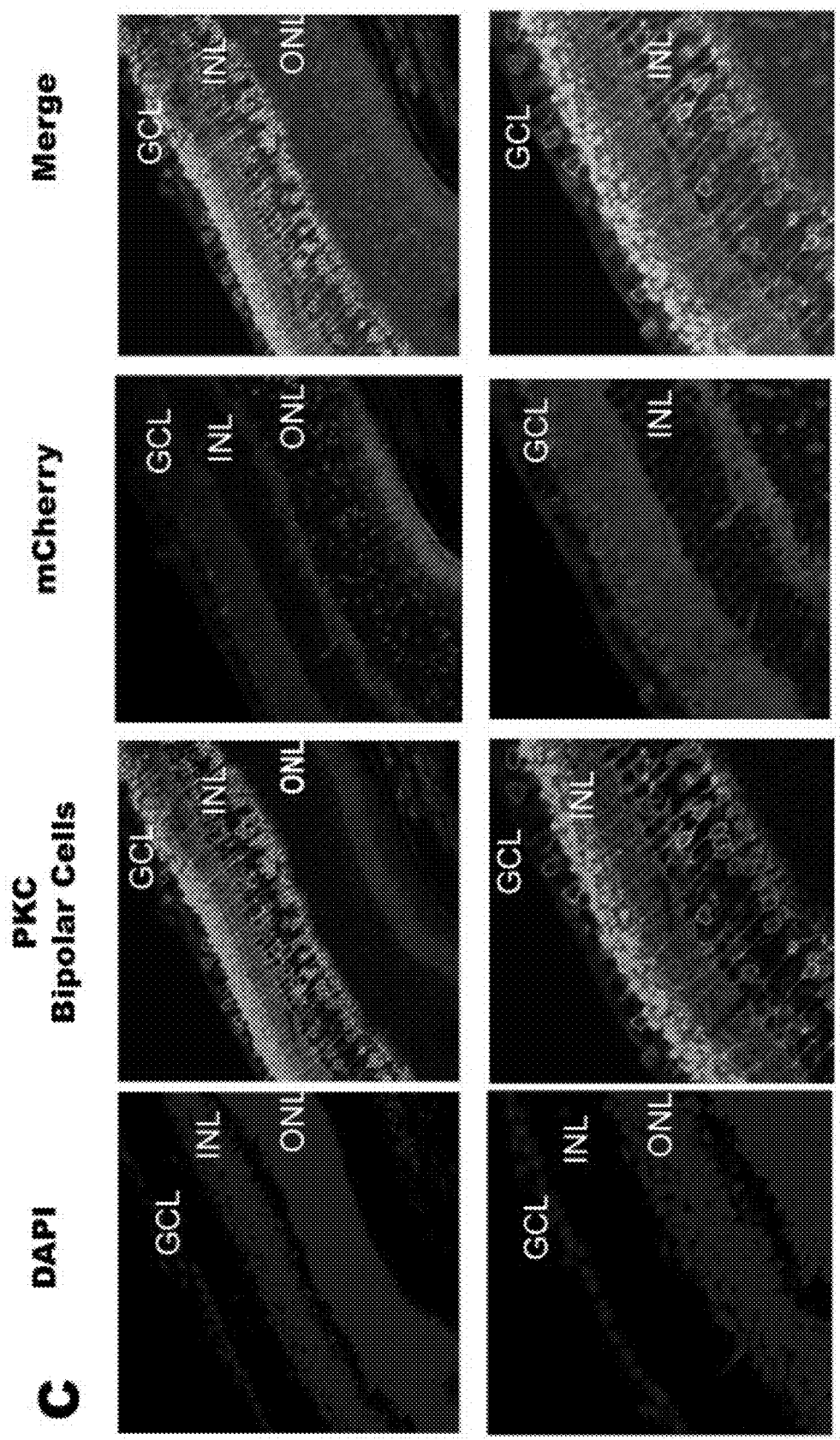

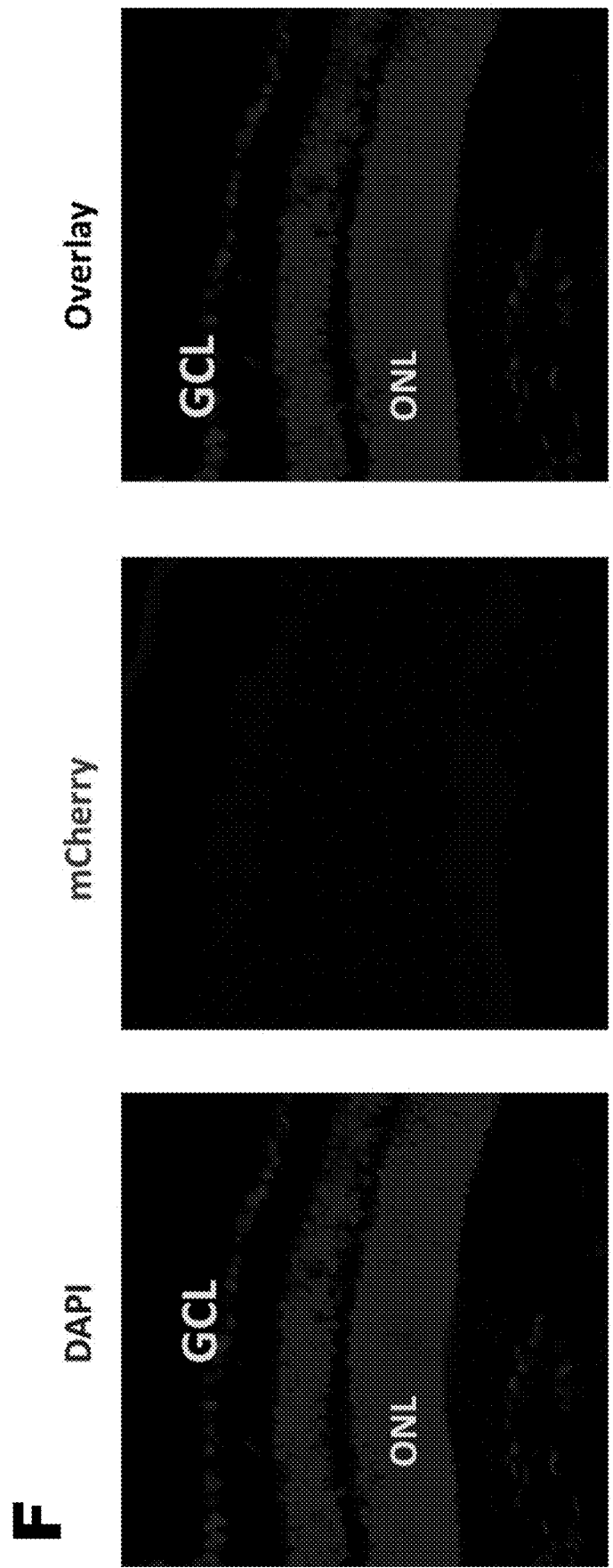

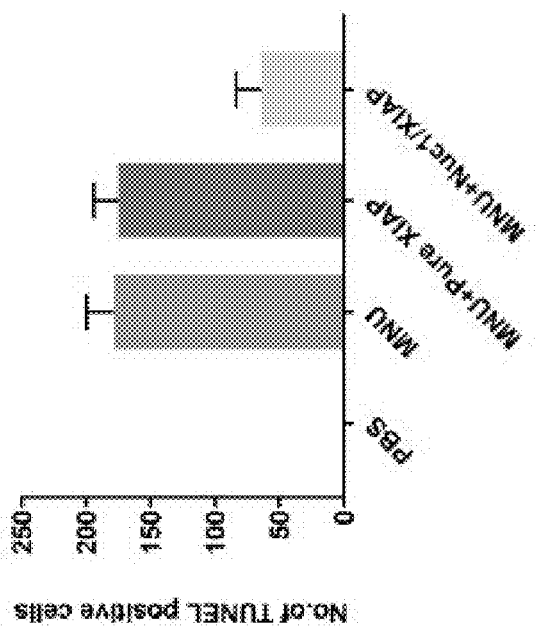
Fig. 3
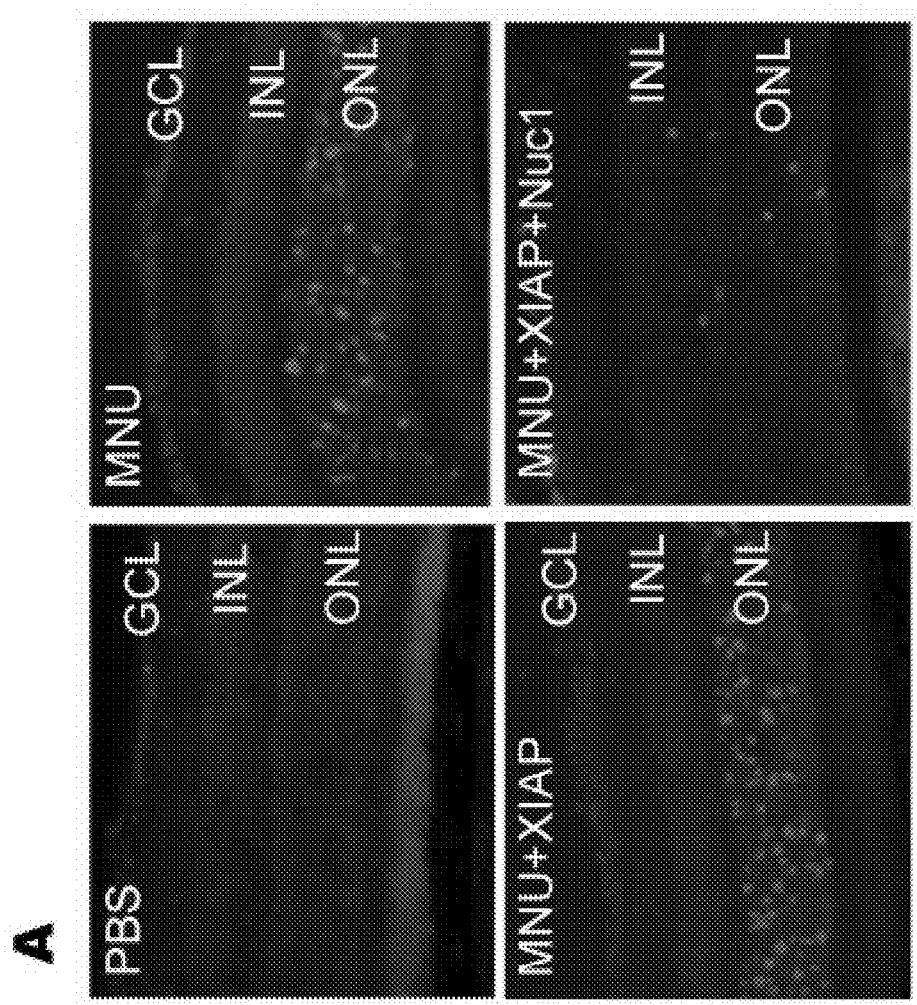

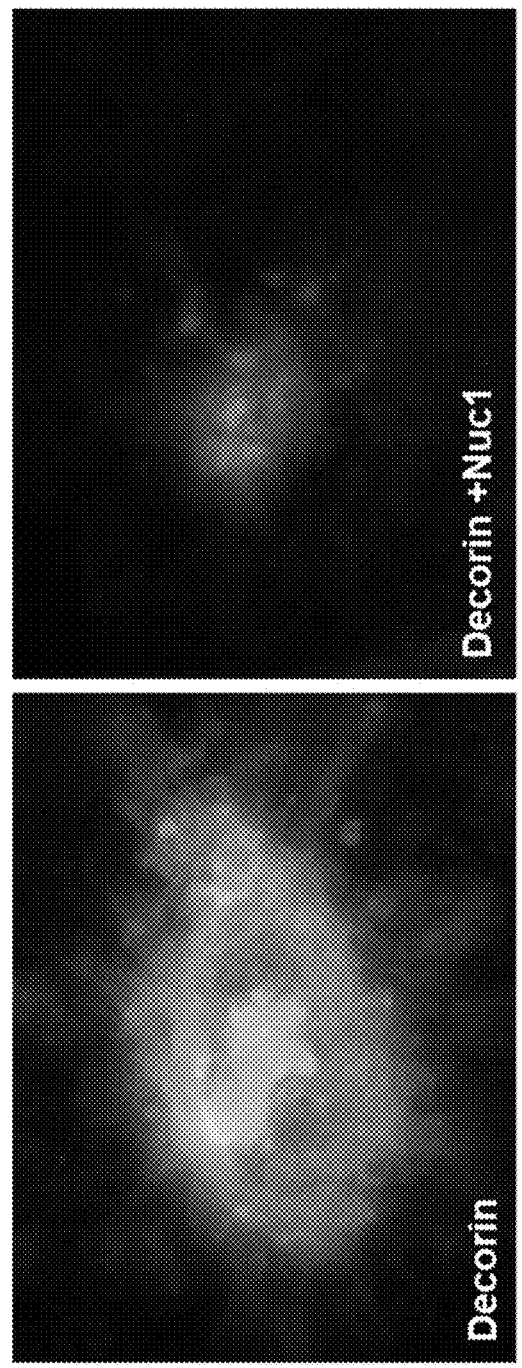

Quantification of GFP transcripts in the retinal samples after the intravitreal injections of GFP expressing AAV9 variants; AAV9GFP= AAVCAGGFP; IKVGFP=AAV9IKVGFP;

PEPTIDE, COMPOSITIONS AND METHOD FOR DELIVERY OF AGENTS INTO CELLS AND TISSUES

STATEMENT REGARDING FEDERALLY SPONSORED RESEARCH

This application is a continuation application under 35 U.S.C. § 111 of International Application No. PCT/US2020/040720, filed Jul. 2, 2020, which claims the benefit of priority of U.S. Provisional Patent Application No. 62/869,831, filed Jul. 2, 2019, which is incorporated herein by reference in its entirety.

CROSS-REFERENCE TO RELATED APPLICATIONS

This application claims the benefit of priority of U.S. Provisional Patent Application No. 62/869,831, filed Jul. 2, 2019, which is incorporated herein by reference in its entirety.

SEQUENCE LISTING

A Sequence Listing accompanies this application and is submitted as an ASCII text file of the sequence listing named "166118_00949_ST25.txt" which is 2.09 KB in size and was created on Jun. 15, 2020. The sequence listing is electronically submitted via EFS-Web with the application and is incorporated herein by reference in its entirety.

INTRODUCTION

For most drugs, the plasma membrane is an impermeable barrier to translocation into the cytoplasm or nucleus of cells. To overcome this barrier, there is significant interest in the development of cell penetrating peptides (CPPs) (Guidotti et al., 2017). A variety of CPPs have been described that enable the delivery of biologically active conjugates including proteins, peptides, DNAs, siRNAs, and small molecule drugs into cells and tissues (Bechara and Sagan, 2013). CPPs have been grouped into a variety of classes: a) cationic, including HIV TAT, penetratin or poly arginine; b) amphipathic, including Transportan and Pep-1 and c) hydrophobic, including Pep-7—these CPPs and their general properties have been reviewed elsewhere (Guidotti et al., 2017). Although CPPs with properties useful for delivery of molecules across plasma membranes have been identified, the efficiency of an individual peptide varies depending on the type of tissue being targeted.

Ocular diseases and injuries remain important medical issues in spite of advances in the pharmaceutical sector. According to the National Institute of Health, ocular diseases that lead to blindness are one of the most common causes of disability in the United States [National Eye Institute (1999-2003). A Report of the National Eye Council, National Institutes of Health]. Delivering drugs to ocular tissues is complicated by the eye's natural defense systems. The blinking action of the eye washes the ocular surface and renews the tear film, which contains immunoglobulins and anti-microbial proteins. The rapid clearance of drugs by the tear film makes topical delivery of molecules to the surface of the eye challenging, resulting in loss of over 95% of a given drug. Further, the half-life of drugs that manage to penetrate to the interior chamber of the eye is usually short due to recycling of the aqueous humor. Thus, improved methods for delivering drugs to ocular tissues are an important medical need.

In the present application, CPPs that target the retina and cornea with high efficiency are provided. These CPPs are unique in that they do not require chemical conjugation between the CPP and heterologous molecule in order to deliver a heterologous molecule across a plasma membrane and, thus, offer a promising means to deliver therapeutics to the retina for treatment of disease and injury.

SUMMARY

The peptides provided herein may act as cell penetrating peptides that are effective for delivery of an agent to a cell or a tissue. In some embodiments, the peptide is not conjugated or linked to the agent and is still capable of crossing the cell membrane and delivering the agent. The present invention provides peptides comprising SEQ ID NO: 1 or having 90% sequence identity to SEQ ID NO: 1, wherein the X in SEQ ID NO: 1 represents an optional flexible linker region. The present invention also provides peptides having an amino acid sequence comprising or consisting of SEQ ID NO: 2 or SEQ ID NO: 4, or peptides having 90% sequence identity to SEQ ID NO: 2 or SEQ ID NO: 4, wherein each X in SEQ ID NO: 2 represents an optional flexible linker region.

Pharmaceutical compositions comprising an agent and the peptides of the present invention are provided. Polynucleotides and nucleic acid constructs encoding the peptides of the present invention are also provided.

Recombinant viruses including polynucleotides encoding the peptides of the present invention are also provided. The peptides of the present invention may be inserted within a viral capsid protein. Adeno-associated viruses (AAV), including AAV9, may be used.

Further, the present invention provides methods of delivering an agent to a cell or a tissue by contacting the cell or the tissue with the disclosed compositions or with an agent and the disclosed peptides or compositions comprising the peptides.

Methods for delivering an agent to a cell or a tissue of a subject by first formulating a medicament comprising the agent and peptides of the present invention and then administering the medicament to the subject are also provided.

Methods for delivering a virus to a cell or a tissue by contacting the cell or the tissue with both a virus and a peptide of the present invention are also provided.

The compositions, peptides and viral delivery mechanisms provided herein may be used to treat a subject in need of treatment for a condition or disease. The conditions or disease may be selected from those involving degenerative ocular disease, diseases associated with inflammation or oxidative stress, neovascularization or fibrosis and ocular injuries.

BRIEF DESCRIPTION OF THE DRAWINGS

The patent or patent application file contains at least one drawing in color. Copies of this patent or patent application publication with color drawings will be provided by the Office upon request and payment of the necessary fee.

DETAILED DESCRIPTION

Figure 1:
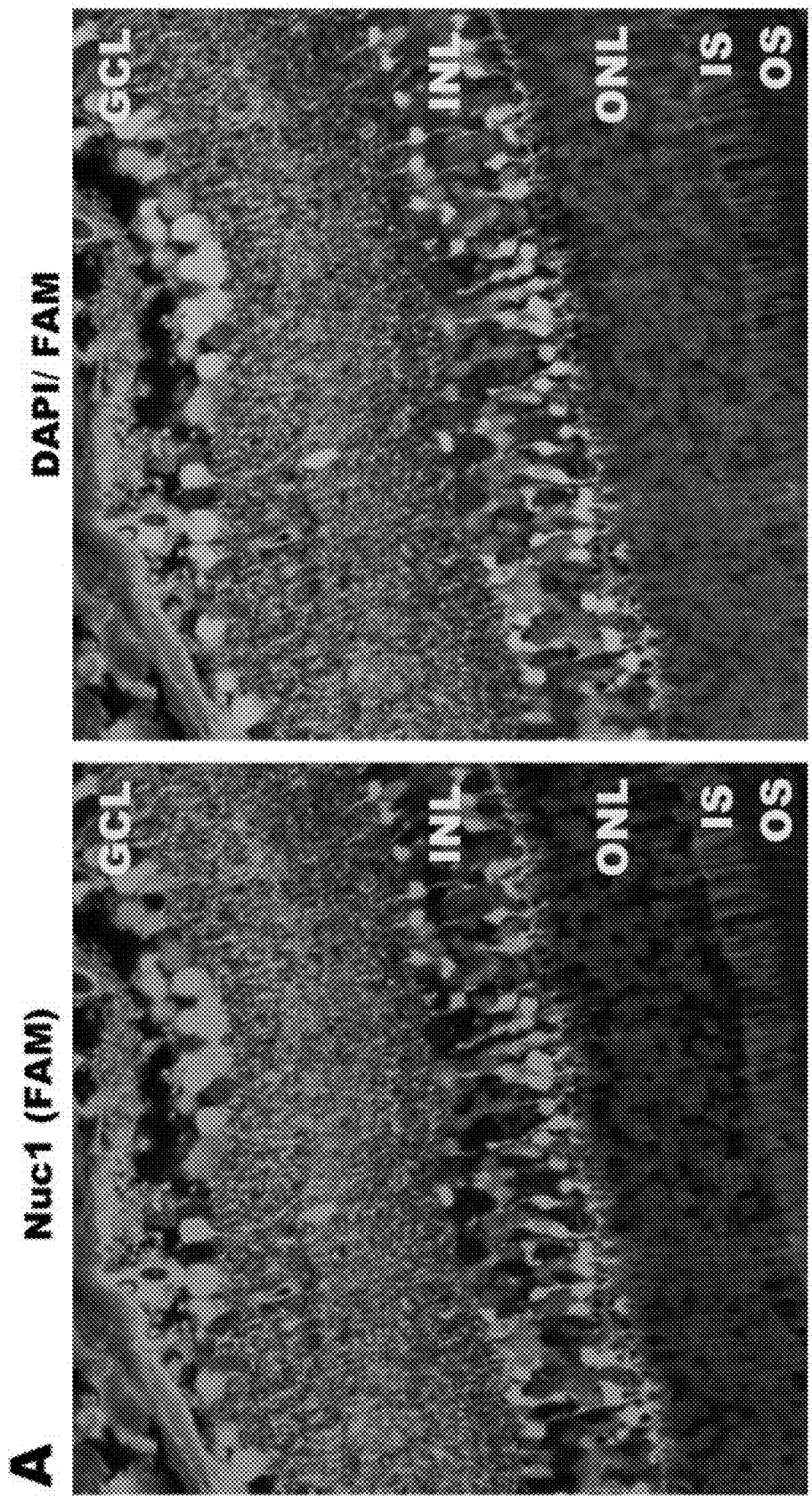
FIG. 1 shows fluorescent microscopy images that demonstrate that Nuc1 peptide penetrates retinal tissues and cells following intravitreal injection. FAM-labeled Nuc1 localizes to all layers of the retina including GCL, INL, IS and OS following intravitreal injection (A). Immunostaining with Tubulin (B), PKC (C), rod opsin (D) and glutamine synthase (E). GCL, ganglion cell layer; ONL, outer nuclear layer; IS, inner segments; OS, outer segments. For some panels higher magnification images are also presented.
Figure 1:
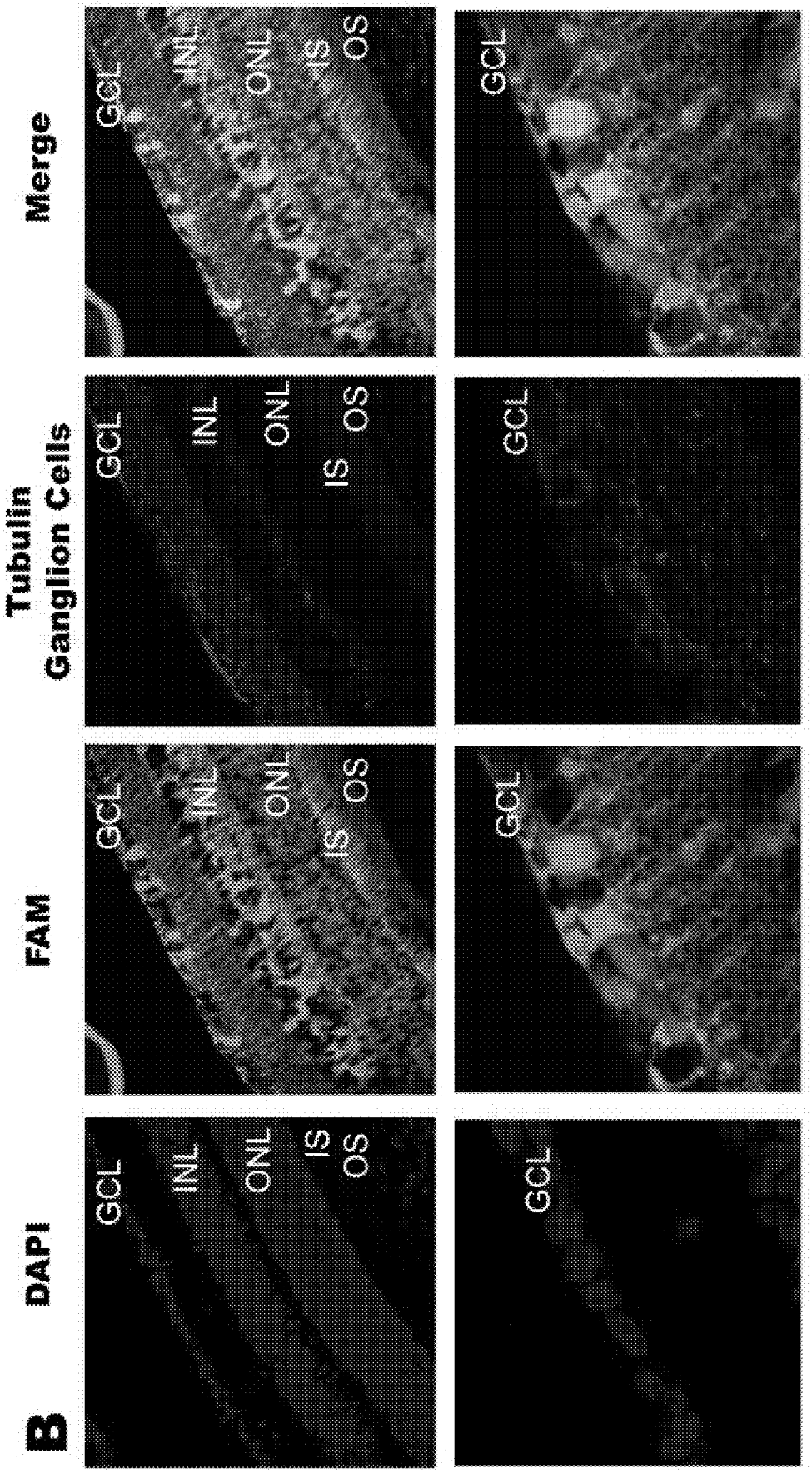

For most drugs, the plasma membrane represents an impermeable barrier. However, a special class of proteins termed cell-penetrating peptides (CPPs), can cross the intact plasma membrane and can facilitate the uptake of cargo molecules. Thus, CPPs enable the delivery of biologically active conjugates including proteins, peptides, DNAs, siRNAs and small molecule drugs into cells and tissues (Bechara and Sagan, 2013). CPPs offer ease of preparation, rapid uptake, and low toxicity and immune response [Jones et al. 2005 Br J Pharmacol 145: 1093-1102]. Well-studied CPPs include the human immunodeficiency virus (HIV) Tat protein [Frankel et al. 1988 Cell 55: 1189-1193], herpes simplex virus (HSV) VP22 protein [Phelan et al. 1998 Nat Biotechnol 16: 440-443], and the Drosophila melanogaster Antennapedia homeodomain protein [Derossi et al. 1994 J Bioi Chem 269: 10444-10450]. For instance, HIV Tat has been shown to function as a CPP that compacts DNA and delivers it to cells in culture [Ignatovich I A et al. 2003 J Biol Chem 278: 42625-42636]. However, apart from HIV TAT, there is very limited information available on the performance of CPPs in neuronal tissues in vivo. Further, CPPs generally require chemical conjugation to a cargo molecule for delivery across the plasma membrane and such modifications can negatively impact the function of the cargo molecule.

The present invention provides peptides for delivery of agents into cells or tissues and in particular into ocular cells and tissues. The peptides of this invention include SEQ ID NO: 1 and SEQ ID NO: 2 as well as other peptides provided herein. While peptides with this ability have been previously described, for example in U.S. Pat. No. 8,778,886, the peptides of the current invention are exceptional in that they do not need to be chemically conjugated or linked to an agent to effectively deliver the agent into a cell or tissue. The Examples demonstrate that one such peptide, termed "Nuc1" and represented by SEQ ID NO: 3, may be the most efficient peptide for penetration of the retina described to date. Further, Nuc1 is able to deliver a diverse array of agents to ocular tissues, including recombinant proteins, antibodies, proteoglycans, steroids, viruses, and ribonucleoproteins.

The peptides used herein were synthesized by a commercial supplier of custom peptides. Peptide synthesis may be performed using a solid-phase technique [Roberge et al. 995 Science 269:202] and automated synthesis is achieved, for example, using the 431A peptide synthesizer (Applied Biosystems, Foster City, Calif.). Those skilled in the art will appreciate that other means may be used to generate peptides, including but not limited to use of protein and peptide expression systems in addition to chemical synthesis.

The CPP described in the Examples, Nuc1, includes two amino acid sequences selected for their potential ability to target ocular cells. The first of these sequences, ASIKVAVSA (SEQ ID NO: 4), is derived from a longer sequence, CSRARKQAASIKVAVSADR (SEQ ID NO: 8), that represents the nucleolin binding region of the basement membrane glycoprotein laminin-1. The second sequence, DKPRR (SEQ ID NO: 5), is derived from a slightly longer sequence, CDKPRR (SEQ ID NO: 7), which forms the heparan sulphate binding domain of a particular isoform of vascular endothelial growth factor (VEGF165). Importantly, both nucleolin and heparan sulphate are found at the surface of retinal tissues, which likely accounts for the ability of these "targeting peptides" to access this tissue.

The peptides of the present invention optionally include a flexible linker region. Nuc1 (SEQ ID NO: 3) includes SEQ ID NO: 4 linked to SEQ ID NO: 5 by an amino acid linker comprising two glycine residues and was shown in the examples to function as a cell penetrating peptide (CPP).

Those of skill in the art will appreciate that the linker region may be altered without affecting the function of the CPP. Thus the peptide provided herein is represented by SEQ ID NO: 1, in which the Xaa amino acid in the sequence represents a flexible linker region. Nuc1 was designed to include a flexible linker region between the targeting peptide sequences (the laminin-1 and VEGF165 derived peptides). A "linker" is a sequence of amino acid residues that serves to connect peptides, optionally via a peptide bond. According to this invention, the flexible linker region comprises 1 or more amino acid residues, preferably 1, 2, 3, 4, 5, 6, 7, 8, 9, 10, 11, 12, 13, 14, 15, 16, 17, 18, 19, or 20 or more residues. In a preferred embodiment of the invention, the linker comprises 2 residues. A "flexible" linker is an amino acid sequence which has no required fixed structure (secondary or tertiary structure) in solution. Such a flexible linker is therefore free to accept a variety of conformations and be comprised of a variety of amino acids. The linker may be provided as an existing linker sequence of a targeting peptide or by insertion of one or more amino acid residues between the targeting peptides. The linker may comprise any amino acid sequence which does not substantially hinder the interaction of the targeting peptides with their corresponding target molecules. Preferred amino acid residues for flexible linker sequences include glycine, alanine, serine, threonine, lysine, arginine, glutamine and glutamic acid, but are not limited thereto. In the Examples, the flexible linker sequence comprises two glycine residues, such that the Nuc1 peptide has an amino acid sequence comprising SEQ ID NO: 3. Those of skill in the art will understand that other residues may be used and that the length of the linker may be altered without adversely affecting the function of the peptide. In certain embodiments, the peptides do not comprise a linker region. Typically, linkers are prepared as part of recombinant nucleic acids encoding both the linker and the targeting peptides. The linker can also be prepared by peptide synthesis and subsequently combined with targeting peptides. Methods of manipulating nucleic acids and of peptide synthesis are well known in the art.

In the present application, the terms "protein" or "peptide" or "polypeptide" are used interchangeably to refer to an amino acid sequence. The peptides described herein are not native, but instead are engineered peptide sequences. An "amino acid" and "amino acid sequence" may include both components that are naturally occurring and components that are non-naturally occurring (i.e., amino acid derivatives or amino acid analogs substituted for one or more naturally occurring amino acids). Further, an amino acid sequence having one or more non-peptide or peptidomimetic bonds between two adjacent residues is included within this definition.

Regarding the peptides described herein, the phrases "% sequence identity," "percent identity," or "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 10, at least 15, at least 20, or more contiguous residues. Such lengths are exemplary only, and it is understood that any fragment length supported by the sequences shown herein, in the tables, figures or Sequence Listing, may be used to describe a length over which percentage identity may be measured.

The Examples demonstrate that Nuc1 can be delivered to all layers of the retina, including ganglion cells, Muller cells, bipolar cells, and photoreceptor rods and cones (FIG. 1). Notably, penetration of Nuc1 into the retina was substantially superior to any of our previously described retinal penetrating peptides, making Nuc1 a promising candidate for the treatment of several ocular conditions. For example, transduction of photoreceptors will have application in the treatment of diseases such as retinitis pigmentosa, while transduction of retinal pigment epithelial cells will have application in the treatment of age-related macular degeneration and transduction of ganglion cells will have application in the treatment of glaucoma. However, the targeted cells or tissues of the present invention are not limited to the eye, as Nuc1 may have use in other tissues including oral, genital, cartilaginous (chondrocyte), liver, kidney, nerve, brain, epithelium, cardiac and muscular tissues. In particular, based on the nature of retinal neurons, we anticipate that the methods of this invention may be extended to other neuronal tissues such as the brain. In the Examples the CPP is able to allow delivery of an agent to photoreceptors, retinal pigment epithelium, ganglion cells, bipolar cells, Muller cells, choroidal endothelial cells, lens epithelium, corneal endothelium, corneal stroma, trabecular meshwork, or the iris.

With this ability to access cells and tissues, the CPPs of the present invention enable the delivery of a diverse array of agents to targeted sites. In certain embodiments, the agent is a therapeutic, detectable, or cytotoxic agent. In some embodiments the agent is selected from the following: a low molecular weight drug, a peptide, a lipid, a carbohydrate, a protein, an antibody, an immunogen, a gene therapy or genetic engineering construct, a virus or viral vector or a vaccine. In other embodiments, the agent is a nucleic acid such as a cDNA, mRNA, miRNA, tRNA, or small interfering RNA. In preferred embodiments, the agent is anti-apoptotic, anti-inflammatory, anti-angiogenic, or anti-fibrotic agent. The agent may be X-linked inhibitor of apoptosis protein, decorin, an antibody against vascular endothelial growth factor, a BH4-domain peptide from Bcl-xL, NRF2, or dexamethasone as shown in the Examples, but many other agents will be apparent to those skilled in the art. In other preferred embodiments, the agent is a gene therapy or gene editing agent. The agent may be a recombinant virus or a Cas9 ribonucleoprotein. For example the vascular endothelial growth factor or rhodopsin may be suitable targets for gene editing. Briefly, in gene therapy, genes are generally delivered into cells as molecules of DNA or RNA. The genes are included as part of expression constructs which also includes a promoter/enhancer element to direct the expression of the gene within the target cells. When the gene is expressed, the resulting protein product supplies a desired function within the target cell. This function may correct a deficiency or an abnormality (mutation, aberrant expression, etc.), or it may ensure the expression of another protein of therapeutic value. Gene therapy may be performed in vitro on cells extracted from the body that are reintroduced after modification, or it may be performed directly in vivo in the appropriate tissue. Thus, in gene editing, the gene within the cell or within cells of a selected tissue are altered to replace the cellular copy of the gene with a modified gene.

In preferred embodiments of the invention, the agent is not chemically conjugated or linked to the CPP. Conjugation can negatively affect the function of the cargo or the agent attached to the CPP. Thus, the ability of the CPPs of the present invention to deliver unconjugated cargo molecules represents a major improvement over the prior art. Further, this ability makes the CPPs extremely versatile due to ease of production. For instance, it allows the efficacy of many cargo molecules or potential agents to be tested in tandem. It also saves time and money that would be spent producing a new conjugated molecule each time a potential cargo molecule is to be tested.

Additionally, polynucleotides encoding the CPPs of the present invention are provided, as well as nucleic acid constructs in which these polynucleotides are operably connected to a promoter. As used herein, the phrase "operably connected to a promoter" means that the polynucleotide is juxtaposed to the promoter such that when gene expression is initiated at the promoter, the polynucleotide is included in the resulting gene product.

The present invention also provides viruses that comprise the polynucleotides and nucleic acid constructs encoding the CPPs. In preferred embodiments, the virus is adeno-associated virus (AAV). AAV vectors have been shown to be a viable and efficacious method of delivering genes to human tissues and in particular ocular, nervous system and liver tissues. However, other viruses that have been modified for use in gene therapy applications may also be employed in the present invention, including retroviruses, adenoviruses, lentiviruses, alphaviruses, flaviviruses, rhabdoviruses, measles virus, Newcastle disease virus, poxviruses, picornaviruses, and herpes simplex viruses. In the Examples, an AAV2 vector pseudotyped with an AAV9 capsid (AAV2/9) was used. However, any AAV serotype, including but not limited to AAV2/2, AAV2/8, or AAV2/5, may be utilized in the present invention [Khabou et al. 2016 Biotechnol Bioeng 113(12): 2712-2724].

In some embodiments, the CPPs are incorporated into a viral capsid protein. Here, the inserted peptide is preferably a shorter portion of Nuc1 comprising only the targeting peptide derived from laminin-1, ASIKVAVSA (SEQ ID NO: 4). In the Examples, this sequence is flanked by two glycine residues to form the sequence GASIKVAVSAG (SEQ ID NO: 6) and is cloned between amino acids 588 and 589 of the AAV serotype 9 capsid protein. Other sites for incorporation of heterologous sequences into AAV capsids, or the outer membrane or capsid proteins of other viral vectors have been previously described. The glycine residues on either end are flexible linker regions that may be altered by those of skill in the art to include different amino acid residues or may be more than one amino acid in length. Thus the peptide provided herein is represented by SEQ ID NO: 2, in which the Xaa amino acid in the sequence represents a flexible linker region (as defined above) that may be one or more amino acid in length and may use distinct amino acid residues.

The viruses described herein may be recombinant viruses or viral like particles (VLP) and include gene therapy vectors or VLPs. As noted above, a CPP sequence can be inserted into a variety of viruses or viral vectors and these can be engineered to allow delivery and expression of a polypeptide in targeted cells. It is contemplated that the viral vectors and viruses described herein will be more effective at delivering the polynucleotide of interest and allow for expression of a polypeptide for the purposes of gene therapy to allow for an increased rate of delivery to a target tissue or cells of a target tissue than if compared to a similar viral vector without insertion or expression of the peptide provided herein. In addition, these recombinant viruses or viral vectors expressing or incorporating a CPP can also be delivered with soluble CPP to further increase delivery to the target cell or tissue. In one embodiment the laminin peptide sequence of SEQ ID NO: 4 or 6 is incorporated into the viral vector and the soluble Nuc1 (SEQ ID NO: 1 or 3) peptide is co-delivered with the virus to increase delivery of the virus and its cargo.

In related embodiments, the peptide is flanked by a different flexible linker region comprising at least one amino acid. As is demonstrated in the Examples, including this portion of Nuc1 in the capsid of AAV (called AAV-IKV in the examples) significantly improves infection of retinal cells when injected subretinally or intravitreally. Notably, infection by this recombinant virus can be further enhanced when the virus (either with or without the inclusion of SEQ ID NO: 4 or SEQ ID NO: 6 in the capsid of the virus) is co-injected with Nuc1.

The present invention provides methods for delivering an agent to a cell or a tissue. These methods involve contacting the cell or the tissue with both the agent and a CPP of the present invention. Cells may be contacted with the agent directly or indirectly in vivo, in vitro, or ex vivo. Contacting encompasses administration to a cell, tissue, mammal, patient, or human. Further, contacting a cell includes adding an agent to a cell culture or topically. Other suitable methods may include introducing or administering an agent to a cell, tissue, mammal, or patient using appropriate procedures and routes of administration as defined herein. In certain embodiments of the method, the cell or tissue is in culture. Alternatively, the cell or tissue is in vivo.

Peptide-mediated delivery of molecules has applications in treatment of ocular disease in humans as well as other diseases. Accordingly, the present invention also provides methods for delivering an agent to a cell or a tissue of a subject. These methods involve formulating a medicament comprising the agent and a CPP of the present invention and administering it to the subject. The current standard of care for treating the wet form of age-related macular degeneration includes monthly intravitreal injection of anti-VEGF antibody (e.g. ranibizumab or avastin) (Comparison of Age-related Macular Degeneration Treatments Trials Research et al., 2012). As demonstrated in the Examples, co-delivering these antibodies with Nuc1 enhances their potency, which would likely reduce the concentration of antibody required for an effective dose or reduce the frequency of dosing. In some embodiments, intravitreal or subretinal injection can be replaced with topical administration. The addition of Nuc1 allows the agent to cross the cornea and reach cells to effect treatment without the need for costly medical visits and intrusive medical procedures. This ability to enhance drug potency has implications for both reducing the cost of treatment and for reducing potential toxicity due to off-target activity. Subjects include, but are not limited to, a vertebrate, suitably a mammal, suitably a human, cows, cats, dogs, pigs, or mice. Other animal models of infection may also be used.

The medicament or pharmaceutical composition of the present invention may optionally be formulated with one or more appropriate pharmaceutically acceptable carrier. Pharmaceutically acceptable carriers include any and all solvents, diluents, or other liquid vehicles, dispersion or suspension aids, surface active agents, isotonic agents, thickening or emulsifying agents, preservatives, solid binders, and lubricants. Remington's Pharmaceutical Sciences [Ed. by Gennaro, Mack Publishing, Easton, Pa., 1995] describes a variety of different carriers that are used in formulating pharmaceutical compositions and known techniques for the preparation thereof. The medicament may also optionally comprise one or more additional therapeutic agents. The additional therapeutic agent may be selected from the group consisting of the following: growth factors, anti-inflammatory agents, vasopressor agents, collagenase inhibitors, topical steroids, matrix metalloproteinase inhibitors, ascorbates, angiotensin II, angiotensin calreticulin, tetracyclines, fibronectin, collagen, thrombospondin, B vitamins, and hyaluronic acid.

The provided methods include administering the medicament using any amount and any route of administration effective for treating the subject. The exact dosage is chosen by the individual physician in view of the patient to be treated. Dosage and administration are adjusted to provide sufficient levels of the active agent(s) or to maintain the desired effect. Additional factors which are taken into account include the severity of the disease state, e.g., extent of the condition, history of the condition; age, weight and gender of the patient; diet, time and frequency of administration; drug combinations; reaction sensitivities; and tolerance/response to therapy. For any active agent, the therapeutically effective dose can be estimated initially either in cell culture assays or in animal models, usually mice, rabbits, dogs, or pigs. The animal model is also used to determine a desirable concentration range and route of administration.

In embodiments in which the targeted tissue is ocular, the medicament can be administered to the eye of a subject by several routes including trans-ocular, intravitreal, topical, trans choroidal, intracameral, supra choroidal, transdermal, subretinal, intra-peritoneal, subcutaneous and intravenous routes. Notably, topical delivery of drugs to the eye is made challenging by the eye's natural defenses. However, as demonstrated in the Examples, topical administration of Nuc1 can enhance delivery of drugs to the cornea. This application is particularly useful as less than 1% of available drugs penetrate into ocular tissue following topical administration [Shell J W 1984 Surv Opthalmol 29: 117-128]. Additional, alternative routes of administration include: oral, rectal, parenteral, intracisternal, intravaginal, intraperitoneal, bucal, or nasal routes.

For ocular administration, liquid dosage forms include buffers and solubilizing agents, preferred diluents such as water, preservatives such as thymosol, and one or more biopolymers or polymers for conditioning the solution, such as polyethylene glycol, hydroxypropylmethylcellulose, sodium hyaluronate, sodium polyacrylate or tamarind gum. Dosage forms for topical or transdermal administration of the medicament include drops, ointments, pastes, creams, lotions, gels, powders, solutions, sprays, inhalants, or patches. The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof. Powders and sprays can contain, in addition to the agents of this invention, excipients such as talc, silicic acid, aluminum hydroxide, calcium silicates, polyimide powder, or mixtures of these substances. Sprays can additionally contain customary propellants such as chlorofluorohydrocarbons.

Injectable preparations, for example, sterile injectable aqueous or oleaginous suspensions are formulated according to the known art using suitable dispersing or wetting agents and suspending agents. The sterile injectable preparation is also a sterile injectable solution, suspension or emulsion in a nontoxic parenterally acceptable diluent or solvent, for example, as a solution in 1,3-butanediol. Acceptable vehicles and solvents include water, Ringer's solution, U.S.P. and isotonic sodium chloride solution. In addition, sterile, fixed oils are conventionally employed as solvents or suspending media. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of solid compositions, which can be dissolved or dispersed in sterile water or other sterile injectable medium prior to use. To prolong the in vivo effect of an active agent, it is often desirable to slow the absorption of the agent from subcutaneous or intramuscular injection. Delayed absorption of a parenterally administered active agent is accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Administration of the medicament or pharmaceutical composition may be therapeutic or prophylactic. Prophylactic formulations are applied to the site of potential wounds, or to sources of wounds, such as contact lenses, contact lens cleaning and rinsing solutions, containers for contact lens storage or transport, devices for contact lens handling, eye drops, surgical irrigation solutions, ear drops, eye patches, and cosmetics for the eye area, including creams, lotions, mascara, eyeliner, and eyeshadow, and to opthalmological devices, surgical devices, audiological devices.

In some embodiments, the subject has an ocular disease, disorder, or injury. Some common diseases of the retina include age-related macular degeneration, retinitis pigmentosa, and glaucoma, which are associated with degeneration of the retinal pigment epithelium, photoreceptors and retinal ganglion cells, respectively [Hartong, et al. 2006 Lancet 368:1795-1809; Rattner et al. 2006 Nat Rev Neurosci 7: 860-872]. The subject may have other diseases and conditions including retinal tear, retinal detachment, diabetic retinopathy, epiretinal membrane, macular hole, macular degeneration, bulging eyes, cataracts, CMV retinitis, retinoblastoma, diabetic macular edema, ocular hypertension, ocular migraine, retinal detachment, alkali or other chemical burn, hyphema, corneal abrasion, keratitis, keratoconus, subconjunctival hemorrhage, proliferative vitreoretinopathy, Usher syndrome, and uveitis. Subjects with other infections, dystrophies or suffering from rejection of transplanted corneas may also be treated.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

EXAMPLES

Example 1

Novel Cell Penetrating Peptide Nuc1 for Delivery of Small and Large Molecules into Retinal Cells and Tissues Cell penetrating peptides (CPPs) may be designed with consideration of the biological properties of the tissue in question. For example, a previously described peptide termed POD (peptide for ocular delivery) was modeled on the glycosaminoglycan binding regions of proteins abundantly present in the retina, specifically acidic and basic fibroblast growth factor (Johnson et al., 2010). The glycosaminoglycan chondroitin sulphate is known to be abundantly present in adult retina (Clark et al., 2011) and heparan sulphate is abundantly present in the retina during development. Molecular modeling of protein-glycosaminoglycan interactions led to the development of POD, which was found to be one of the most efficient CPPs tested in the retina (Johnson et al., 2010). Competition studies indicated that the cell penetrating properties of POD were found to be significantly influenced by the levels of heparan sulphate on the surface of cells (Johnson et al., 2010), identifying heparan sulphate proteoglycans on retinal tissues as candidate moieties for CPP targeting of the retina. The importance of heparan sulphate for CPP function has also been described for an alternative form of CPP known as Vectocell peptides (De Coupade et al., 2005).

Vascular endothelial growth factor (VEGF) plays a key role in retinal homeostasis (Jin et al., 2002; Robinson et al., 2001). The VEGFA165 isoform of VEGF contains a highly basic domain that allows this isoform of VEGF to interact with and localize to the heparan sulfate-rich extracellular matrix (Krilleke et al., 2009). A VEGFA splice variant, VEGFA165b from kidney epithelial cells is identical to VEGFA165 except for the last six amino acids. VEGFA165b and VEGFA165 bind VEGF receptors 1 and 2 with similar affinity. However, VEGFA165b only weakly binds to heparan sulfate (Cebe Suarez et al., 2006), implicating the C terminus (SEQ ID NO: 7 CDKPRR) of VEGF165 in heparan sulphate binding.

Laminin is a large basement membrane glycoprotein of the extracellular matrix. The laminins influence tissue development, cell differentiation, migration and adhesion (Aumailley, 2013). Laminins are heterotrimeric proteins, each of which contain an α-chain, a β-chain and a γ-chain. The trimeric proteins intersect to form a cross-like structure that can bind to other cell membrane and extracellular matrix molecules. Thus far, five α, four β, and three γ variants have been identified. Different combinations of these chains give rise to a large number of laminin molecules. Thus far, approximately 16 laminin molecules have been identified in mammals. At least seven laminin chains, α3, α4, α5, β3, γ2 and γ3 have been localized to the matrix surrounding photoreceptors and the first synaptic layer where photoreceptors synapse with retinal interneurons (Libby et al., 2000). Laminin also binds to other basement membrane constituents including heparan sulphate proteoglycans and it mediates cellular interactions with basal lamina. A region (SEQ ID NO: 8 CSRARKQAASIKVAVSADR) proximal to the carboxyl globule of laminin-1 is an active site for cell adhesion (Tashiroet al., 1989). Interestingly, this region also binds to nucleolin (Kibbey et al., 1995), a protein that is typically found in the nucleus and surface of rapidly dividing cells (Hovanessian et al., 2010; Koutsioumpa and Papadimitriou, 2014; Mongelard and Bouvet, 2007) but is also found on the retina, including photoreceptors (Hollander et al., 1999).

We hypothesized that a novel peptide sequence comprised of a portion of the nucleolin-binding region from laminin-1 in combination with the heparan sulphate proteoglycan-binding region of VEGFA165, linked through a flexible polyglycine linker, may have cell adhesion and cell penetrating properties. Thus, we tested the sequence ASIKVAVSAGGDKPRR (SEQ ID NO: 3) for such properties. Although we demonstrate here that this peptide, Nuc1 (SEQ ID NO: 3), may function efficiently in the retina, it may also function in other tissues that share extracellular matrix and cell surface properties with retinal tissues, e.g. brain.

Materials and Methods:

Peptide Synthesis: The fluorescently labeled Nuc1 peptide sequence Fluo(5/6FAM)-ASIKVAVSAGGDKPRR [COOH] (SEQ ID NO: 3) was synthesized by Thermo Fisher Scientific to >99% purity. The same sequence without fluorescent labeling was also synthesized.

Animals: This study was carried out in accordance with the Statement for the Use of Animals in Ophthalmic and Vision Research, set out by the Association of Research in Vision and Ophthalmology (ARVO) and was approved by Tufts University Institutional Animal Care and Use Committee (IACUC). Six to eight week old C57BL/6J mice were purchased from Jackson Laboratory (Bar Harbor, Me.) and housed under a 12 h light/dark cycle.

Intravitreal and subretinal injections: Mice were anesthetized by injecting intraperitoneally a cocktail mixture containing Ketamine (100 mg/kg, Phoenix™, St Joseph, Mo.) and Xylazine (10 mg/kg, Lloyed, Shenandoah, Iowa) followed by topical application of 0.5% proparacaine hydrochloride (Akorn Inc., Lake Forest, Ill., USA) for topical analgesia to the cornea. Mice were kept warm during anesthesia. Intravitreal and subretinal injections were performed using a 32-gauge needle and a 5µl glass syringe, as previously described (Cashman et al., 2015). For Nuc1 uptake experiments, the amounts of peptide injected are indicated in results. For studying effect of Nuc1 on mCherry uptake, 1ul mCherry (4ug) was injected intravitreally with or without Nuc1 as described in results. Four hours post injection (as indicated), eyes were enucleated and fixed in 4% paraformaldehyde. A total of 1 µl of AAV (doses described in results) was injected per eye with or without Nuc1 intravitreally and subretinally. Retinal cryosections were taken using a Micron 550 cryostat.

Laser induced choroidal neovascularization (CNV): Laser photocoagulation was performed as previously described. Briefly, the pupils of sedated mice were dilated with 2.5% phenylephrine HCl (Bausch & Lomb) and 1% tropicamide (Bausch & Lomb). 2.5% hypermellose (Goniovisc) was applied to minimize corneal discomfort. Four laser spots were generated per eye using an argon laser (532 nm, IRIS Medical Light Solutions, IRIDEM; IRIDEX) set to a spot size of 75 µm in diameter, 330 mH, and 100 ms pulse time.

Lectin and α-actin staining: Seven days after photocoagulation, animals were euthanized with $CO_2$, and eyes were enucleated. The eye cups were fixed and the lens and cornea were removed. After overnight fixation in 4% paraformaldehyde in 0.1 M phosphate buffer, the retina was removed and the sclera/choroid/RPE complex was washed in PBS. The eye cups were blocked in 5% BSA in PBS, and stained with 100 µg/µL fluorescein-conjugated isolectin (Vectashield) in PBS for 1 hr. Eyecups were then washed in PBS three times for five minutes and incubated overnight at 4° C. with anti α-SMA Cy3-conjugated mouse monoclonal antibody (C6198, Sigma) at a 1:200 dilution. The following day, eye cups were washed three times with PBS for 5 minutes, flat mounted on glass slides, and imaged using an inverted microscope (IX51; Olympus) with relevant filters, a digital camera (Retiga 2000R-FAST; Q-Imaging), and QCapture Pro software (Q-Imaging). CNV area images were captured by fluorescence microscopy (Leica). CNV area was measured using ImageJ software (NIH).

Cell culture: Passage HEK293 cell cultures were maintained on 15-cm plates in Dulbecco's modified Eagle's medium (DMEM, Gibco) with added 10% fetal bovine serum (FBS; HyClone Laboraties, South Logan, Utah). The cells were passaged every 3-4 days to maintain them exponential growth phase.

Vector constructs: For production of AAV-IKV-GFP and AAV-Nuc1-GFP viruses, pAAV9/rep-cap plasmid was digested with DraIII and a 1.4 kb cap DNA fragment was gel extracted and cloned into pBSx to generate pBSx1.4. The DNA sequences for the peptide were commercially synthesized. These sequences were cloned into pBSx1.4 (containing the 1.4 kb cap region) by restriction digestion using TthIII1 and BamHI to generate pPBSx1.48 and pBSx1.4N. Finally, pPBSx1.48 and pBSx1.4N were digested with SbfI and BsiWI and a 1.4 kb DNA fragment was gel extracted and cloned into pAAV2/9rep-cap containing inverted terminal repeats (ITR) generating pAAV2/9IKV and pAAV2/9Nuc 1.

Production and purification of recombinant AAV: AAV virus was generated using a modified version of a previously described protocol (Birke et al., 2014). Transfections were done using calcium phosphate triple transfection of AAV plasmids described above. In brief, the 80-90% confluent HEK293 cells grown in 15 cm plates were changed to DMEM-10% FBS 2 hours before transfection. Adequate amounts of the plasmids, at a ratio of 2:1:1 (helper plasmid: cis plasmid: trans plasmid), were precipitated using the calcium phosphate method and added dropwise to 20 plates. The media was exchanged to DMEM-10% FBS 24 hours post transfection. Cells and medium were harvested 96 hours post transfection. The collected cell pellet was lysed and 14 ml of clarified lysate was applied to a gradient of iodixanol (OptiPrep; Sigma-Aldrich, St Louis, Mo.) solution filled in the following order: 4 ml of 15%, 9 ml of 25%, 9 ml of 40%, and 5 ml of 54% iodixanol in a 40 ml Quick-Seal centrifuge tubes (Beckman Instruments, Palo Alto, Calif.). The tubes were centrifuged at 69,000 rpm in a 70Ti rotor (Beckman Instruments) at 18° C. and 4 ml of fractionated solution from the 40% iodixanol layer was removed. The fraction was further diafiltered and concentrated using final lactated ringer's solution and glycerol added to 5%. The fraction was then aliquoted and stored at −80° C. for future use.

AAV titration: AAV-CAG-GFP plasmid was digested with SmaI and gel extracted to generate a standard curve for the GFP transgenes. AAV was digested with DNaseI to remove genomic DNA and further incubated with Proteinase K to digest the AAV capsid. The DNA was extracted and purified using Phenol-Chloroform method and dissolved in TE buffer. A standard curve was prepared ranging from $2\times10^4$ genome copies to $2\times10^8$ genome copies. Quantitative PCR was performed to quantify virus against the standard curve.

Immunohistochemistry: To perform retinal cell immunohistochemisrty, cryostat retinal sections were rehydrated in PBS for 15 min, blocked with 6% normal goat serum in PBS or using a Mouse On Mouse Kit for 1 hr, and incubated overnight in a moist chamber with the appropriate primary antibodies against PKC (bipolar cells). Subsequently, sections were washed and incubated with secondary antibodies labeled with Alex-fluor 544 or 488 (Molecular Probes, Eugene, Oreg.) to localize respective antibodies in retinal sections. Slides were mounted in anti-fade medium containing DAPI (Vectashield-DAPI; Vector Laboratories, Burlingame, Calif.) to counterstain the nuclei, and images were captured with a Leica confocal microscope.

Results

Nuc1 Penetrates Retinal Tissues and Cells Following Intravitreal Injection

To examine whether Nuc1 peptide can penetrate the retina and enter retinal cells following intravitreal injection, we fluorescently labeled Nuc1 with the fluorescent dye FAM and injected a total of 1 ug Nuc1 suspended in 1 ul $H_2O$ into the vitreous of adult (6 week old) C57BL/6J mice. Four hours post injection, eyes of these mice were enucleated and fixed in 4% paraformaldehyde. Retinal cryosections were generated using a Micron 550 cryostat and sections were imaged using a fluorescent microscope. We found that whereas 6-FAM was unable to penetrate retina (data not shown), FAM labeled Nuc1 was localized to all layers of the retina, including the ganglion cell layer (GCL), inner nuclear layer (INL), outer nuclear layer (ONL), inner segments (IS) and outer segments (OS) (FIG. 1A). Co-staining of these cryosections with antibodies targeting tubulin (FIG. 1B), protein kinase C (FIG. 1C), rod opsin (FIG. 1D), or glutamine synthase (FIG. 1E) revealed that Nuc1 targeted ganglion cells, bipolar cells, photoreceptors, and Muller cells respectively. Interestingly, penetration of Nuc1 into the retina was substantially superior to any of our previously described retinal penetrating peptides including POD (Binder et al., 2011; Johnson et al., 2010). To our knowledge, Nuc1 has superior retinal penetrating properties relative to any previously described cell penetrating peptide for the retina.

Nuc 1 Facilitates Recombinant Protein Penetration into the Retina

Figure 2:
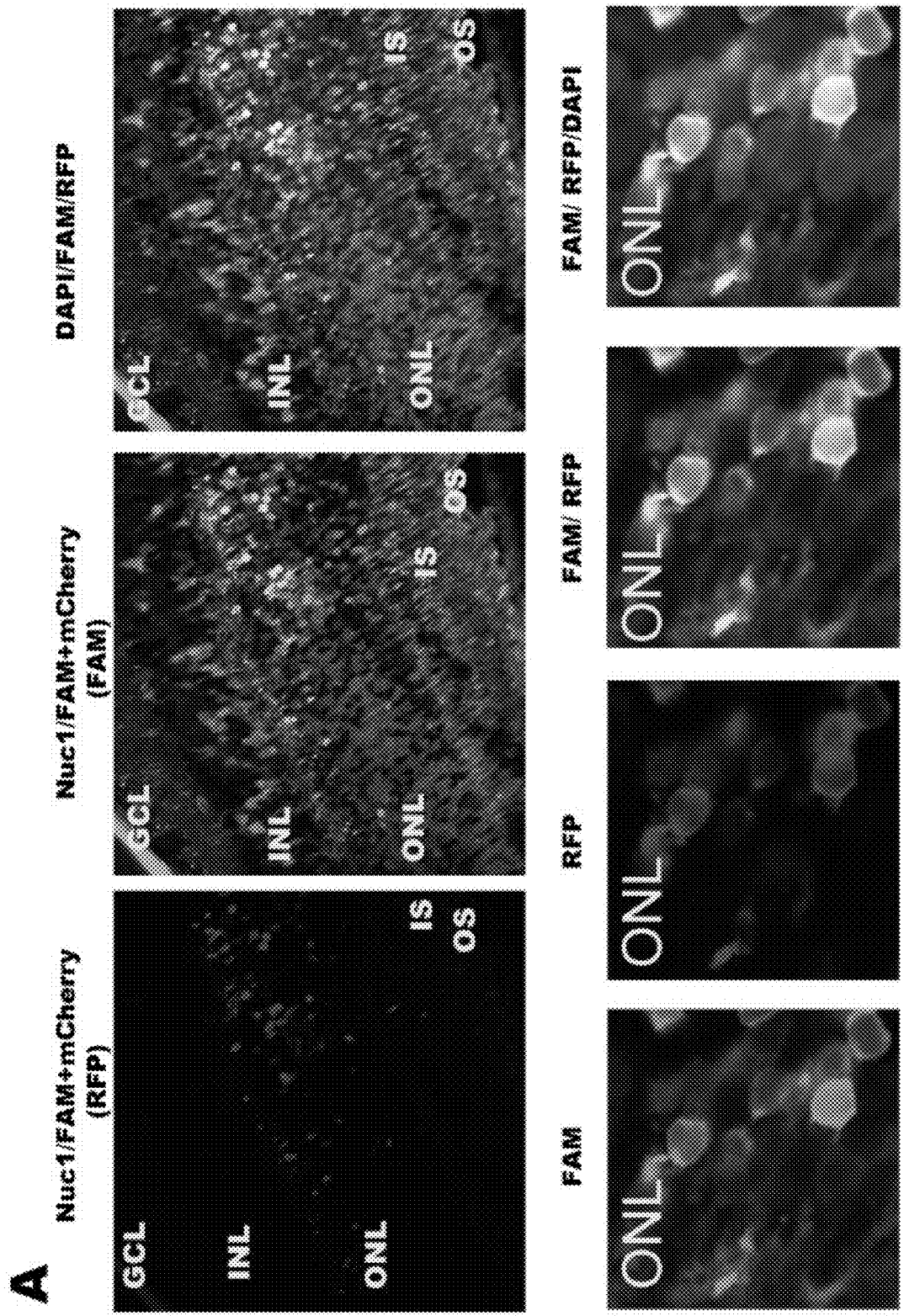
FIG. 2 shows representative fluorescent microscopy images that demonstrate that Nuc1 facilitates recombinant protein penetration into retinal cells. Co-injection of mCherry/RFP and FAM-labeled Nuc1 into the vitreous of adult mice leads to uptake of mCherry into a variety of retinal cell types, most abundantly in the ONL (A). Higher magnification of ONL is presented (A). Frozen sections of mice co-injected with mCherry and non-labeled Nuc1 were stained for Tubulin for ganglion cells (B), PKC for bipolar cells (C), glutamine synthase for Muller cells (D) or cone opsin (E). Notably, recombinant mCherry/RFP protein does not significantly penetrate the retina when injected alone intravitreally (F), as indicated by a lack of RFP signal in the center panel. GCL, ganglion cell layer; ONL, outer nuclear layer; IS, inner segments; OS, outer segments. For some panels higher magnification images are also presented.
Figure 2:
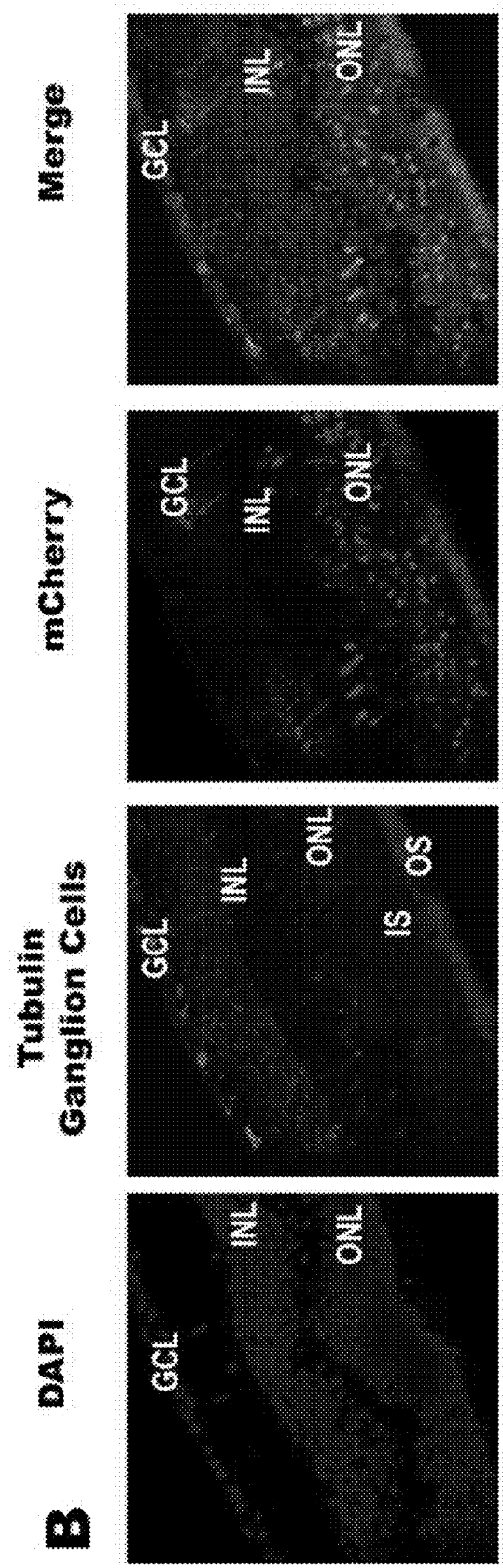
Figure 2:
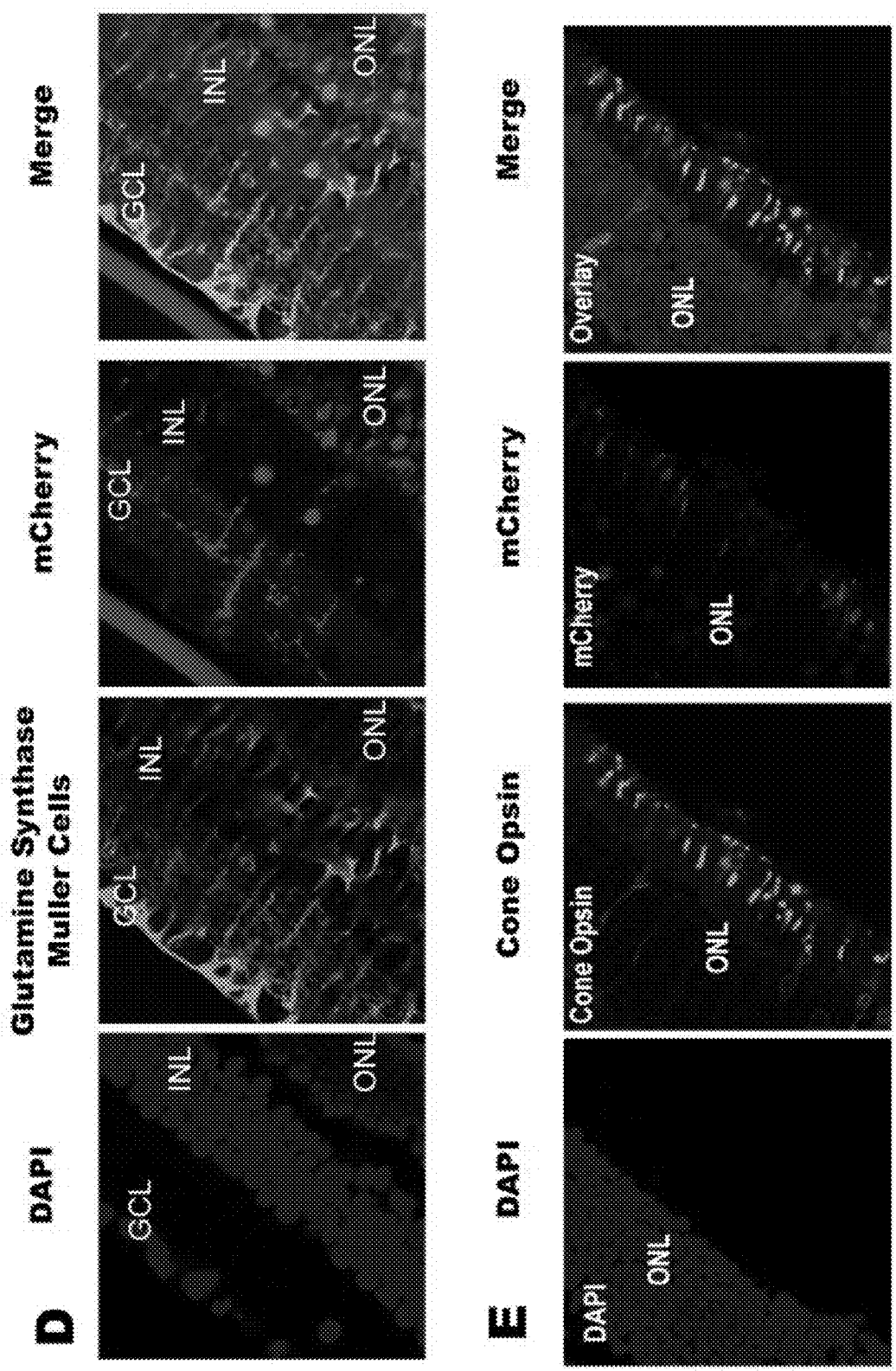

Large functional proteins injected into the vitreous do not generally penetrate deep into the retina and do not cross the plasma membrane of retinal cells. Use of cell penetrating peptides (CPPs), such as POD, physically linked to heterologous proteins can overcome this inherent limitation (Johnson et al., 2010). However, POD and other CPPs generally require chemical conjugation to the heterologous protein for delivery across the plasma membrane and such modifications to proteins could negatively impact protein function. We hypothesized that a heterologous protein could be delivered into retinal cells without the need for conjugation to Nuc1. To test this hypothesis, we co-injected 4 μg of a recombinant red fluorescent protein (RFP/mCherry) with 1 μg FAM-labeled Nuc1 into the vitreous of adult (6 week old) C57BL/6J mice. After 4 hours, tissues were processed as described above. Whereas there was no significant penetration of mCherry into retinal tissues or cells when injected alone (FIG. 2F), mCherry co-injected with FAM-labeled Nuc1 exhibited significant uptake of mCherry into a variety of retinal cells (FIG. 2A), most abundantly in the ONL. Notably, colocalization (yellow) of the FAM signal (green) with mCherry signal (red) was detected in many cells within the ONL of the retina (FIG. 2A).

When FAM labeled Nuc1 was replaced with unlabeled Nuc1 and co-injected with mCherry, robust uptake of mCherry was again observed, demonstrating that the RFP signal was not the result of bleed-through from the FAM channel (FIG. 2B-2E). Co-staining of retinal sections with antibodies to tubulin (FIG. 2B), PKC (FIG. 2C), glutamine synthase (FIG. 2D) or cone opsin (FIG. 2E) revealed that mCherry was localized to ganglion cells, bipolar cells, Muller cells and cone photoreceptors respectively. Due to the small size of the mouse eye, there was some variability observed between animals, however, all retinas exhibited the strongest signal in the ONL.

Nuc1 Facilitates the Delivery of XIAP Protein into the Retina and Attenuates Apoptosis Next, we investigated whether the properties of Nuc1 may be applicable to heterologous proteins of potential therapeutic significance. Programmed cell death or apoptosis is a common pathway activated as a consequence of retinal degeneration in diseases such as retinitis pigmentosa (Cottet and Schorderet, 2009). Prior studies using transgenic animals or viral gene delivery have found that elevated expression of inhibitors of apoptosis, such as X-linked inhibitor of apoptosis protein (XIAP), attenuates retinal degeneration in a variety of animal models of retinal degeneration (Leonard et al., 2007). As an alternative to transgene delivery, one may envisage delivery of XIAP protein for the treatment of retinal degenerative diseases. This method of treatment is analogous to the current standard of care for the wet form of age-related macular degeneration (AMD, see below), whereby a recombinant protein (e.g. aflibercept) is injected intravitreally to target VEGF. Relative to gene delivery, protein delivery may be more readily titrated for dosing regimens. Intraperitoneal injection of N-methyl-N-nitrosourea (MNU) in mice causes selective induction of apoptosis in the outer nuclear layer (ONL) of the retina and thus this model is useful for testing the efficacy of inhibitors of apoptosis (Petrin et al., 2003).

To test the hypothesis that purified functional recombinant human XIAP could be delivered into retinal cells via intravitreal injection and inhibit MNU induced apoptosis in the retina, C57BL/6J mice (male, 6-8 weeks old) were injected intravitreally with 1.4 µg recombinant human XIAP (n=6 eyes) or XIAP co-injected with 0.4 µg Nuc1 (n=6 eyes). After 4 h, mice were injected intraperitoneally with 50 mg/lkg MNU. Some mice were injected intraperitoneally with PBS only, as a measure of background apoptosis in the retina. After an additional 24 hours, the eyes of mice were enucleated and processed as above. To detect apoptotic cells, the terminal deoxynucleotidyl transferase-mediated dUTP-biotin nick-end labeling (TUNEL) method was performed on cryosections using the In Situ Cell Death Detection Kit, TMR Red (Sigma) as per manufacturer's instructions. The eye sections were imaged and used for quantification of TUNEL positive cells using ImageJ (FIJI version and plug in) as described previously (Maidana et al., 2015).

Figure 3:
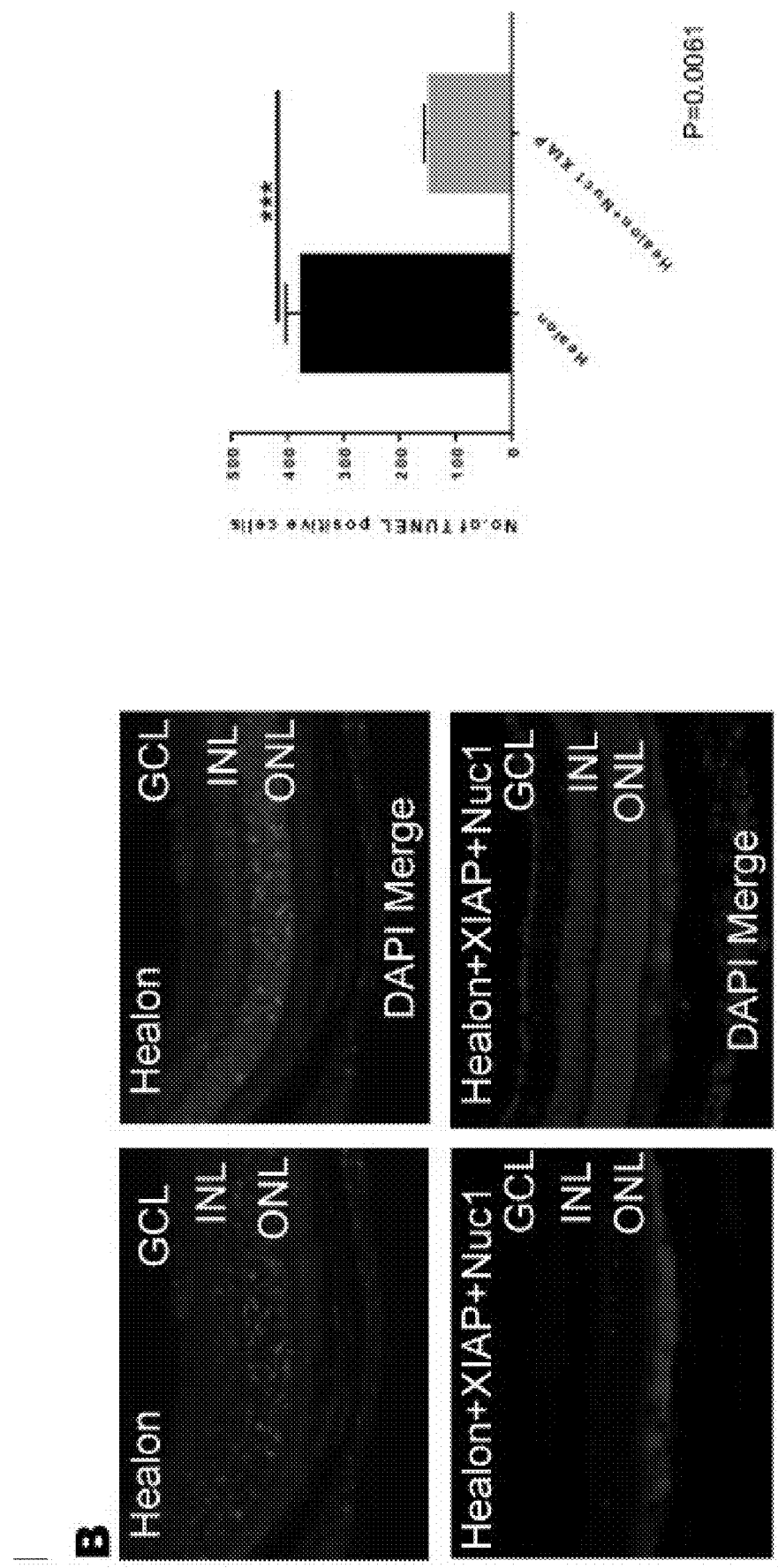
FIG. 3 demonstrates that Nuc1 facilitates the delivery of functional proteins into the retina. TUNEL staining for apoptotic cells was performed in normal, MNU, MNU+XIAP or MNU+XIAP+Nuc1 injected mice. Mice were challenged with PBS for determination of normal levels of apoptotic cells or for MNU-induced apoptosis. Nuc1 co-injected with XIAP confers significant protection against apoptosis relative to XIAP only injected mice (A). Significant inhibition of apoptosis following Nuc1+XIAP was also observed in a retinal detachment model (B). GCL, ganglion cell layer; ONL, outer nuclear layer; INL; inner nuclear layer.

As anticipated, intraperitoneal injection of MNU induced extensive apoptosis in the ONL, as evident from the high number of TUNEL positive cells in this group of animals relative to PBS injected animals (FIG. 3). Eyes injected with XIAP protein only (intravitreally) prior to MNU injection exhibited no significant reduction (2.2%, p=0.9902) in the number of TUNEL positive cells relative to MNU only (FIG. 3A). In other words, XIAP by itself did not significantly attenuate apoptosis in the ONL. In contrast, animals that were co-injected with recombinant XIAP protein and Nuc1 (intravitreally) prior to MNU injection, exhibited a significant reduction (65.7%, p<0.0001) in the number of TUNEL positive cells. This demonstrates that Nuc1 enables functional XIAP protein to penetrate the retina and inhibit apoptosis in the ONL. Notably, while we have shown in a previous study that recombinant XIAP protein can be delivered to the retina and inhibit MNU induced apoptosis, in the current study XIAP did not need to be chemically conjugated to the delivery reagent. Thus, this study reveals a significant advancement in the development of functional protein delivery into retinal cells (Talreja et al., 2018).

Having demonstrated that functional XIAP could be delivered into the retina when co-injected with Nuc1, we wished to test whether our findings could be applied to additional models of retinal apoptosis. Rhegmatogenous, tractional, and exudative retinal detachment are associated with risks of blindness. Detachment of the retina results in retinal cell apoptosis within the outer and inner retina (Arroyo et al., 2005). We wished to test the hypothesis that a combination of Nuc1 and recombinant XIAP could inhibit apoptosis of retinal cells in a murine model of retinal detachment. To test this hypothesis, we created a detachment in the retina of mice by injection of 3 µl (10 mg/ml) of sodium hyalouronate (Healon, Advanced Medical Optics, Sweden) into the subretinal space using a 32G needle connected to a 5µl glass syringe (Hamilton). One day following retinal detachment, animals were co-injected intravitreally with 1.4 µg XIAP and 0.4 µg Nuc1. 72 hours later, eyes were fixed in 4% paraformaldehyde and cryosections were taken using a Micron 550 cryostat and stained for TUNEL as described above. We found that there was an approximately 60% (p=0.0061) reduction in the number of TUNEL positive cells when the combination of Nuc1 and XIAP was injected into the retina relative to the Healon only control (FIG. 3B).

Nuc1 Facilitates the Delivery of Antibodies to the Retina

Figure 4:
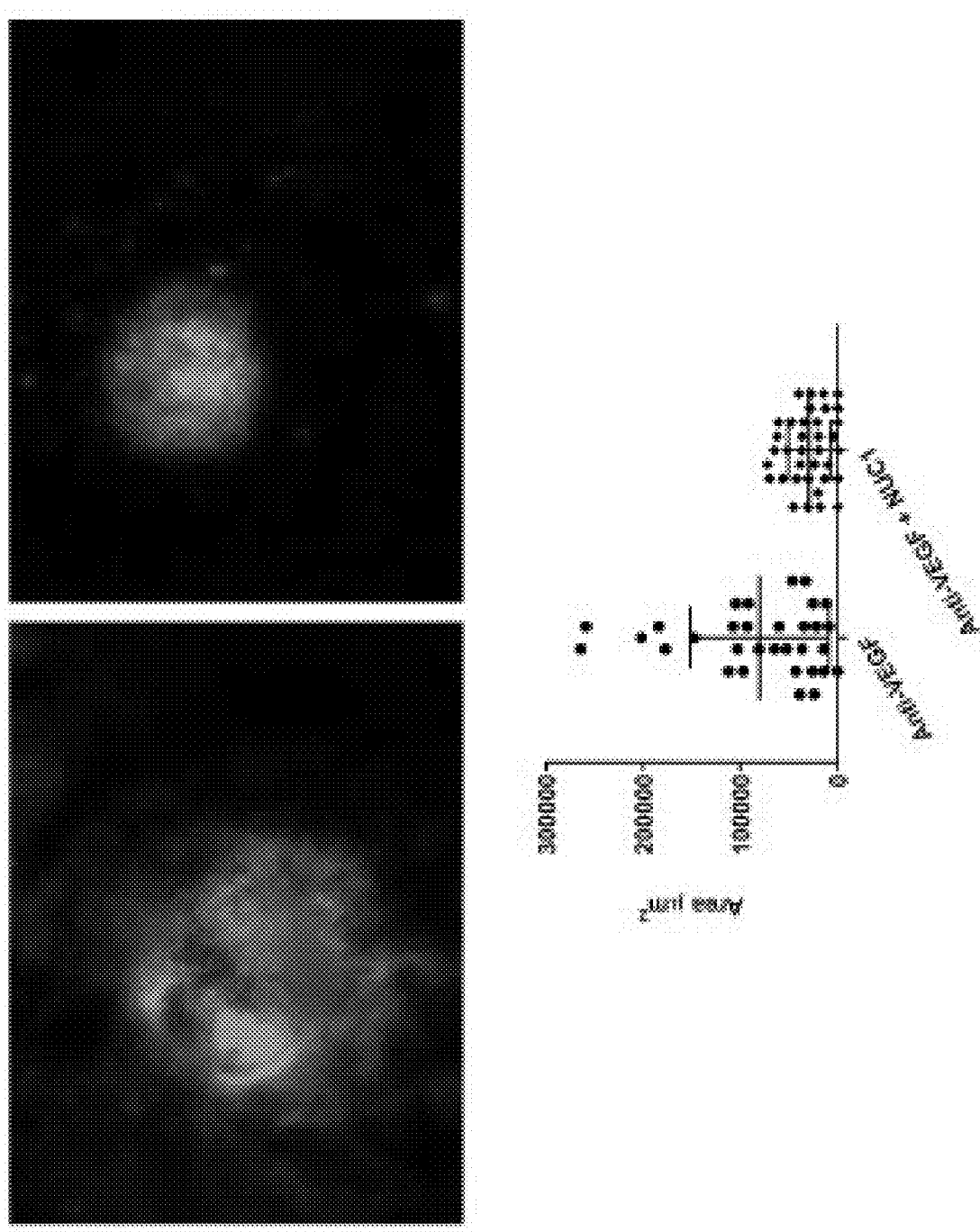
FIG. 4 demonstrates that Nuc1 facilitates the delivery of antibodies into the retina. Anti-VEGF antibody inhibits laser induced neovascularization (CNV) that can be enhanced by co-administration of anti-VEGF antibody with Nuc1; injected either intravitreally (A) or delivered as daily topical drops for 10 days (B). Fluorescent microscopy images of RPE/choroid flat mounts stained with FITC-conjugated Griffonia Simplicifolia Lectin I are shown above, and the area of the laser spots is quantified in a scatterplot below.
Figure 4:
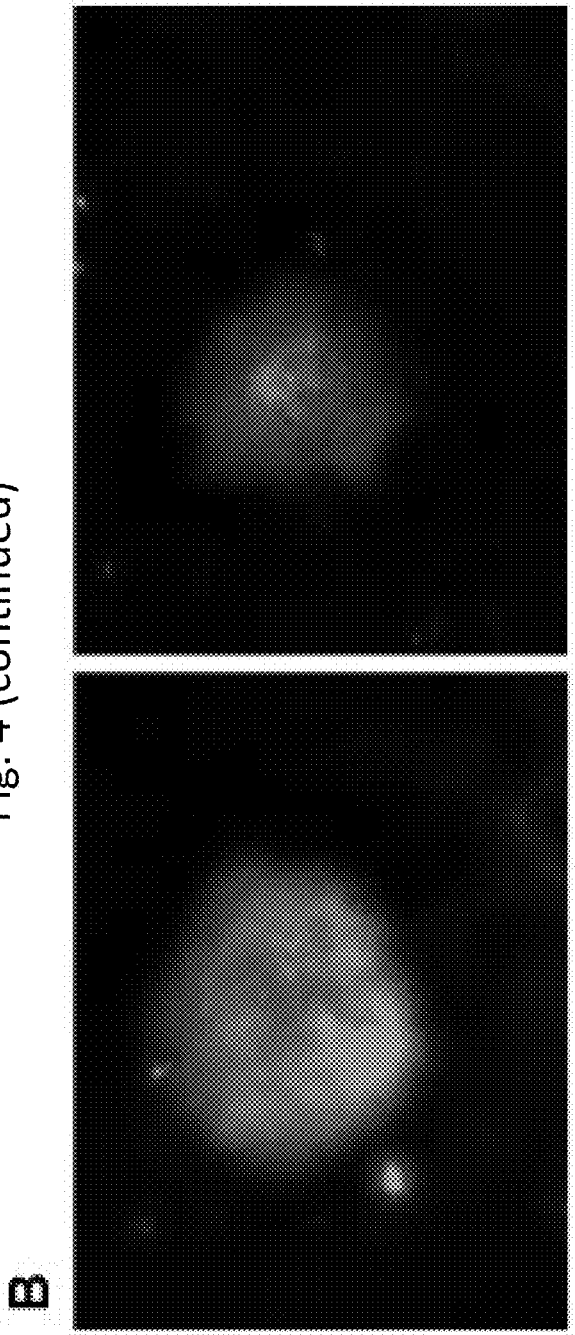
Figure 4:
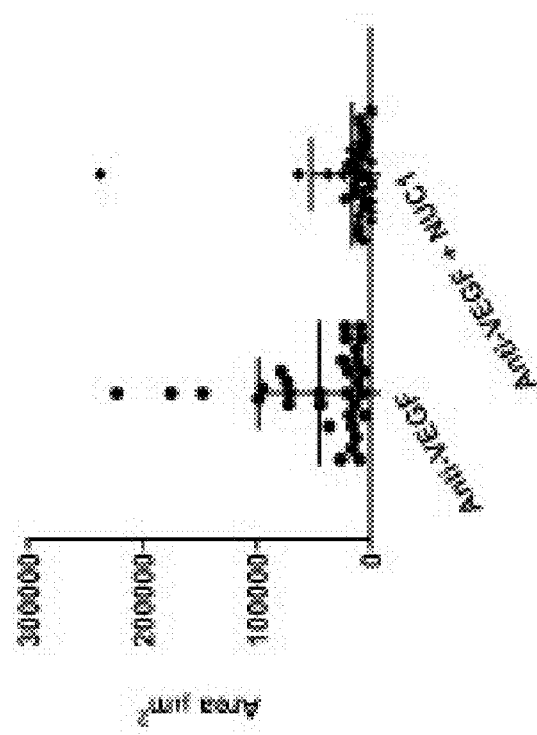

Although our results above suggest that recombinant proteins may be readily utilized for potential treatment of retinal diseases, the current clinical standard of care for the treatment of the wet form of age-related macular degeneration (AMD) includes monthly intravitreal injection of anti-VEGF antibody (e.g. ranibizumab or avastin) (Comparison of Age-related Macular Degeneration Treatments Trials Research et al., 2012). To determine whether Nuc1 could improve the delivery of antibodies into retinal cells or tissues, we examined the therapeutic efficacy of an anti-VEGF antibody in the murine model of wet AMD. Laser induced choroidal neovascularization (CNV) was generated through application of four laser spots around the optic nerve head at a 330 mW power and 100 ms duration. Mice were subsequently injected intravitreally with either 0.3 ng of anti-VEGF antibody only or with 0.3 ng anti-VEGF antibody in combination with 1 µg Nuc1. The amount of anti-VEGF antibody utilized in these studies was determined by pilot studies (i.e., titration of 3 µg to 0.3 µg of anti-VEGF, data not shown). The dose was calculated such that the anti-VEGF antibody alone would fail to significantly inhibit laser induced CNV. At 7 days post laser treatment, eyes were harvested and RPE/choroid flat mounts stained with FITC-conjugated Griffonia Simplicifolia Lectin I were prepared. Laser spots were imaged by a fluorescence microscope and the area of the laser spots quantified using ImageJ software. We found that relative to anti-VEGF antibody alone, there was a significant reduction (>60%; p<0.0001) in the size of CNV spots when anti-VEGF antibody was co-injected with Nuc1 (FIG. 4A). Thus, intravitreal administration of Nuc1 significantly enhances the penetration and efficacy of anti-VEGF antibody against laser induced CNV. This property of Nuc1 may be useful for either enhancing or reducing the efficacy of antibodies, altering the potency of a given dose of antibody such that more or less is needed to achieve a therapeutic effect.

Although intravitreal injection of antibodies is a current standard of clinical care for wet AMD, it is an invasive and 'uncomfortable' procedure for patients and is associated with retinal detachment and endophthalmitis. Furthermore, it requires frequent patient visits to the ophthalmologist, generally by elderly individuals, leading to reduced patient compliance. Thus, topical administration of a drug would be a preferred approach to drug delivery. We examined whether Nuc1 could enhance the potency of topically applied anti-VEGF antibody. To account for the significantly limited penetration of antibodies when applied topically to eyes, we utilized higher doses of antibody relative to intravitreal injection. Specifically, 1.8 µg of anti-VEGF antibody alone or 1.8 µg of anti-VEGF antibody in combination with 4 µg of Nuc1 was administered. Following laser-induced CNV, a topical drop containing antibody and Nuc1 was applied to the cornea twice daily for ten days. Topical delivery of Nuc1 significantly enhanced the efficacy of topically applied anti-VEGF antibody, resulting in a ~60% (p<0.02) reduction in the size of laser induced CNV (FIG. 4B) relative to antibody alone. Thus, Nuc1 significantly enhances the potency of topically applied antibody in the laser induced model of wet AMD.

Nuc1 Facilitates the Delivery of Decorin Protein into the Cornea and Inhibits Fibrosis To further evaluate the potential of Nuc1 as a platform for protein delivery to ocular tissues, we examined additional models of ocular disease. Alkali burn of the cornea leads to fibrosis, angiogenesis and inflammation that, if left untreated, result in a significant loss of vision. Decorin is a proteoglycan known to have anti-angiogenic and anti-fibrotic properties (Gubbiotti et al., 2016; Jarvelainen et al., 2015).

Figure 5:
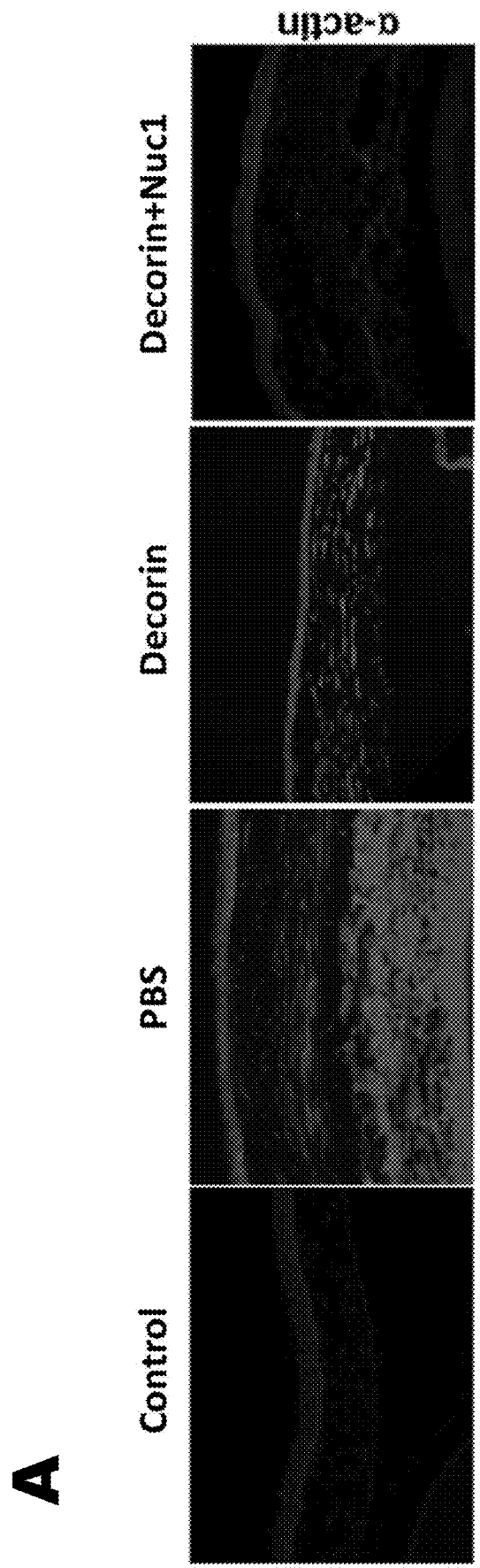
FIG. 5 demonstrates that Nuc1 enhances the potency of decorin for the treatment of alkali burn and choroidal neovascularization (CNV). Corneal cryosections collected from a mouse model of alkali burn were stained for α-actin, a marker of fibrosis (red), and nuclei are stained with DAPI (blue) (A). Fluorescent microscopy images of isolectin and alpha smooth muscle actin (α-SMA) staining in the eyes of mice with laser induced CNV treated with intravitreal injection of either decorin alone or in combination with Nuc1 peptide (decorin+Nuc1) (B). Dot plots of the data presented in (B) of the area of isolectin (left) and α-SMA (right) staining measured in the eyes of mice with laser induced CNV treated with intravitreal injection of either decorin alone or in combination with Nuc1 peptide (decorin+Nuc1) (C).
Figure 5:
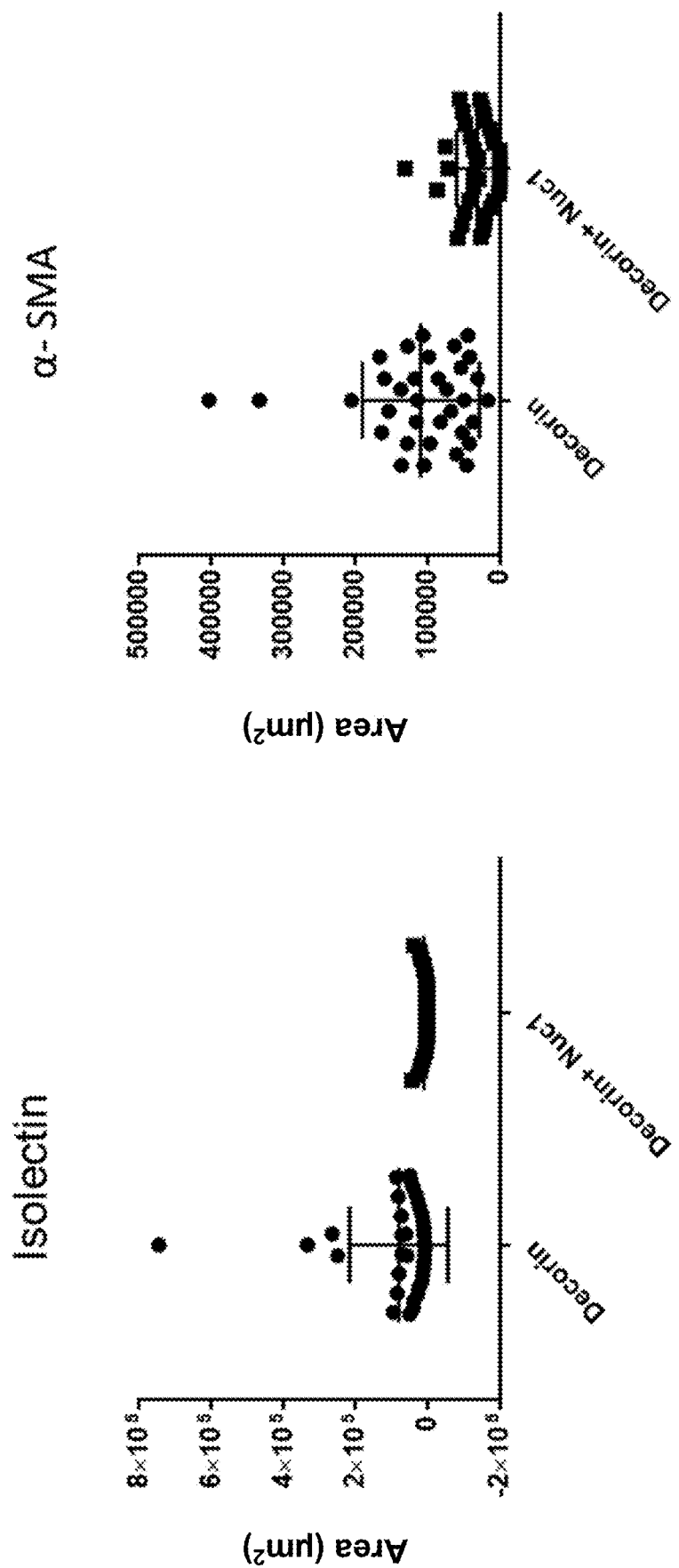

To test the ability of Nuc1 to assist in the penetration of decorin into the cornea for treatment of fibrosis, mice were anesthetized and alkali burn was induced in the cornea by applying 2 mm filter paper discs soaked with 1N Sodium Hydroxide (NaOH) on the central cornea of the right eye for 30 seconds. The filter paper was gently removed and the cornea was rinsed with phosphate buffered saline (PBS) 10 times. Topical application of PBS, decorin (0.5 µg), or decorin (0.5 µg)+Nuc1 (0.5 µg) was initiated 24 hours after exposure to NaOH. The treatments were applied topically once a day for seven days. After 7 days, mice were sacrificed by $CO_2$ inhalation. Eyes were enucleated and fixed in 4% paraformaldehyde. Corneal cryosections were taken using a Micron 550 cryostat and stained for α-actin, a marker of fibrosis. We found that whereas topical application of decorin alone reduced α-actin staining by 33.3% (p<0.025) relative to PBS, application of decorin+Nuc 1 resulted in a 46.2% (p<0.0028) reduction in α-actin staining relative to PBS, demonstrating that Nuc1 enhances the anti-fibrotic potency of decorin (FIG. 5A). Given these promising results, a more detailed study was subsequently conducted on the use of Nuc1 for delivery of decorin to the cornea for the purposes of treating angiogenesis, fibrosis and inflammation following chemical burn to the cornea (see Example 2).

Additionally, we examined whether Nuc1 could enhance the potency of decorin in mice with laser induced choroidal neovascularization (CNV), the murine model of wet AMD described in the previous section. Immediately following laser treatment, mice received an intravitreal injection of either 0.5 µg human recombinant decorin alone or in combination with Nuc1 peptide (0.5 µg), and eyes were harvested after seven days. The size of CNV growth was measured by staining the retinal pigment epithelium (RPE) with Griffonia Simplicifolia isolectin and fibrosis was measured by staining for α-actin (α-SMA, FIG. 5B). Using an unpaired T-test, we discovered a statistically significant reduction in the CNV area (isolectin, p<0.0072) and in fibrosis (α-SMA, p<0.0001) in the decorin and decorin+Nuc1 treated groups (FIG. 5C). Notably, there was an approximately 70 percent reduction in CNV and fibrosis in the presence of Nuc1, as compared to decorin alone, which strongly suggests that Nuc1 enhances the penetration and potency of decorin in ameliorating the impact of laser induced CNV and fibrosis.

Nuc1 Facilitates Delivery of Peptides and Small Molecules into the Retina

Figure 6:
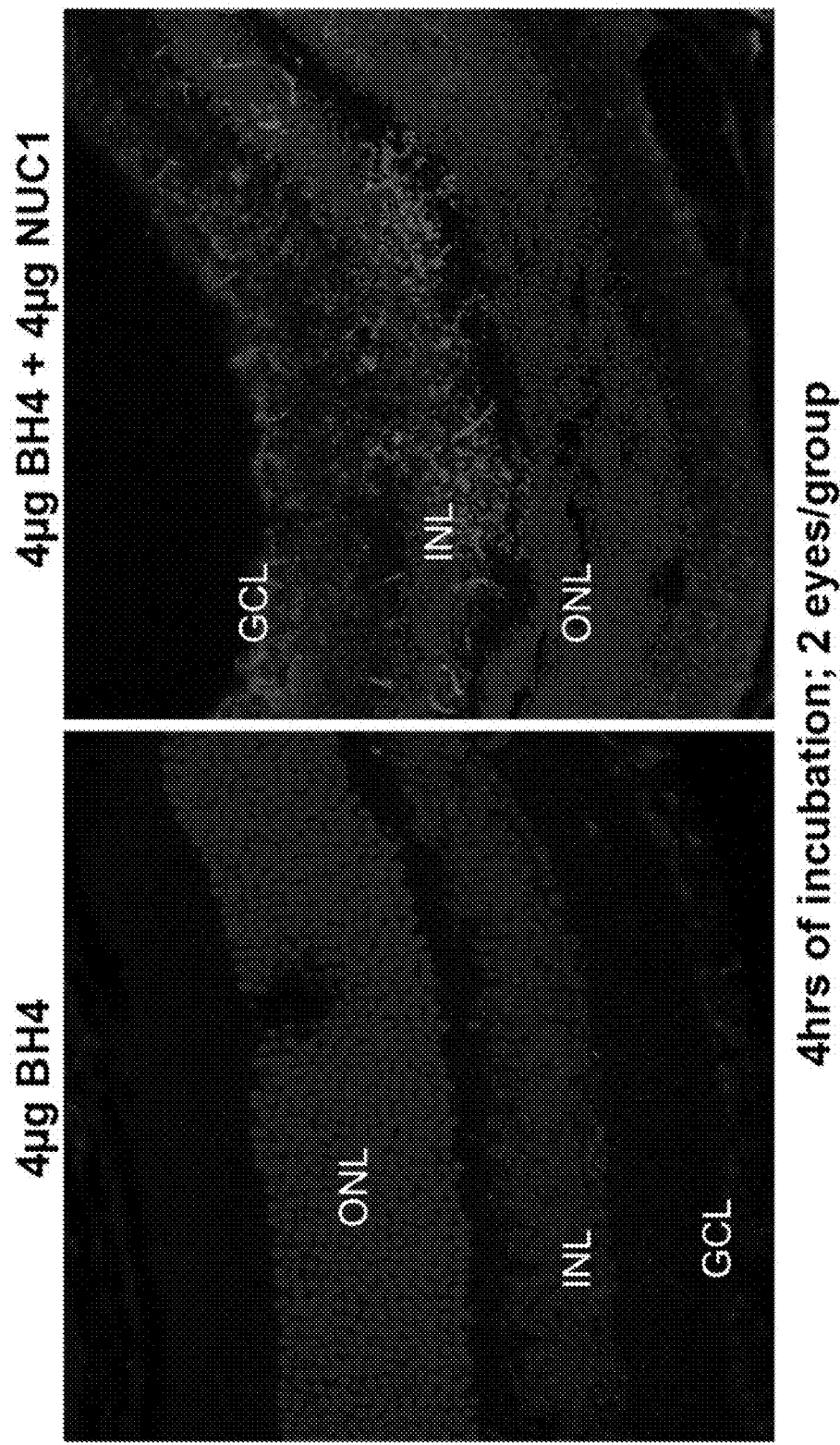
FIG. 6 demonstrates that Nuc1 facilitates delivery of small molecules into the retina. Whereas fluorescently labeled BH4 peptide does not penetrate the retina, BH4 co-injected intravitreally with Nuc1 does penetrate the retina (A). Nuc1 also significantly enhanced the penetration of fluorescently labeled dexamethasone (Dex-F1; B). Nuclei are stained by DAPI (blue). GCL: ganglion cell layer; ONL: outer nuclear layer; INL: inner nuclear layer.
Figure 6:
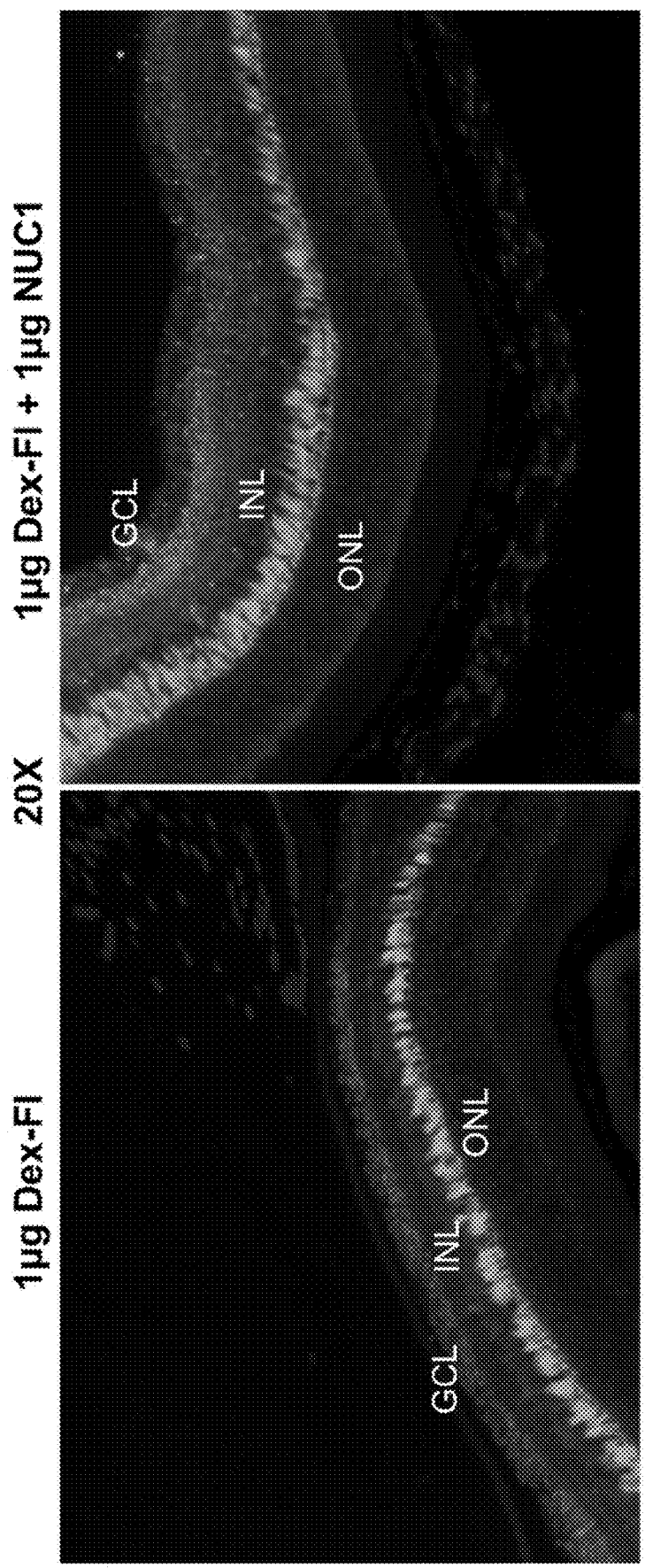

Molecules significantly smaller than whole proteins have the potential to act as therapeutic agents. For example, the BH4-domain peptide from Bc1-xL is known to have anti-apoptotic activity in vivo (Rong et al., 2009). However, BH4 does not appear to have any significant cell penetrating properties. Thus, several groups have delivered BH4 to cells by chemical linkage with the cell penetrating peptide TAT (Donnini et al., 2009; Hotchkiss et al., 2006; Park, 2011). To investigate whether Nuc1 can enhance the uptake of BH4 in the retina without the need for chemical linkage, we injected 6 week old C57BU6J mice intravitreally with 4 µg fluorescently labeled BH4 peptide only or 4 µg labeled BH4 peptide in combination with 4 µg Nuc1. While the BH4 peptide by itself had limited uptake into the retina, when BH4 was combined with Nuc 1, there was a significant qualitative increase in uptake of fluorescently labeled BH4 peptide (FIG. 6A).

Small molecules including steroids can serve as an anti-inflammatory agents. However, steroids such as dexamethasone have significant side effects when injected into the vitreous, including the formation of cataracts or the induction of an increase in intraocular pressure (Phulke et al., 2017; Pleyer et al., 2013; Zhang et al., 2018). We hypothesized that Nuc1 may facilitate penetration of steroids into tissues, enabling a steroid to be applied in a reduced dosage without loss of efficacy. To test this hypothesis, we injected either 1 µg fluorescently labeled dexamethasone alone or fluorescently labeled dexamethasone in combination with 1 µg Nuc1. We found that both dexamethasone alone and dexamethasone with Nuc1 were taken up into the retina. However, uptake of dexamethasone was qualitatively greater when it was co-injected with Nuc1 (FIG. 6B).

Nuc 1 Enhances Viral Infection of Retinal Cells In Vivo

Figure 7:
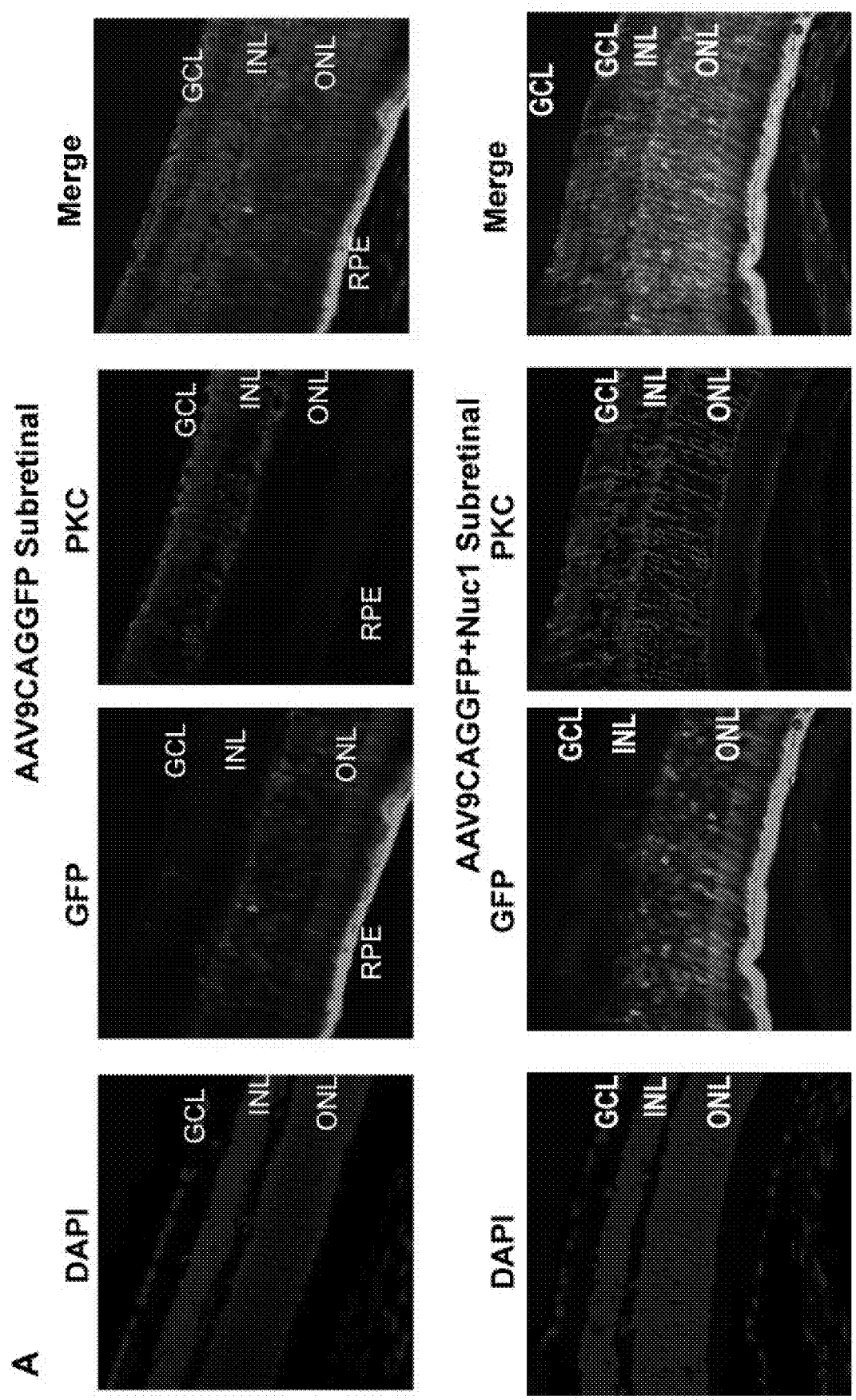
FIG. 7 demonstrates that Nuc 1 enhances adeno-associated virus infection of retinal cells in vivo. Nuc1 enhanced the delivery of AAV9 following subretinal injection (A) or intravitreal injection (B). Enhancement of infection was non uniform across the retina as measured by fundus photography (C). Frozen sections were co stained for bipolar cells (PKC). Nuclei were stained with DAPI (blue). GCL: ganglion cell layer; ONL: outer nuclear layer; INL: inner nuclear layer.
Figure 7:
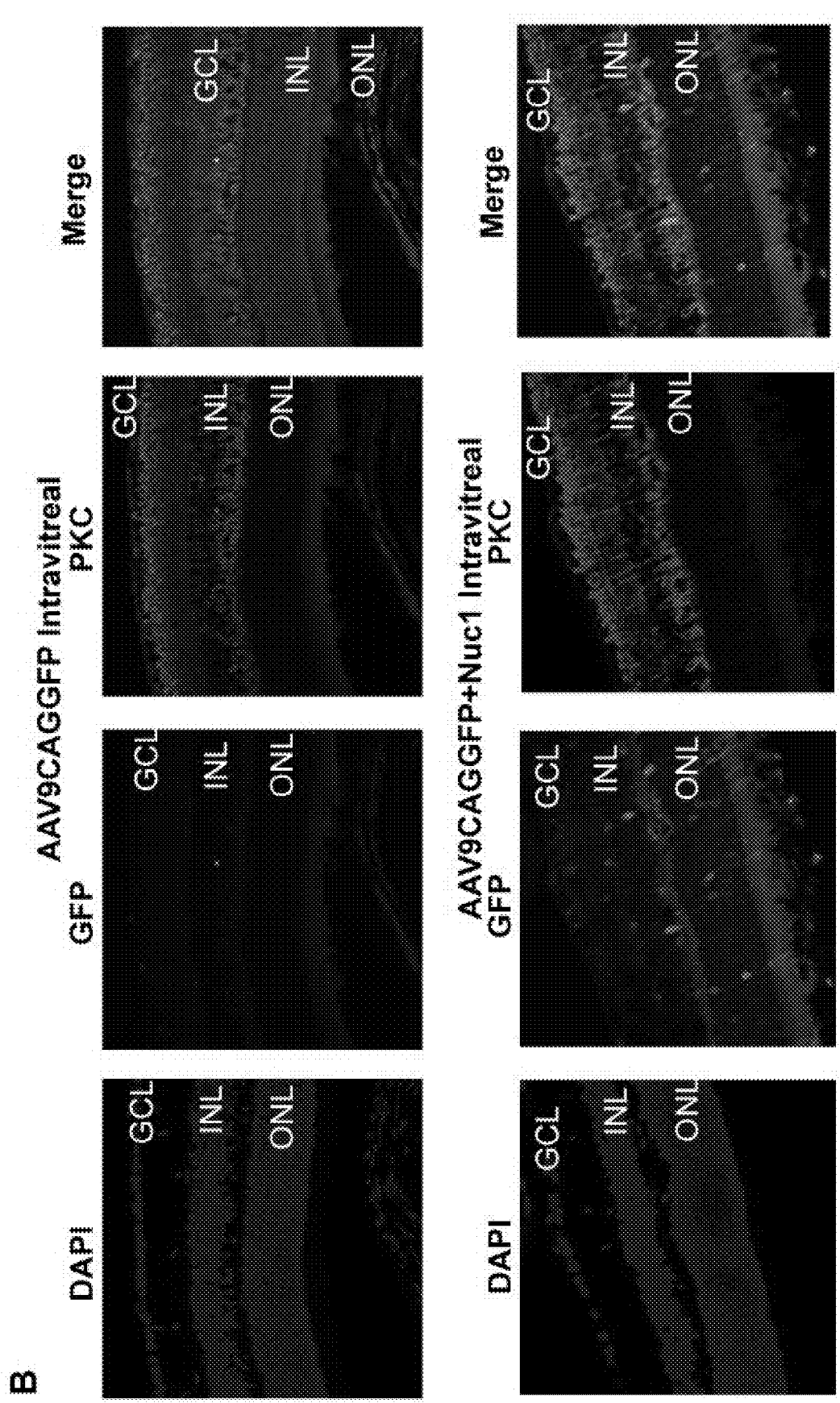
Figure 7:
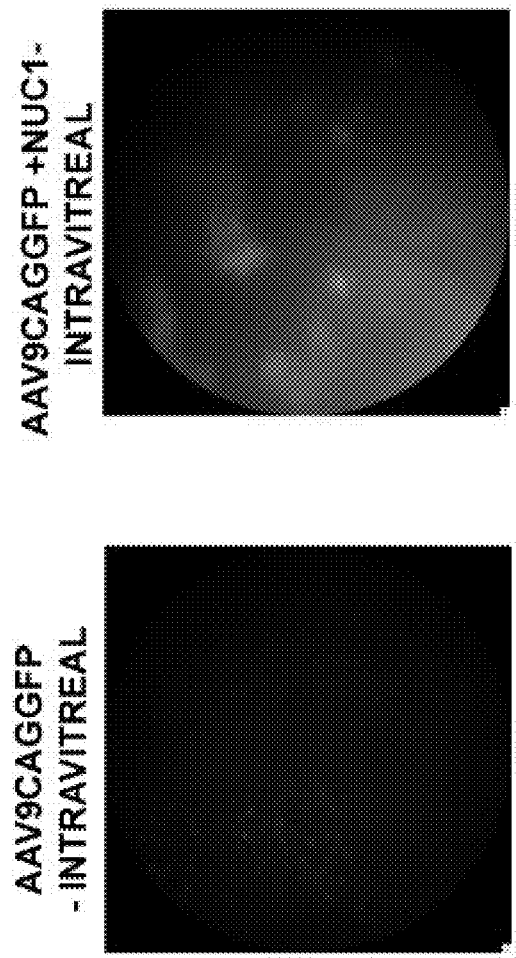

Recombinant viruses, such as adeno-associated virus (AAV), are excellent vehicles for delivery of recombinant genes to the retina (Bennett, 2017). However, high titers of virus are generally needed to achieve transduction of cells at levels that are 'therapeutic'. Despite the immune sequestered nature of the subretinal and intravitreal chamber, immune responses to recombinant AAV have been well documented in these regions (Boyd et al., 2016; Kotterman et al., 2015; Reichel et al., 2017). Lower doses of virus generally produce lesser immune responses. To determine whether Nuc1 can enhance the potency of AAV infection and consequently reduce the need for high(er) doses of virus, we injected a recombinant AAV serotype 2 (pseudotyped with AAV 9 capsid; AAV2/9) expressing GFP (AAV-CAG-GFP) into the eyes of adult C57/B16J mice. As anticipated, subretinal delivery of AAV-CAG-GFP enabled transgene (GFP) expression in the retinal pigment epithelium (RPE) and photoreceptors (FIG. 7A). Surprisingly, when AAV2/9 was co-injected with 1 µg Nuc1, transgene expression was qualitatively superior to AAV2/9 injected by itself (FIG. 7A).

In contrast, AAV2/9 did not infect the inner or outer retina when injected intravitreally (FIG. 7B). However, we found that 1 µg Nuc1 added to the AAV-CAG-GFP suspension enhanced infectivity of the inner and outer retina, including the ONL (FIG. 7B). This improvement in infection was variable across the retina, occurring in patches as observable by fundus photography (FIG. 7C) of live animals. Quantitation of viral infections was performed by RT-PCR (see below).

Figure 8:
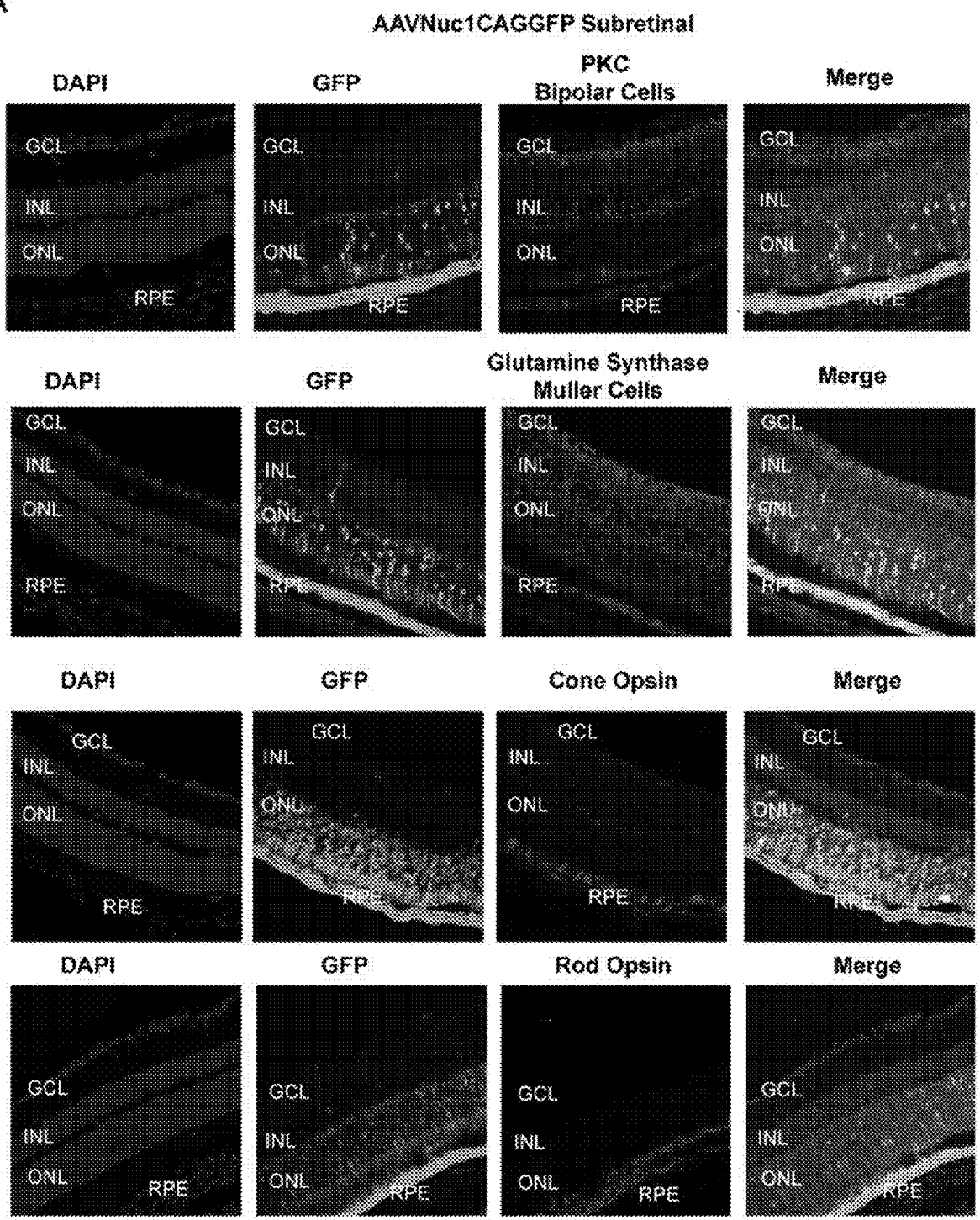
FIG. 8 demonstrates that incorporation of Nuc1 into the AAV capsid does not significantly enhance infection. Subretinal injection of AAV-Nuc1-CAG-GFP did not lead to a significant enhancement of GFP expression relative to AAV-CAG-GFP (A). Furthermore, this vector did not penetrate the retina following intravitreal injection (B). In contrast AAV-Nuc1-CAG-GFP could penetrate the retina when co-injected with Nuc1 (C). Nuclei were stained with DAPI (blue). GCL: ganglion cell layer; ONL: outer nuclear layer; INL: inner nuclear layer.
Figure 8:
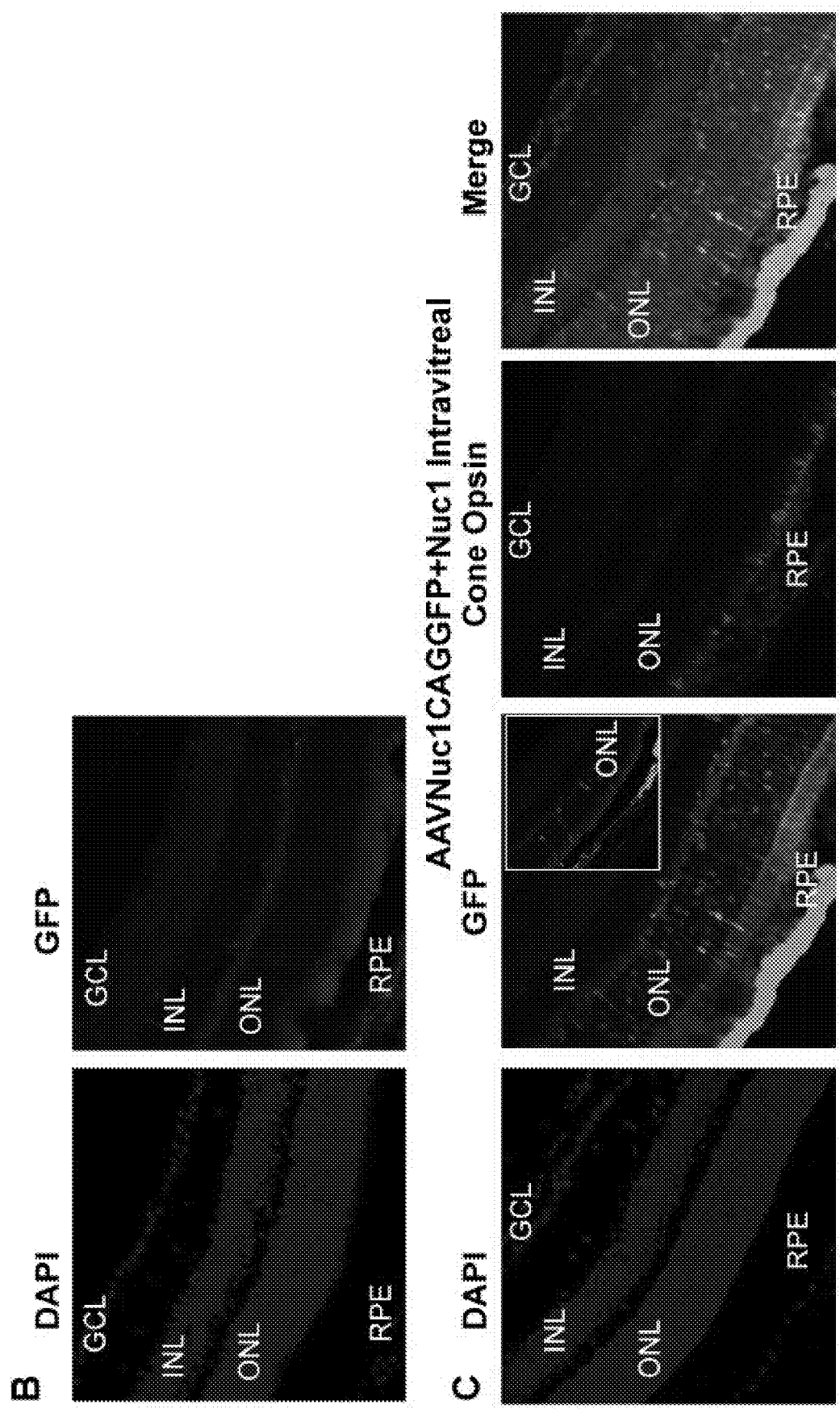
Figure 9:
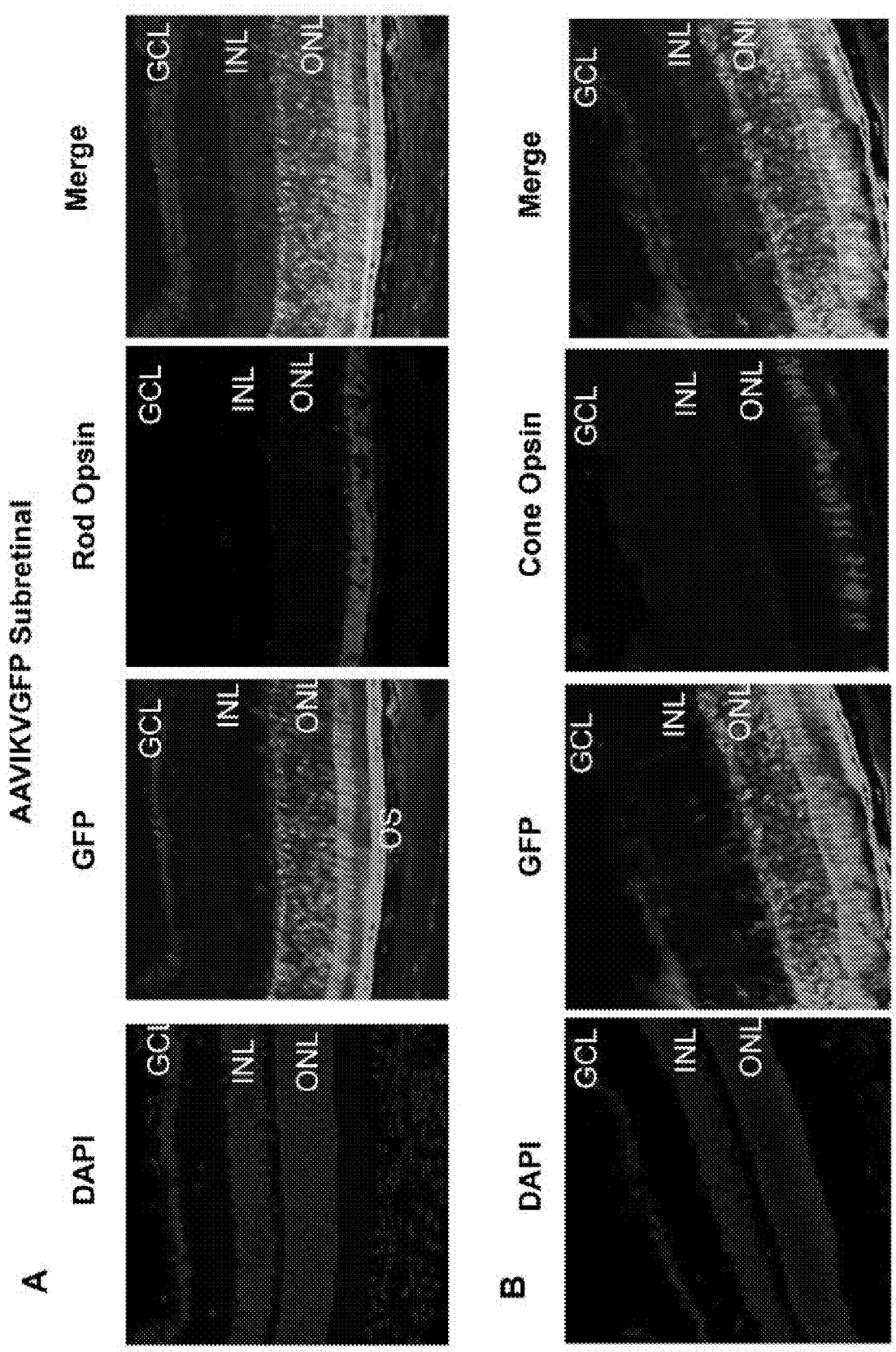
FIG. 9 shows the results of AAV-IKV-GFP infection following subretinal injection. AAV-IKV-GFP leads to significant infection of photoreceptors following subretinal injection. Sections were co-stained with rod opsin (A), cone opsin (B), gluatamine synthase (C), PKC (D). GCL, ganglion cell layer; ONL, outer nuclear layer. For some panels higher magnification images are also presented.
Figure 9:
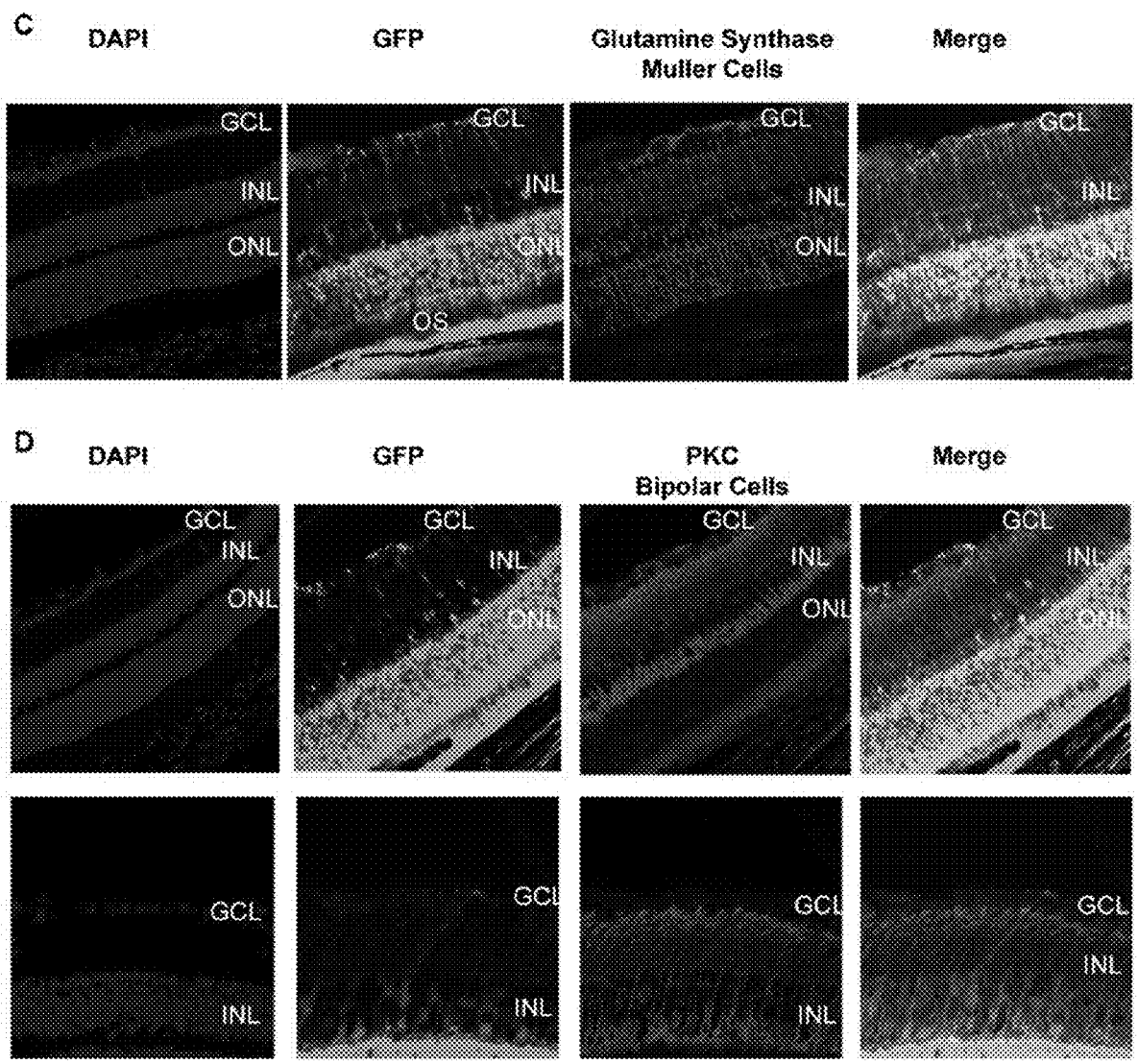

Incorporation of Nuc1 into the AAV Capsid does not Significantly Enhance Infection To determine whether AAV2/9 would be more effective if the Nuc1 sequence were incorporated into the coat of the AAV capsid, obviating the need for an external peptide, we generated a recombinant AAV2/9 expressing GFP that contained the Nuc1 sequence (flanked at each end by a glycine) in the VP1 capsid of AAV9. The Nuc1 sequence was inserted between amino acids 588 and 589 as defined in (Khabou et al., 2016); generating AAV-Nuc1-CAG-GFP. This modification did not lead to a significant enhancement in infectivity of virus by the subretinal route relative to AAV-CAG-GFP (FIG. 8A). Furthermore, AAV-Nuc1-CAG-GFP did not infect the inner or outer retina following intravitreal injection (FIG. 8B). However, infection of AAV-Nuc1-CAG-GFP could be enhanced when it was co-injected with Nuc1 peptide via the intravitreal route (FIG. 8C), but this result was highly variable, as some retinas examined had very limited expression of GFP in the outer retina (FIG. 8C, GFP inset). One possible explanation for this result is competition between the Nuc1 peptide and the Nuc1 sequence in the viral capsid. Indeed, larger amounts of Nuc1 led to a reduction in overall AAV-Nuc1-CAG-GFP infectivity (data not shown).

Retinal Penetrating AAV

To determine whether the heparan sulphate binding region of VEGFA165 in Nuc1 was interfering with viral infectivity, we generated a version of AAV-Nuc1-CAG-GFP that had the heparan sulphate binding sequence deleted, such that the virus now contained the partial sequence ASIKVAVSA (SEQ ID NO: 4) from laminin-1. This shorter sequence was flanked at each end by a glycine residue, forming the sequence GASIKVAVSAG (SEQ ID NO: 6), and was similarly cloned between amino acids 588 and 589 of the AAV capsid, as described above, to form a virus referred to as AAV-IKV-GFP. We found that AAV-IKV-GFP injected subretinally into 6 week-old C57BL/6J mice had significantly improved infection of retinal cells (FIG. 9A-9D). Counter staining of AAV-IKV-GFP infected retinal sections with rod opsin (FIG. 9A), cone opsin (FIG. 9B), glutamine synthase (FIG. 9C), PKC (FIG. 9D) revealed that AAV-IKV-GFP infected rod cells, cone cells, Muller cells and bipolar cells respectively.

Figure 10:
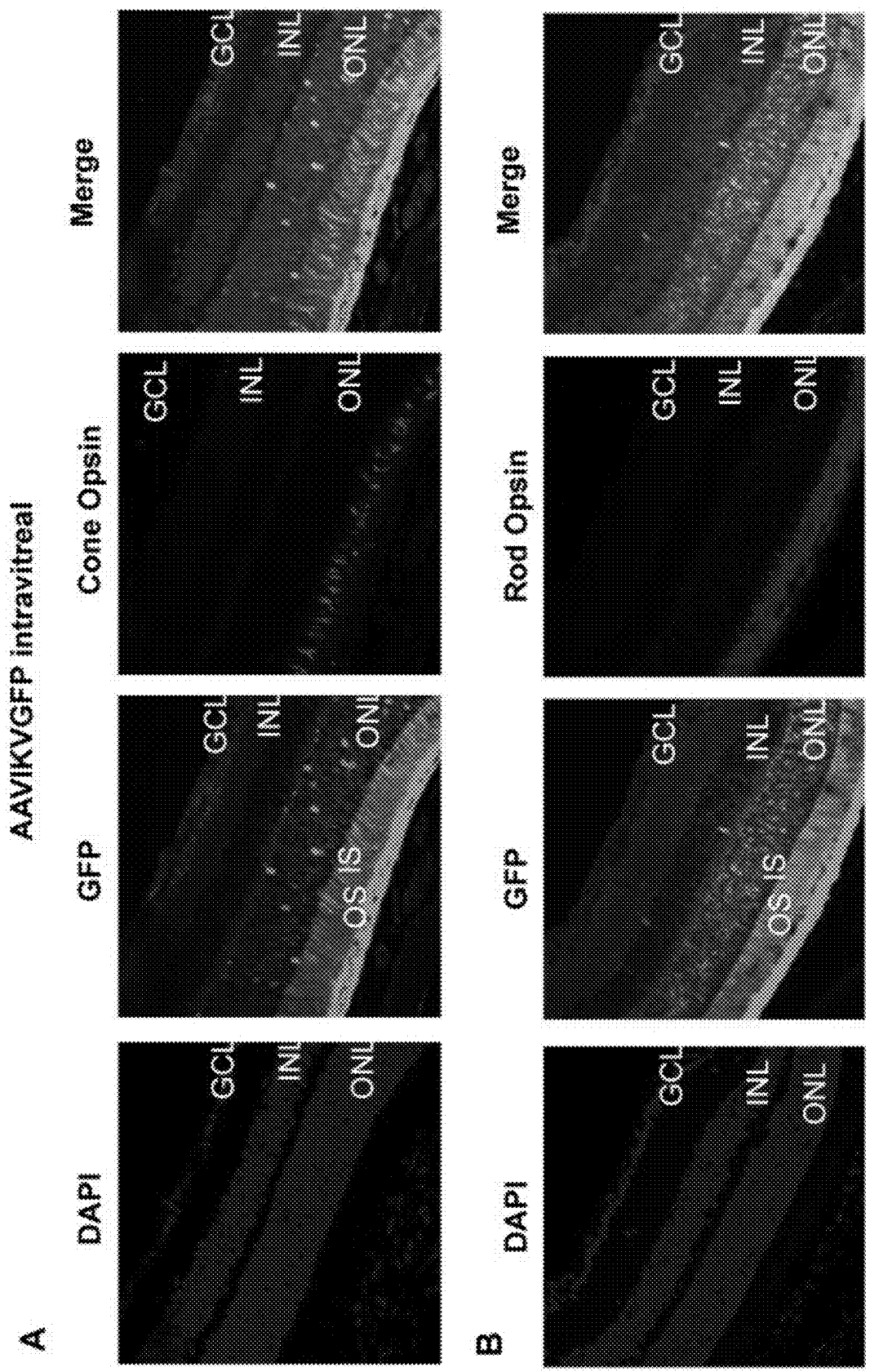
FIG. 10 shows the results of AAV-IKV-GFP infection following intravitreal injection. AAV-IKV-GFP leads to significant infection of a variety of retinal cells following intravitreal injection. Sections were co-stained with cone opsin (A), rod opsin (B), PKC/bipolar cells (C) tubulin (D) or gluatamine synthase (E). GCL, ganglion cell layer; ONL, outer nuclear layer. For some panels higher magnification images are also presented. Whereas the pattern of expression presented in panels A-D was consistently observed; the pattern presented in panel E was found infrequently.
Figure 10:
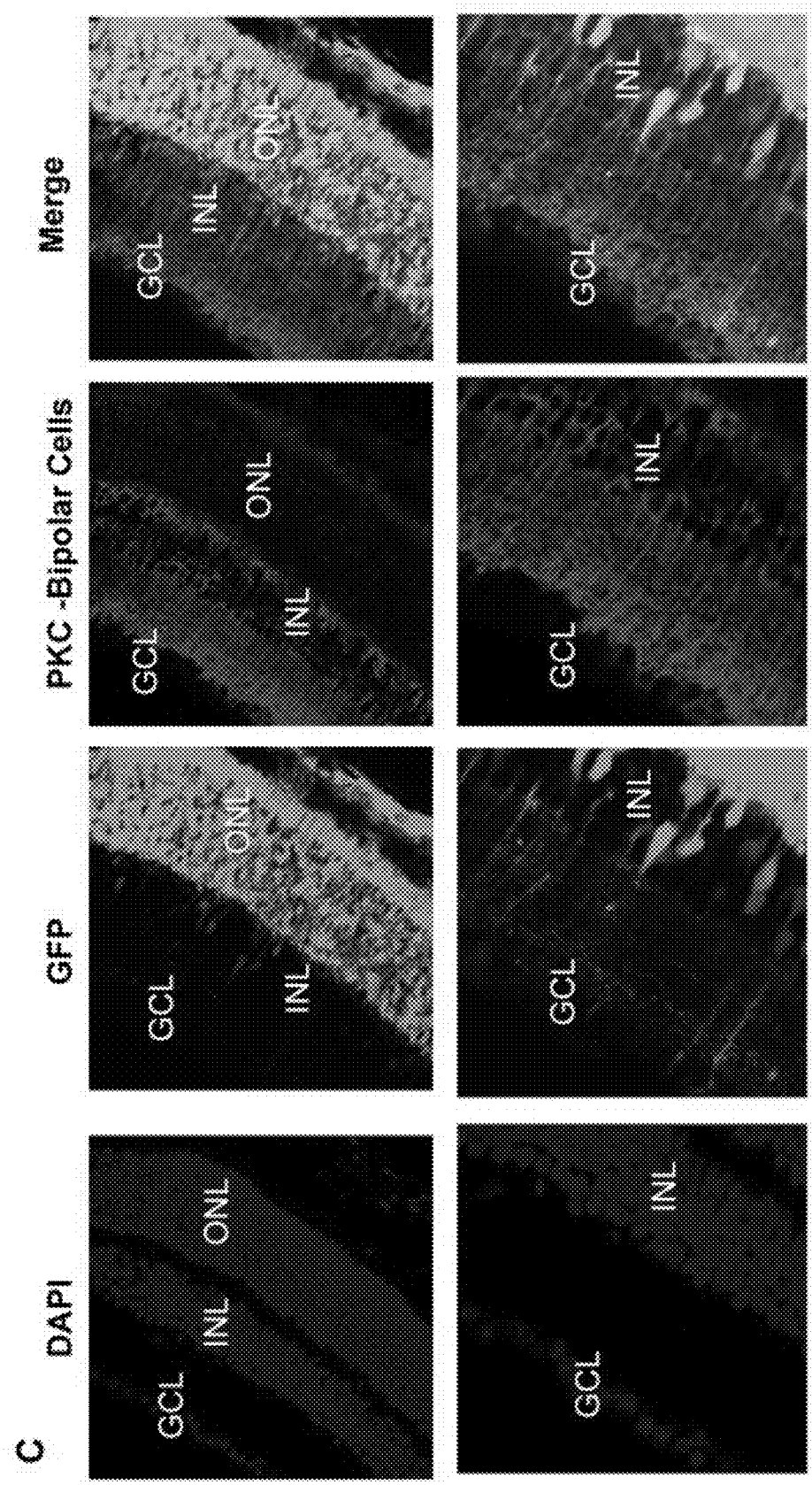
Figure 10:
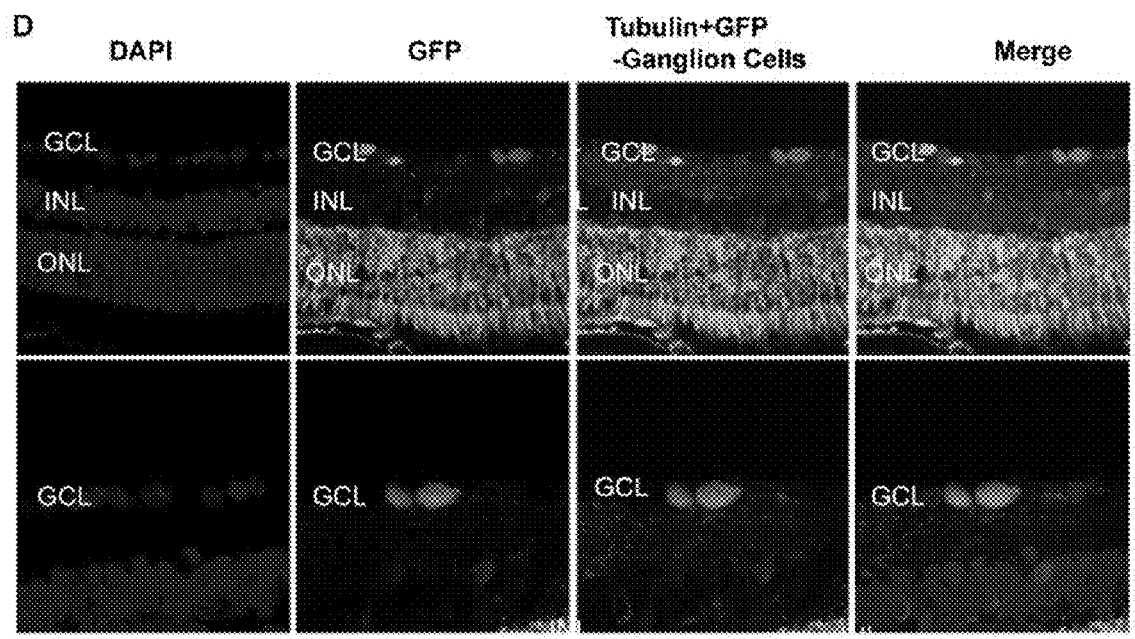
Figure 10:
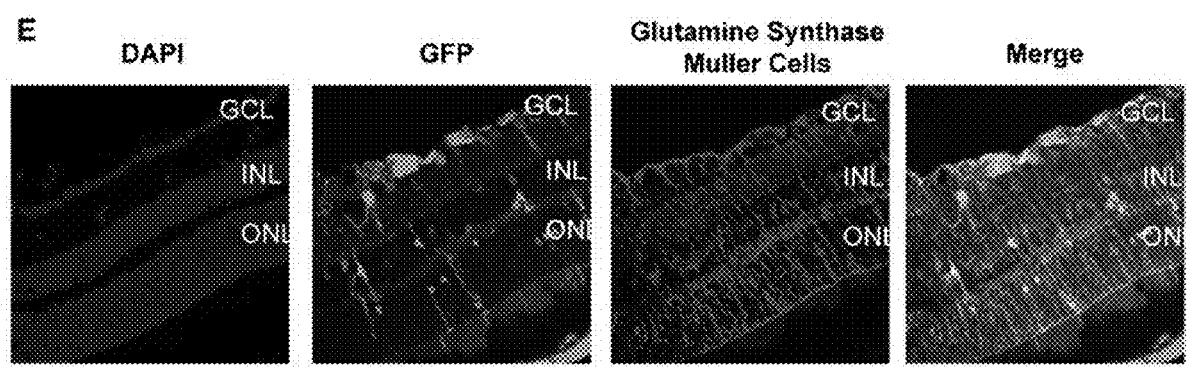

Surprisingly, when AAV-IKV-GFP was injected intravitreally into 6 week-old C57BL/6J mice and sections counter stained with cone opsin (FIG. 10A), rod opsin (FIG. 10B), PKC (FIG. 10C) or Tubulin (FIG. 10D) revealed that AAV-IKV-GFP infected cone photoreceptors, rod photoreceptors, bipolar cells and ganglion cells respectively. In some retina, Muller cells were also observed to be positive in some areas based on co-staining with glutamine synthase (FIG. 10E).

Figure 11:
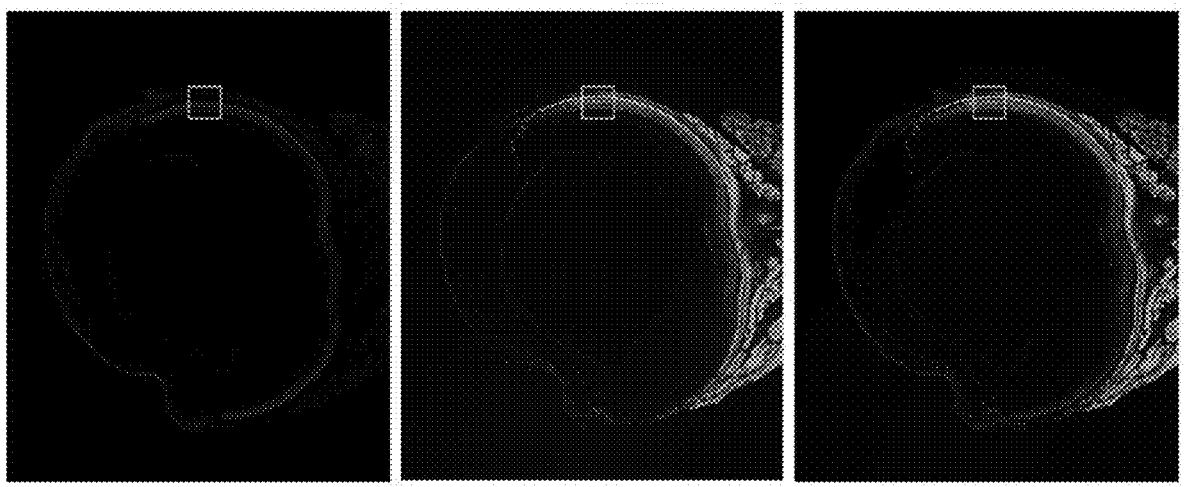
FIG. 11 demonstrates that maximum transgene expression is achieved when AAV-IKV is co-injected with Nuc1. Co-injection of AAV-IKV-GFP with Nuc1 led to maximum transgene expression following intravitreal injection, occurring over the entire retinal surface (A). Higher magnification images (B) indicated that photoreceptors were highly GFP-positive, including the retinal pigment epithelium and choroid. Fundus imaging of live animals also revealed that transgene expression occurred across the entire retinal surface (C). Higher exposure of inner retina revealed GFP-positive inner plexiform layer (IPL) and ganglion cell layer (GCL), including some Muller cells (D). Long exposure images of retinal sections revealed that cells in the inner nuclear layer (INL) were also positive, co-stained with PCK for bipolar cells (E). Relative to AAV-CAG-GFP, co-injection of Nuc1 enhanced mRNA levels by approximately 4.3 fold. Nuc1 also enhanced expression of AAV-IKV-GFP approximately 8.5 fold. Relative to AAV-GFP, IKV-GFP+Nuc1 had approximately 300 fold greater amounts of mRNA (F).
Figure 11:
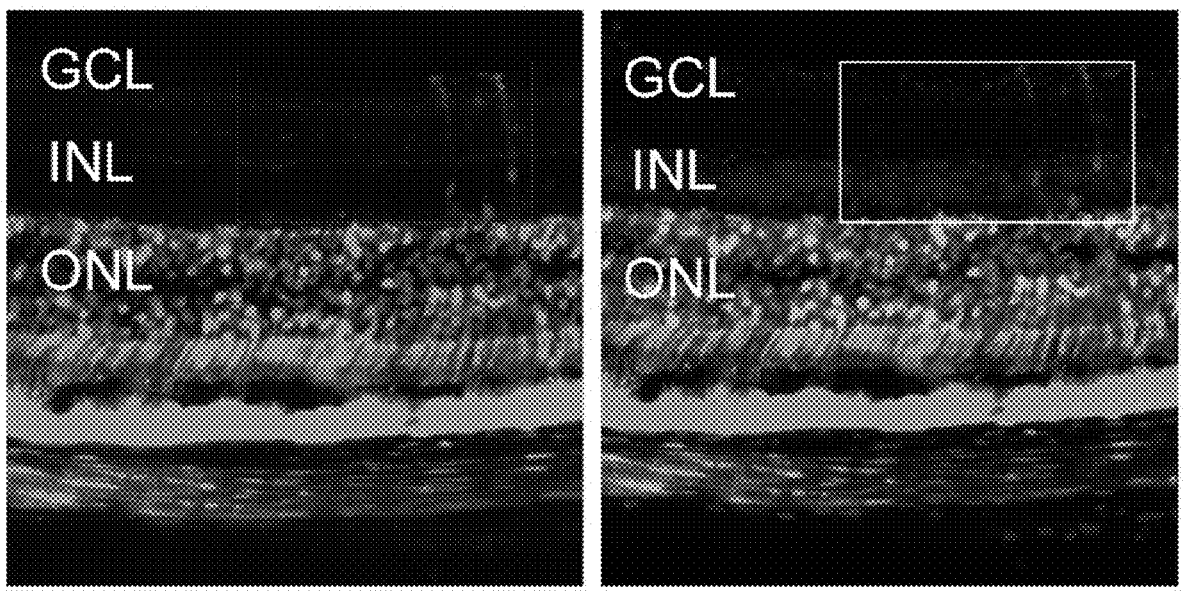
Figure 11:
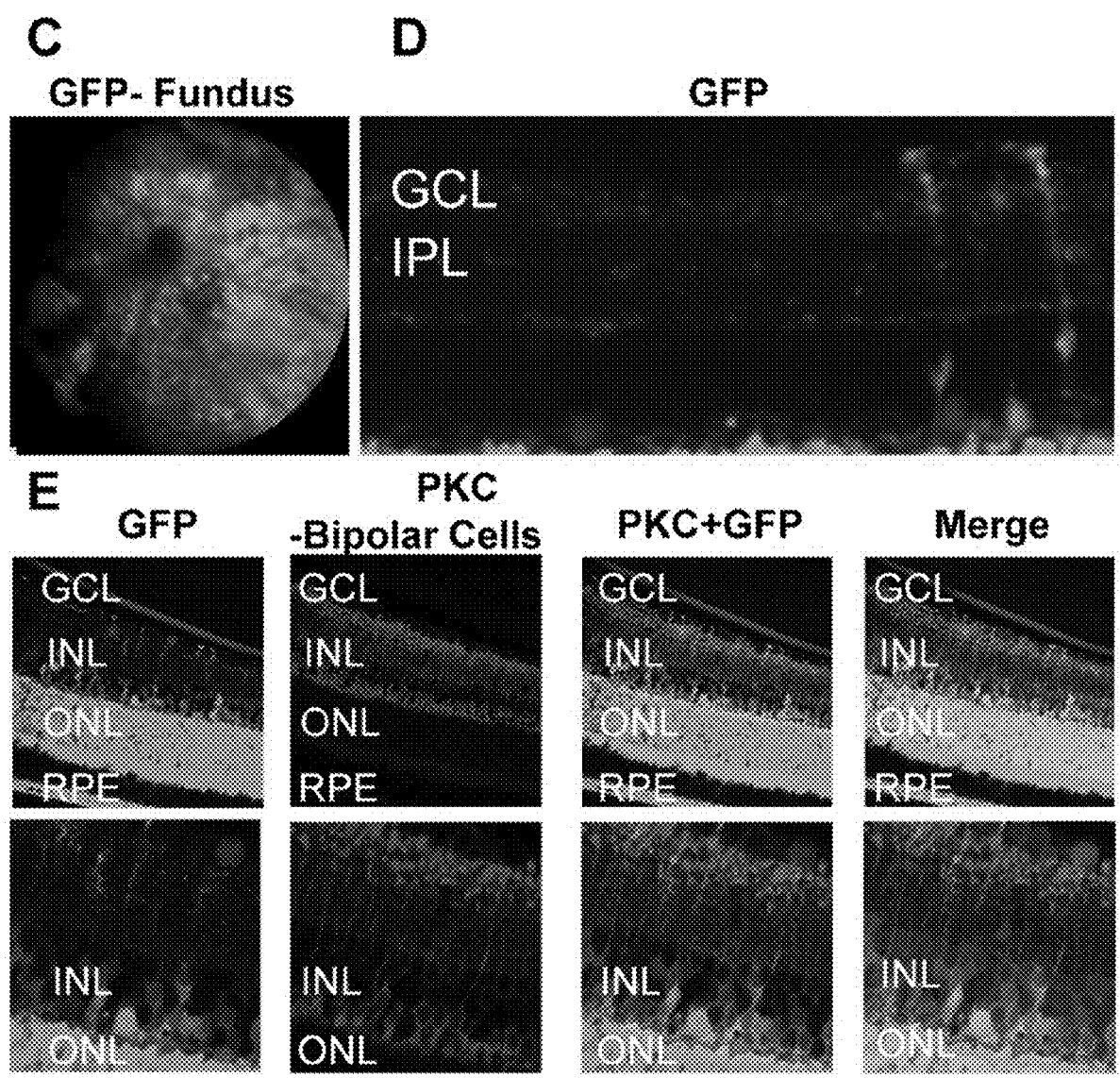
Figure 11:
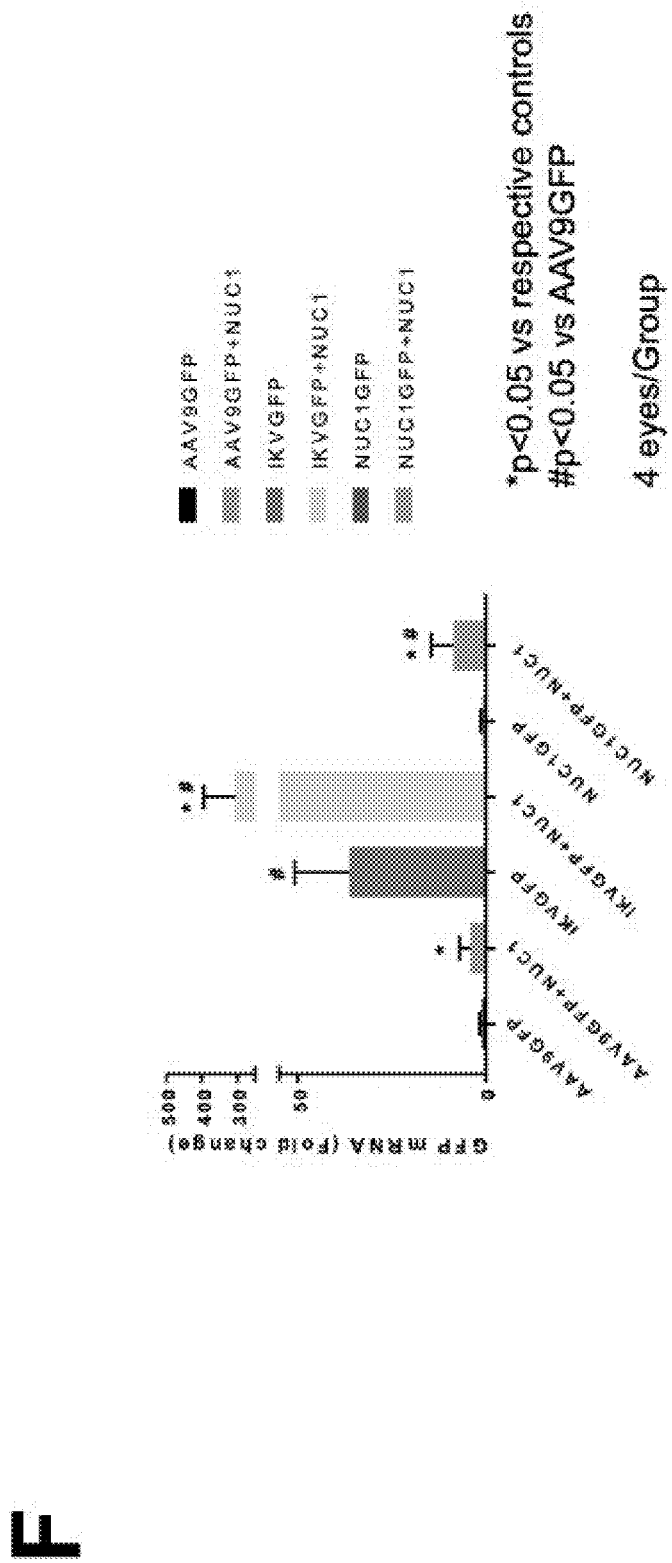

We next considered whether intravitreal injection of AAV-IKV-GFP could be further enhanced by co-administration with Nuc1. Our studies above suggested that a complete Nuc1 sequence incorporated into the viral capsid was inhibited when co-administered with Nuc1 peptide, possibly due to competition for cell entry. With a reduced Nuc1 sequence incorporated into the capsid, we found that AAV-IKV-GFP injected intravitreally had the most potent infection of retinal observed thus far, with robust expression throughout the retina (FIG. 11A). Closer examination of boxed region in FIG. 11A revealed that a high density of photoreceptors, RPE and surprisingly the choroid were GFP positive (FIG. 11B). This pattern of GFP expression was not limited to a specific region as fundus photography of live animals revealed GFP across a significant field of the retina (FIG. 11C). Furthermore, longer exposure of boxed region in FIG. 11B revealed that the inner plexiform layer (IPL) and ganglion cell layer (GCL) were also GFP positive, albeit significantly less than the ONL or the RPE (FIG. 11D). Counter staining with PKC for bipolar cells revealed an abundant number of bipolar cells that were GFP positive in addition to ONL and RPE (FIG. 11E).

To measure mRNA levels expressed from the various virus constructs injected intravitreally, we performed quantitative RT-PCR on retinal tissues. We found that Nuc1 significantly enhanced the levels of mRNA expression from each virus tested. Relative to levels expressed from AAV-CAG-GFP alone, co-injection of Nuc1 enhanced mRNA levels by approximately 4.3 fold. Nuc1 also enhanced expression of AAV-IKV-GFP approximately 8.5 fold. (FIG. 11F). Relative to AAV-GFP, AAV-IKV-GFP+Nuc1 had approximately 300 fold greater mRNA levels. Thus, Nuc1 enhanced infection of recombinant AAV and when combined with incorporation of a partial Nuc1 sequence in the AAV capsid, we observed the greatest relative increase in infection via the intravitreal route.

Inhibition of Oxidative Stress in the Outer Retina Via Intravitreal AAV Delivery NRF2 (nuclear factor erythroid 2 p45-related factor 2) is a master transcription factor that regulates the expression of antioxidant proteins that protect against oxidative damage triggered by injury and inflammation. Over 250 genes are targeted by NRF2. In a state of homeostasis, NRF2 is sequestered in the cytoplasm by Kelch like ECH-associated protein 1 (KEAP1) and Cullin 3, that degrade NRF2 by ubiquitination. Oxidative stress disrupts ubiquitination and NRF2 subsequently translocates to the nucleus and binds to the antioxidant response element (ARE) in the upstream promoter region of many antioxidative genes, initiating their transcription. Expression of NRF2 has been previously found to be therapeutic in various animal models of retinal degeneration, including AMD, retinitis pigmentosa, glaucoma, uveitis and diabetic retinopathy; as well as in many diseases of ageing including Alzheimer's disease, amyotrophic lateral sclerosis and Friedrich's ataxia.

Figure 12:
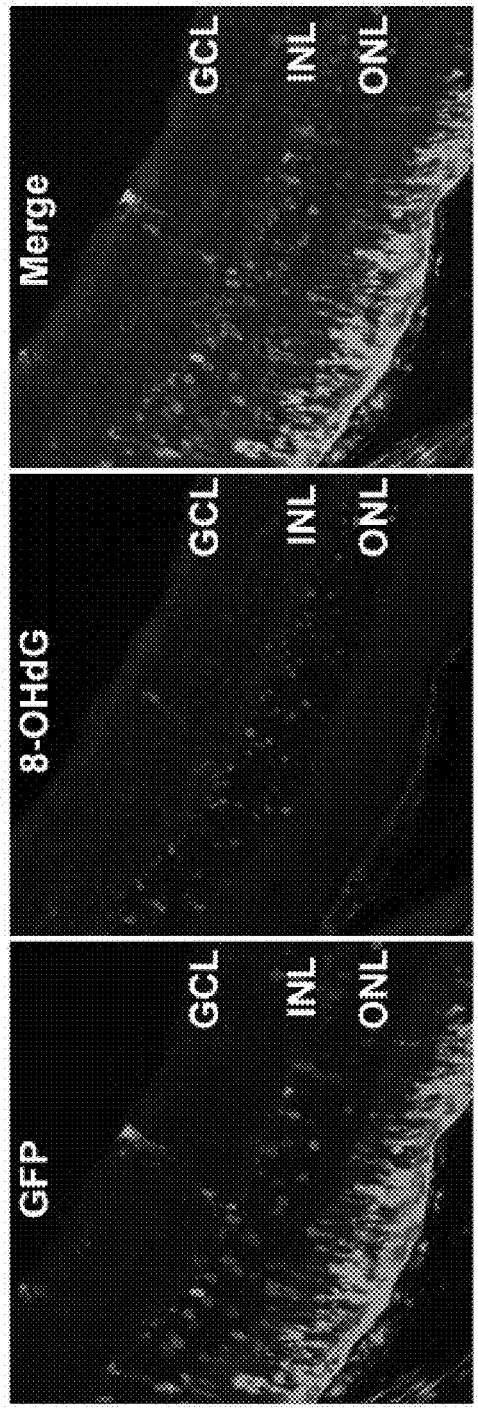
FIG. 12 demonstrates that intravitreal AAV delivery inhibits oxidative stress in the outer retina. AAV-IKV-Nrf2 injected C57/B16J mouse eyes exhibited significantly less 8-OHdG staining relative to AAV-IKV-GFP eyes (A). Similarly, AAV-IKV-Nrf2 injected NRF2 knockout mice exhibited significantly less 8-OHdG staining relative to AAV-IKV-GFP eyes (B). Quantitation of these retinas demonstrated a significant reduction in 8-OHdG staining in the ONL (C).
Figure 12:
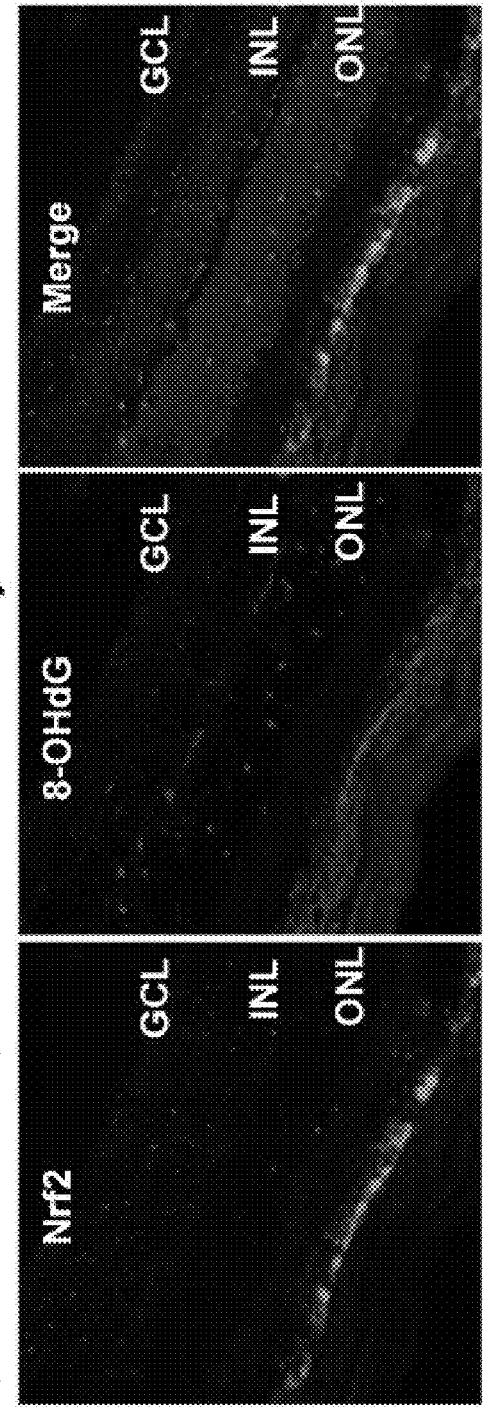
Figure 12:
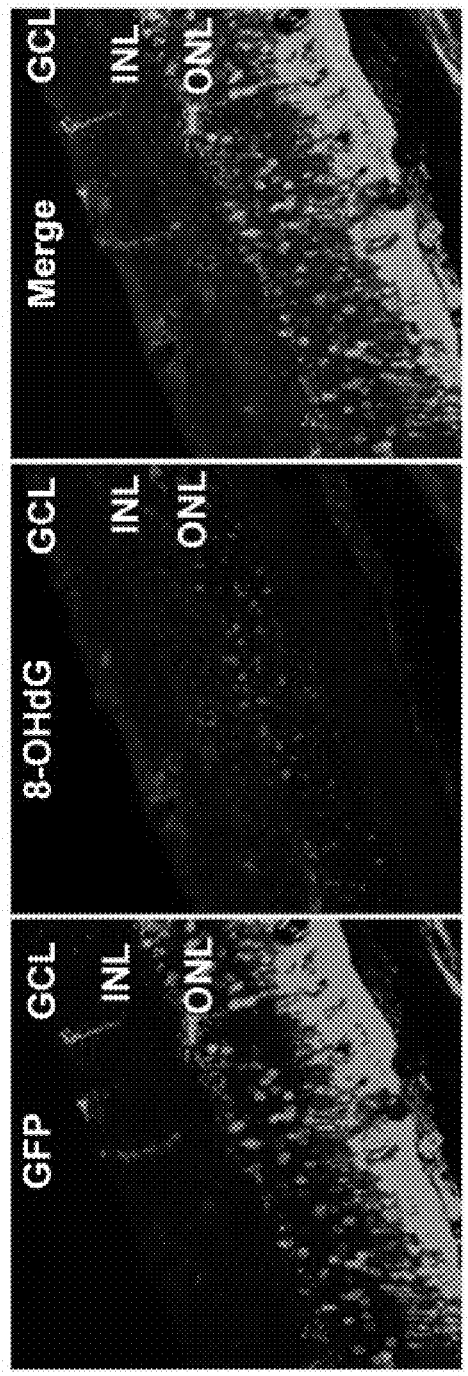
Figure 12:
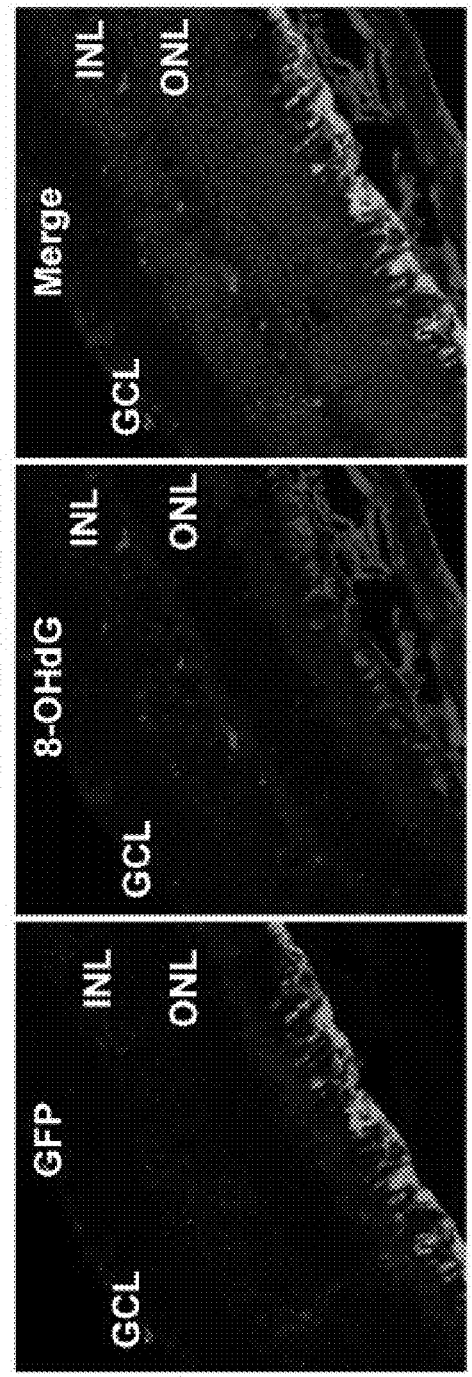
Figure 12:
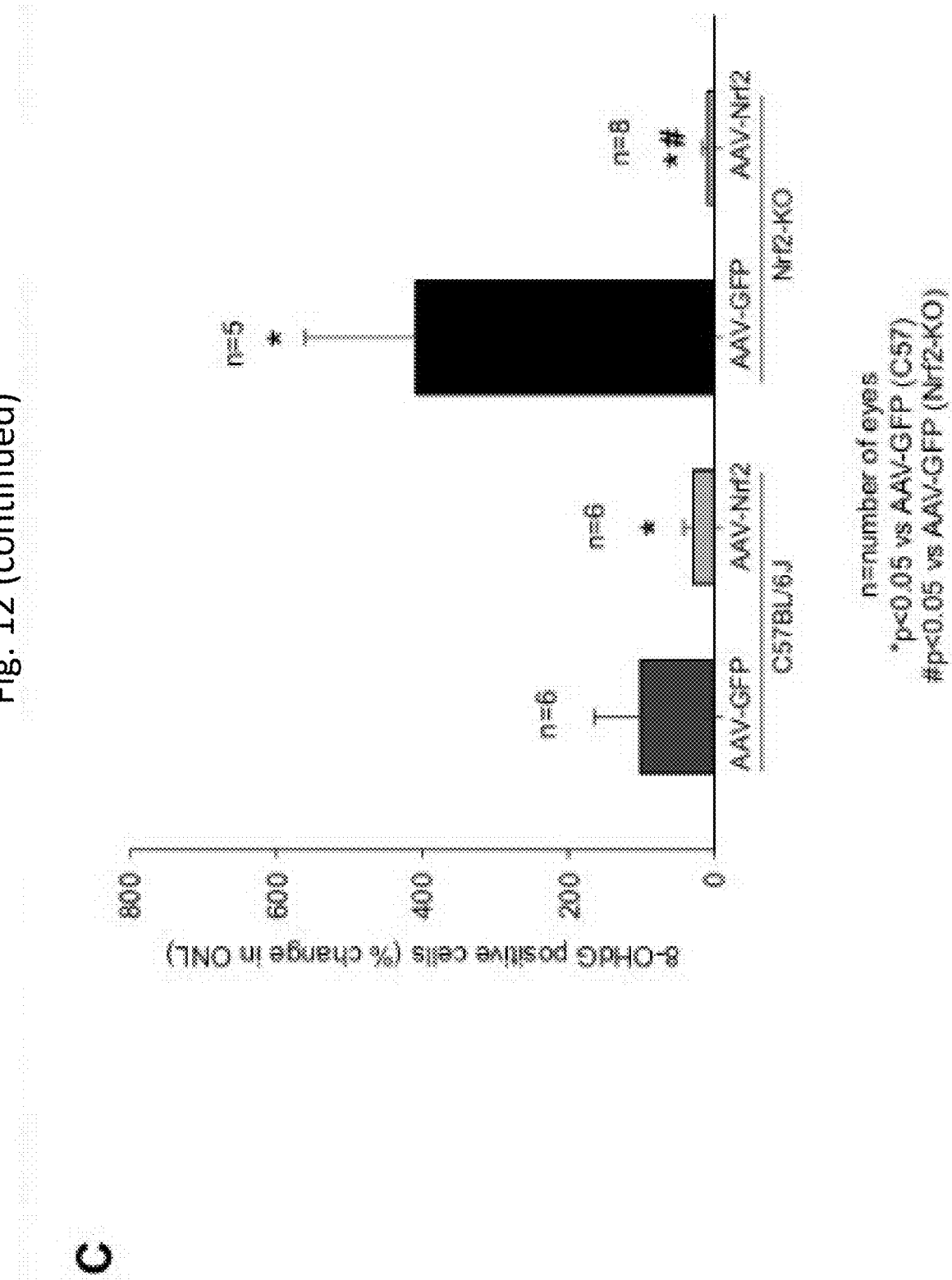

Intraperitoneal injection of MNU leads to significant oxidative stress in the retina. In nuclear and mitochondrial DNA, 8-hydroxy-2-deoxyguanosine (8-OHdG) is one of the predominant forms of free radical-induced oxidative lesions, and thus this marker has been widely used as a biomarker for oxidative stress. We wished to determine whether an AAV-IKV backbone in combination with Nuc1 could deliver a human Nrf2 transgene via the intravitreal route to the murine outer retina and inhibit MNU-induced oxidative stress. To test this hypothesis, adult C57B1/6J mice were injected intravitreally with AAV-IKV-Nrf2 (plus Nuc1) or AAV-IKV-GFP (plus Nuc1) as a negative control. After three weeks of transgene expression, mice were injected with 50 mg/kg MNU. Eyes were harvested 24 hours later and processed as described above and stained for the presence of 8-OHdG, GFP or Nrf2. We found that AAV-IKV-Nrf2 injected C57/B16J eyes exhibited significantly less 8-OHdG staining relative to AAV-IKV-GFP eyes (FIG. 12A). Similarly, AAVIKV-Nrf2 injected NRF2 knockout (NRF2−/−) mice exhibited significantly less 8-OHdG staining relative to AAV-IKV-GFP eyes (FIG. 12B). Quantitation of these retinas confirmed that there was a significant reduction in 8-OHdG staining in the ONL (FIG. 12C).

Figure 13:
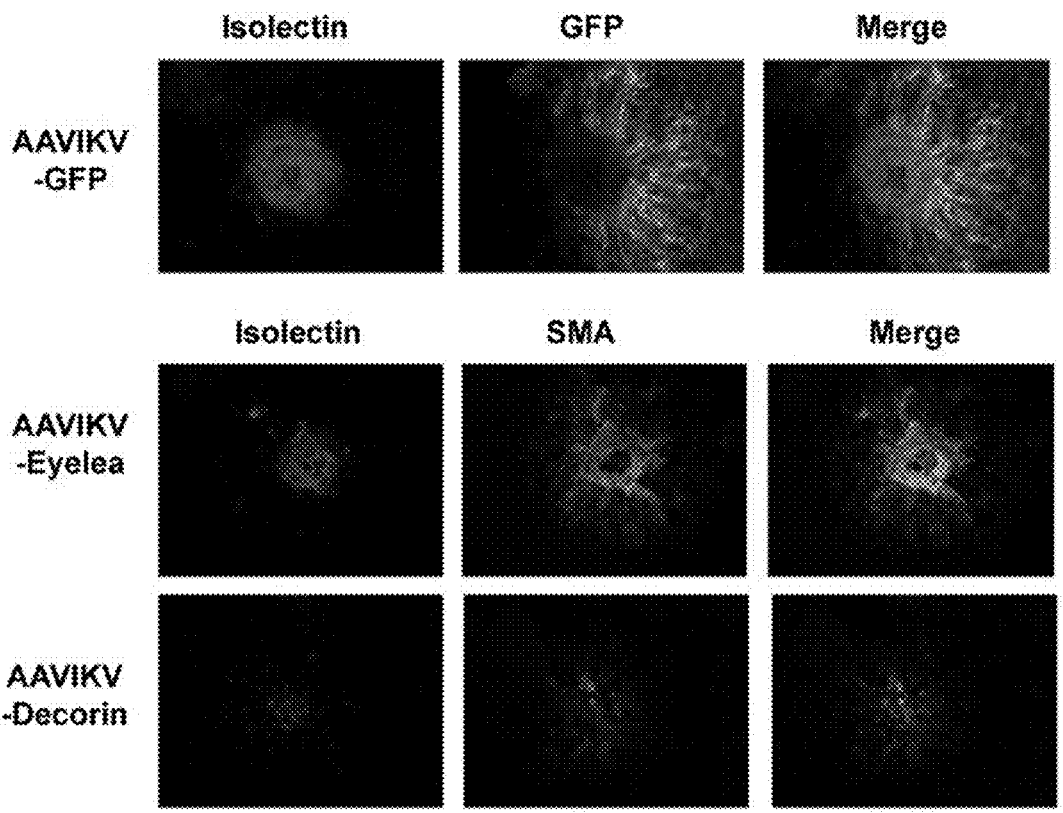
FIG. 13 demonstrates that intravitreal AAV delivery inhibits choroidal neovascularization and fibrosis in the outer retina. AAV-IKV-Decorin was found to be significantly superior to AAV-IKV-Eyelea or AAV-IKV-GFP in terms of efficacy for neovascularization and fibrosis in laser induced choroidal neovascularization (CNV) as measured by isolectin and smooth muscle actin (SMA) staining, respectively.
Figure 13:
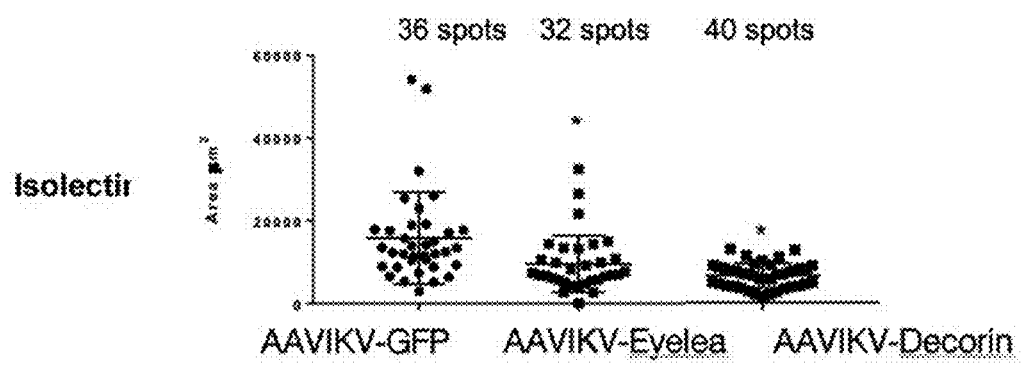
Figure 13:
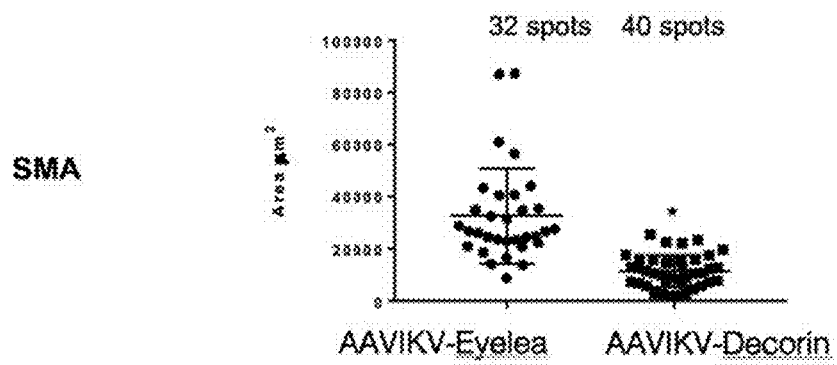

Inhibition of Choroidal Neovascularization and Fibrosis in the Outer Retina Via Intravitreal AAV Delivery Above, we found that decorin proteoglycan was capable of inhibiting laser induced CNV because of its known properties of concomitant inhibition of VEGF and TGF-β in the extracellular matrix. We wished to test the hypothesis that expression of decorin in the outer retina would be highly efficacious relative to a control GFP or expression of Eyelea (aflibercept), a recombinant anti-VEGF molecule used in the treatment of AMD. Recombinant IKV-AAV vectors expressing either GFP, Eyelea or decorin were co-injected with Nuc1 intravitreally in adult C57B1/6J mice. Three weeks later, mice were exposed to laser induced CNV and examined one week later similar to studies described above for decorin and anti-VEGF antibodies. Quantitation of CNV with isolectin and α-smooth muscle actin (SMA) revealed that AAV-IKV-decorin was significantly superior to AAV-IKV-Eyelea in both the inhibition of CNV and fibrosis (FIG. 13).

Discussion

In the present study we have described a novel peptide termed Nuc1. This peptide was designed based on the nucleolin-binding properties of laminin-1 and the heparan sulphate binding properties of VEGF165A. To our knowledge, Nuc1 is the most efficient peptide for penetration of the retina described to date. Importantly, unlike the majority of prior cell penetrating peptides (Johnson et al., 2008) or aptamers (Leaderer et al., 2015, 2016; Talreja et al., 2018) used in the retina, Nuc1 did not require chemical conjugation of peptide to cargo. The ability to deliver proteins into retinal cells and tissues without the need for a physical linkage substantially expands the utility of CPPs for therapeutic purposes. Whereas physical or chemical linkages between proteins and peptides are well described, such linkages can negatively impact protein function. (Zhang et al., 2018). The delivery system of the present invention theoretically enables taking any protein that is known to be functionally active and delivering it into cells across the plasma membrane without need for complex chemistries.

We demonstrated that heterologous proteins retained function following Nuc1 facilitated retinal delivery. For example, recombinant XIAP inhibited MNU-induced and retinal detachment-induced retinal apoptosis. Further, Nuc1 enhanced the potency of anti-fibrotic proteins such as decorin when applied to the cornea following chemical burn. This observation was unanticipated given that Nuc1 was specifically designed with the retina in consideration. Thus, it is possible that Nuc1 will function in tissues other than the retina and cornea, but this remains to be determined.

Delivery of antibodies via intravitreal injection is a current clinical standard of care (Comparison of Age-related Macular Degeneration Treatments Trials Research et al., 2012). We demonstrated that the potency of antibodies at low(er) doses could be enhanced when co-delivered with Nuc1. This has implications for 'cost of goods' as well as reducing potential toxicity due to off-target activity of drugs. For example, systemic leakage of anti-VEGF antibodies from the vitreous is deleterious to patients (Christoforidis et al., 2017; Hwang et al., 2012; Michalska-Malecka et al., 2016). A reduction in the dose of antibody needed to achieve efficacy in the vitreous may reduce such systemic side effects. Steroids represent another drug for which therapeutic use has been hampered by side effects. When injected intravitreally dexamethasone leads to cataract formation and increases in intraocular pressure (Zhang et al., 2018). It is possible that when combined with Nuc1, these side effects may be lessened due to a reduction in dose needed to be effective; although this remains to be determined.

Nuc1 was also able to enhance recombinant AAV uptake into retinal cells, specifically the photoreceptors. AAV and other viruses generate immune responses when injected at high doses (Boyd et al., 2016; Reichel et al., 2017). The ability to enhance infection reduces the total dose of virus needed to reach a therapeutic effect for applications in gene therapy. Furthermore, the ability to incorporate the Nuc1 sequence or its derivative shorter sequence into the AAV capsid simplifies the generation of recombinant AAV for use as a 'drug'. We did not find a significant increase in AAV infection when Nuc1 peptide was co-injected with Nuc1 sequence-containing AAV, perhaps due to competition for cell surface receptors required for infection. In our studies, Nuc 1 peptide combined with an AAV with a laminin-1 containing sequence in the AAV capsid led to maximum infection. Prior attempts to enhance infection of AAV via the intravitreal route have generally required biopanning through complex selection procedures (Dalkara et al., 2013). Our more 'design-oriented' approach is significantly simpler and has proven to be at least equally effective. While the safety of these vectors remains to be determined, the ability to enhance infection via the subretinal or intravitreal route significantly advances the field of ocular gene therapy. Based on the nature of retinal neurons, we anticipate that the methods described in this manuscript may be extended to other neuronal tissues, such as the brain, but that remains to be determined.

REFERENCES

Arroyo, J. G., Yang, L., Bula, D., Chen, D. F., 2005. Photoreceptor apoptosis in human retinal detachment. Am J Ophthalmol 139, 605-610.

Aumailley, M., 2013. The laminin family. Cell Adh Migr 7, 48-55.

Bechara, C., Sagan, S., 2013. Cell-penetrating peptides: 20 years later, where do we stand? FEBS Lett 587, 1693-1702.

Bennett, J., 2017. Taking Stock of Retinal Gene Therapy: Looking Back and Moving Forward. Mol Ther 25, 1076-1094.

Binder, C., Read, S. P., Cashman, S. M., Kumar-Singh, R., 2011. Nuclear targeted delivery of macromolecules to retina and cornea. J Gene Med 13, 158-170.

Birke, M. T., Lipo, E., Adhi, M., Birke, K., Kumar-Singh, R., 2014. AAV-mediated expression of human PRELP inhibits complement activation, choroidal neovascularizatiol 1 and deposition of membrane attack complex in mice. Gene Ther 21, 507-513.

Boyd, R. F., Boye, S. L., Conlon, T. J., Erger, K. E., Sledge, D. G., Langohr, I. M., Hauswirth, W. W., Komaromy, A. M., Boye, S. E., Petersen-Jones, S. M., Bartoe, J. T., 2016. Reduced retinal transduction and enhanced transgene-directed immunogenicity with intravitreal delivery of rAAV following posterior vitrectomy in dogs. Gene Ther 23, 548-556.

Cashman, S. M., Gracias, J., Adhi, M., Kumar-Singh, R., 2015. Adenovirus-mediated delivery of Factor H attenuates complement C3 induced pathology in the murine retina: a potential gene therapy for age-related macular degeneration. J Gene Med 17, 229-243.

Cebe Suarez, S., Pieren, M., Cariolato, L., Am, S., Hoffmann, U., Bogucki, A., Manlius, C., Wood, J., Ballmer-Hofer, K., 2006. A VEGF-A splice variant defective for heparan sulfate and neuropilin-1 binding shows attenuated signaling through VEGFR-2. Cell Mol Life Sci 63, 2067-2077.

Christoforidis, J. B., Briley, K., Binzel, K., Bhatia, P., Wei, L., Kumar, K., Knopp, M. V., 2017. Systemic Biodistribution and Intravitreal Pharmacokinetic Properties of Bevacizumab, Ranibizumab, and Aflibercept in a Nonhuman Primate Model. Invest Ophthalmol Vis Sci 58, 5636-5645.

Clark, S. J., Keenan, T. D., Fielder, H. L., Collinson, L. J., Holley, R. J., Merry, C. L., van Kuppevelt, T. H., Day, A. J., Bishop, P. N., 2011. Mapping the differential distribution of glycosaminoglycans in the adult human retina, choroid, and sclera. Invest Ophthalmol Vis Sci 52, 6511-6521.

Comparison of Age-related Macular Degeneration Treatments Trials Research, G., Martin, D. F., Maguire, M. G., Fine, S. L., Ying, G. S., Jaffe, G. J., Grunwald, J. E., Toth, C., Redford, M., Ferris, F. L., 3rd, 2012. Ranibizumab and bevacizumab for treatment of neovascular age-related macular degeneration: two-year results. Ophthalmology 119, 1388-1398.

Cottet, S., Schorderet, D. F., 2009. Mechanisms of apoptosis in retinitis pigmentosa. Curr Mol Med 9, 375-383.

Dalkara, D., Byrne, L. C., Klimczak, R. R., Visel, M., Yin, L., Merigan, W. H., Flannery, J. G., Schaffer, D. V., 2013. In vivo-directed evolution of a new adeno-associated virus for therapeutic outer retinal gene delivery from the vitreous. Sci Transl Med 5, 189ra176.

De Coupade, C., Fittipaldi, A., Chagnas, V., Michel, M., earlier, S., Tasciotti, E., Darmon, A., Ravel, D., Kearsey, J., Giacca, M., Cailler, F., 2005. Novel human-derived cell-penetrating peptides for specific subcellular delivery of therapeutic biomolecules. Biochem J 390, 407-418.

Donnini, S., Solito, R., Monti, M., Balduini, W., Carloni, S., Cimino, M., Bampton, E. T., Pinon, L. G., Nicotera, P., Thorpe, P. E., Ziche, M., 2009. Prevention of ischemic brain injury by treatment with the membrane penetrating apoptosis inhibitor, TAT-BH4. Cell Cycle 8, 1271-1278.

Gubbiotti, M. A., Vallet, S. D., Ricard-Blum, S., Iozzo, R. V., 2016. Decorin interacting network: A comprehensive analysis of decorin-binding partners and their versatile functions. Matrix Biol 55, 7-21.

Guidotti, G., Brambilla, L., Rossi, I D., 2017. Cell-Penetrating Peptides: From Basic Research to Clinics. Trends Pharmacol Sci 38, 406-424.

Hollander, B. A., Liang, M. Y., Besharse, J. C., 1999. Linkage of a nucleolin-related protein and casein kinase II with the detergent-stable photoreceptor cytoskeleton. Cell Motil Cytoskeleton 43, 114-127.

Hotchkiss, R. S., McConnell, K. W., Bullok, K., Davis, C. G., Chang, K. C., Schwuls, t S. J., Dunne, J. C., Dietz, G. P., Bahr, M., McDunn, J. E., Karl, I. E., Wagner, T. H., Cobb, J. P., Coopersmith, C. M., Piwnica-Worms, D., 2006. TAT-BH4 and TAT-Bcl-xi peptides protect against sepsis-induced lymphocyte apoptosis in vivo. J Immunol 176, 5471-5477.

Hovanessian, A. G., Soundaramourty, C., El Khoury, D., Nondier, I., Svab, J., Krust, B., 2010. Surface expressed nucleolin is constantly induced in tumor cells to mediate calcium-dependent ligand internalization. PLoS One 5, e15787.

Hwang, D. J., Kim, Y. W., Woo, S. J., Park, K. H., 2012. Comparison of systemic adverse events associated with intravitreal anti-VEGF injection: ranibizumab versus bevacizumab. J Korean Med Sci 27, 1580-1585.

Jarvelainen, H., Sainio, A., Wight, T. N., 2015. Pivotal role for decorin in angiogenesis. Matrix Biol 43, 15-26.

Jin, K., Zhu, Y., Sun, Y., Mao, X. O., Xie, L., Greenberg, D. A., 2002. Vascular endothelial growth factor (VEGF) stimulates neurogenesis in vitro and in vivo. Proc Natl Acad Sci U S A 99, 11946-11950.

Johnson, L. N., Cashman, S. M., Kumar-Singh, R., 2008. Cell-penetrating peptide for enhanced delivery of nucleic acids and drugs to ocular tissues including retina and cornea. Mol Ther 16, 107-114.

Johnson, L. N., Cashman, S. M., Read, S. P., Kumar-Singh, R., 2010. Cell penetrating peptide POD mediates delivery of recombinant proteins to retina, cornea and skin. Vision Res 50, 686-697.

Khabou, H., Desrosiers, M., Winckler, C., Fouquet, S., Auregan, G., Bemelmans, A. P., Sahel, J. A., Dalkara, D., 2016. Insight into the mechanisms of enhanced retinal transduction by the engineered AAV2 capsid variant-7 m8. Biotechnol Bioeng 113, 2712-2724.

Kibbey, M. C., Johnson, B., Petryshyn, R., Jucker, M., Kleinman, H. K., 1995. A 110-kD nuclear shuttling protein, nucleolin, binds to the neurite-promoting IKVAV site of laminin-1. J Neurosci Res 42, 314-322.

Kotterman, M. A., Yin, L., Strazzeri, J. M., Flannery, J. G., Merigan, W. H., Schaffer, D. V., 2015. Antibody neutralization poses a barrier to intravitreal adeno-associated viral vector gene delivery to non-human primates. Gene Ther 22, 116-126.

Koutsioumpa, M., Papadimitriou, E., 2014. Cell surface nucleolin as a target for anti-cancer therapies. Recent Pat Anticancer Drug Discov 9, 137-152.

Krilleke, D., Ng, Y. S., Shima, D. T., 2009. The heparin-binding domain confers diverse functions of VEGF-A in development and disease: a structure-function study. Biochem Soc Trans 37, 1201-1206.

Leaderer, D., Cashman, S. M., Kumar-Singh, R., 2015. Topical application of a G-Quartet aptamer targeting nucleolin attenuates choroidal neovascularization in a model of age-related macular degeneration. Exp Eye Res 140, 171-178.

Leaderer, D., Cashman, S. M., Kumar-Singh, R., 2016. G-quartet oligonucleotide mediated delivery of proteins into photoreceptors and retinal pigment epithelium via intravitreal injection. Exp Eye Res 145, 380-392.

Leonard, K. C., Petrin, D., Coupland, S. G., Baker, A. N., Leonard, B. C., Lacasse, E. C., Hauswirth, W. W., Korneluk, R. G., Tsilfidis, C., 2007. XIAP protection of photoreceptors in animal models of retinitis pigmentosa. PLoS One 2, e314.

Libby, R. T., Champliaud, M. F., Claudepierre, T., Xu, Y., Gibbons, E. P., Koch, M., Burgeson, R. E., Hunter, D. D., Brunken, W. J., 2000. Laminin expression in adult and developing retinae: evidence of two novel CNS laminins. J Neurosci 20, 6517-6528.

Maidana, D. E., Tsoka, P., Tian, B., Dib, B., Matsumoto, H., Kataoka, K., Lin, H., Miller, J. W., Vavvas, D. G., 2015. A Novel ImageJ Macro for Automated Cell Death Quantitation in the Retina. Invest Ophthalmol Vis Sci 56, 6701-6708.

Michalska-Malecka, K., Kabiesz, A., Kimsa, M. W., Strzalka-Mrozik, B., Forminska-Kapuscik, M., Nita, M., Mazurek, U., 2016. Effects of intravitreal ranibizumab on the untreated eye and systemic gene expression profile in age-related macular degeneration. Clin Interv Aging 11, 357-365.

Mongelard, F., Bouvet, P., 2007. Nucleolin: a multiFACeTed protein. Trends Cell Biol 17, 80-86. Park, K., 2011.

Cardioprotective properties of Tat-BH4 and Pip2b-BH4 in vivo. J Control Release 156, 117.

Petrin, D., Baker, A., Coupland, S. G., Liston, P., Narang, M., Damji, K., Leonard, B., Chiodo, V. A., Timmers, A., Hauswirth, W., Korneluk, R. G., Tsilfidis, C., 2003. Structural and functional protection of photoreceptors from MNU-induced retinal degeneration by the X-linked inhibitor of apoptosis. Invest Ophthalmol Vis Sci 44, 2757-2763.

Phulke, S., Kaushik, S., Kaur, S., Pandav, S. S., 2017. Steroid-induced Glaucoma: An Avoidable Irreversible Blindness. J Curr Glaucoma Pract 11, 67-72.

Pleyer, U., Ursell, P. G., Rama, P., 2013. Intraocular pressure effects of common topical steroids for post-cataract inflammation: are they all the same? Ophthalmol Ther 2, 55-72.

Reichel, F. F., Dauletbekov, D. L., Klein, R., Peters, T., Ochakovski, G. A., Seitz, I. P., Wilhelm, B., Ueffing, M., Biel, M., Wissinger, B., Michalakis, S., Bartz-Schmidt, K. U., Fischer, M. D., Consortium, R.-C., 2017. AAV8 Can Induce Innate and Adaptive Immune Response in the Primate Eye. Mol Ther 25, 2648-2660.

Robinson, G. S., Ju, M., Shih, S. C., Xu, X., McMahon, G., Caldwell, R. B., Smith, L. E., 2001. Nonvascular role for VEGF: VEGFR-1, 2 activity is critical for neural retinal development. FASEB J 15, 1215-1217.

Rong, Y. P., Bultynck, G., Aromollaran, A. S., Zhong, F., Parys, J. B., De Smedt, H., Mignery, G. A., !Roderick, H. L., Bootman, M. D., Distelhorst, C. W., 2009. The BH4 domain of Bcl-2 inhibits ER calcium release and apoptosis by binding the regulatory and coupling domain of the IP3 receptor. Proc Natl Acad Sci US A 106, 14397-14402.

Talreja, D., Cashman, S. M., Dasari, B., Kumar, B., Kumar-Singh, R., 2018. G-quartet oligonucleotide mediated delivery of functional X-linked inhibitor of apoptosis protein into retinal cells following intravitreal injection. Exp Eye Res 175, 20-31.

Tashiro, K., Sephel, G. C., Weeks, B., Sasaki, M., Martin, G. R., Kleinman, H. K., Yamada, Y., 1989. A synthetic peptide containing the IKVAV sequence from the A chain of laminin mediates cell attachment, migration, and neurite outgrowth. J Biol Chem 264, 16174-16182.

Zhang, G., Liu, S., Yang, L., Li, Y., 2018. The role of Dexamethasone in clinical pharmaceutical treatment for patients with cataract surgery. Exp Ther Med 15, 2177-2181.

Example 2

Topical Delivery of Decorin Using Cell Penetrating Peptide Nuc1 Enhances Recovery of Alkali Burn Induced Corneal Injury in Mice Corneal injury accounts for approximately 4% of all cases of total vision loss. Approximately 80% of ocular injuries are chemical in nature, of which alkali and acidic agents cause approximately 11-22% of ocular traumas and 4% of all occupational injuries [1-3]. The corneal epithelium acts as a barrier between the external environment and the interior of the eye [4]. When the corneal surface is damaged, several responses, including fibrosis, angiogenesis and inflammation are activated both to heal the injury and to protect the eye from further damage. In excess, however, these responses may themselves result in further damage [5]. Acute inflammation and neovascularization in the anterior segment can result in aberrant healing of epithelial tissue and corneal scarring. Alkali agents penetrate ocular tissues rapidly due to lipophilic properties, causing necrosis and ischemia [6]. Patients with corneal injury due to alkali burn are at an increased risk of glaucoma and irreversible vision loss.

Alkali burn results in infiltration of macrophages and leukocytes in the cornea, as well as in the upregulation of pro-inflammatory cytokines, such as IL-1β, TNF-α, IL-6 and vascular endothelial growth factor A (VEGF-A). An imbalance of pro-angiogenic and anti-angiogenic molecules in the cornea triggers neovascularization [7, 8]. Epithelial regeneration through cell proliferation and apoptosis of stromal keratocytes occurs adjacent to the site of burn/injury [9]. In addition to corneal damage, it has been reported that alkali burn can cause apoptosis of retinal ganglion cells, as well as optic nerve damage.

The eye lids are the first line of ocular defense, shielding the eye from allergens, foreign particles, and pathogens. The blinking action of the eye washes the ocular surface and renews the tear film, which consists of immunoglobulin A and G and anti-microbial proteins, such as lysozyme, β-Lysin, and metal chelators [10, 11]. However, one of the challenges associated with topical delivery of molecules to the surface of the eye is the rapid clearance of drugs from the surface by the tear film, resulting in a loss of >95% of drug. The half-life of the drug that manages to penetrate the interior chamber is usually short due to recycling of the aqueous humor. To our knowledge, there are no reports of topical delivery of protein to the cornea for the treatment of alkali burn.

Decorin is a small, leucine rich proteoglycan with an important role in the regulation of cellular proliferation, survival and differentiation through regulation of various growth factors, such as TGF-fβ, in the cornea [12-16]. Decorin also plays a critical role in the maintenance of corneal transparency by inhibiting scar formation and blood vessel growth. Mutations in decorin have been shown to correlate with congenital stromal dystrophy [17].

Over-expression of decorin has been shown to significantly reduce fibrosis in in vivo models of brain and spinal cord injury. In this study, we tested the effect of topical delivery of decorin alone and topical co-delivery of decorin and the cell penetrating peptide Nuc1 on the levels of fibrosis, angiogenesis, apoptosis and inflammation in the murine model of alkali burn in the cornea.

Materials and Methods:

Peptide synthesis: Nuc1 peptide, sequence ASIKVA-VSAGGDKPRR (SEQ ID NO: 3), was synthesized by Thermo Fisher Scientific to >99% purity.

Animals: Six to eight week old C57BL/6 mice were purchased from Jackson Laboratory (Bar Harbor, Me.) and housed under a 12 hr light/dark cycle. This study was carried out in accordance with the Statement for the Use of Animals in Ophthalmic and Vision Research, set out by the Association of Research in Vision and Ophthalmology (ARVO) and was approved by Tufts University Institutional Animal Care and Use Committee (IACUC).

Animal model of injury: Mice were anesthetized by intraperitoneal injection of a mixture containing 0.1 mg/g body weight Ketamine (Phoenix™, St Jloseph, Mo.) and of 0.01 mg/g body weight Xylazine (Llloyed, Shenandoah, Iowa) followed by topical application of 0.5% proparacaine hydrochloride (Akorn Inc., Lake Forest, Ill., USA) for topical analgesia to the cornea. Mice were kept warm during anesthesia. Alkali burn was induced in the cornea by applying 2 mm filter paper discs soaked with 1N sodium hydroxide (NaOH) on the central cornea of the right eye for 30 seconds. The filter paper was gently removed from the cornea and the cornea rinsed with phosphate buffered saline (PBS) 10 times to clear residual NaOH. The left eye was left unexposed to NaOH and served as a control. Topical application of PBS, recombinant decorin (0.5 µg), decorin (0.5 µg)+Nuc1 (0.5 µg) was initiated 24 hours after exposure to NaOH. The treatments were applied topically once a day for seven days. Images of the eye were captured on day 7 using a digital camera. After 7 days, mice were sacrificed by $CO_2$ inhalation, followed by cervical dislocation. The eyes were enucleated and fixed in 4% paraformaldehyde. Corneal cryosections were taken using a Micron 550 cryostat.

Immunochemistry: Cryosections were air dried for 10 minutes and washed in PBS for 5 minutes. They were subsequently incubated in 6% normal goat serum and PBS-Triton for 1 hour at room temperature for permeabilization and blocking. The slides were incubated with FITC-conjugated isolectin or with primary antibody against one of following: α-smooth muscle actin (SMA), glial fibrillary acidic protein (GFAP), CD45, transforming growth factor beta (TGF-β1), F4/80, transforming growth factor beta (TGF-β1) (Abcam; ab92486), or activated Caspase-3. This incubation was performed at 4° C. in a moist chamber overnight. For samples treated with antibodies, detection was performed by incubation with a secondary Cy3-conjugated goat anti-rabbit/anti-mouse antibody (Jackson lmmunoResearch, West Grove, Pa.) for 1 hour at room temperature. The slides were washed three times with PBS and mounted in Vectashield anti fade mounting medium containing DAPI to counterstain the nuclei. Imaging of stained sections was performed using an Olympus IX51 microscope and appropriate filters. Images were captured using a Retiga 2000r camera. The intensity of the antibody specific staining was quantified using ImageJ software.

Histopathology: The eyes were harvested for histology 7 days post-treatment and fixed in Hartman's fixative. After 48 hours, the specimens were dehydrated through alcohol steps and embedded in paraffin. 5 mm sections were cut at different planes, including the optic nerve region, and stained with Hematoxylin & Eosin (H&E). Imaging of stained sections was performed using an Olympus BX51 microscope using a Retiga 2000r camera.

Multiplex ELISA: Multiplex ELISA was performed to detect IL-6, IL-17, IL-10, IFN-G, TNF-α, and IL-1β using Bio-plex pro mouse cytokineTh17 A 6 plex group I (Bio-Rad, M6000007NY), as per the manufacturer's instructions. Briefly, alkali burn was induced as described above. Mice were sacrificed on day 7 and corneas were extracted. The corneas were dissected into small pieces and stored at −80° C. in Bioplex cell lysis buffer. Two corneas were pooled together for each sample and 50 µl of the lysate was used in duplicate for each sample. The samples were run using the Bio plex manager MP software and the data was analyzed using Bioplex manager 6.0.

TUNEL assay: To detect cell death, the terminal deoxynucleotidyl transferase-mediated dUTP-biotin nick-end labeling (TUNEL) method was performed on corneal cryosections using the In Situ Death Detection Kit, TMR Red (Sigma), as per the manufacturer's instructions. The sections were imaged, as described above, and images used for quantification of TUNEL positive cells using ImageJ (FIJI version and plug in), as previously described [18].

Statistical analysis: The experimental values are presented as mean±SEM. The statistical differences between more than two groups were analyzed using a oneway ANOVA test, while the differences between two groups were analyzed using an unpaired T test. A p-value of less than or equal to 0.05 was considered statistically significant.

Results

Figure 14:
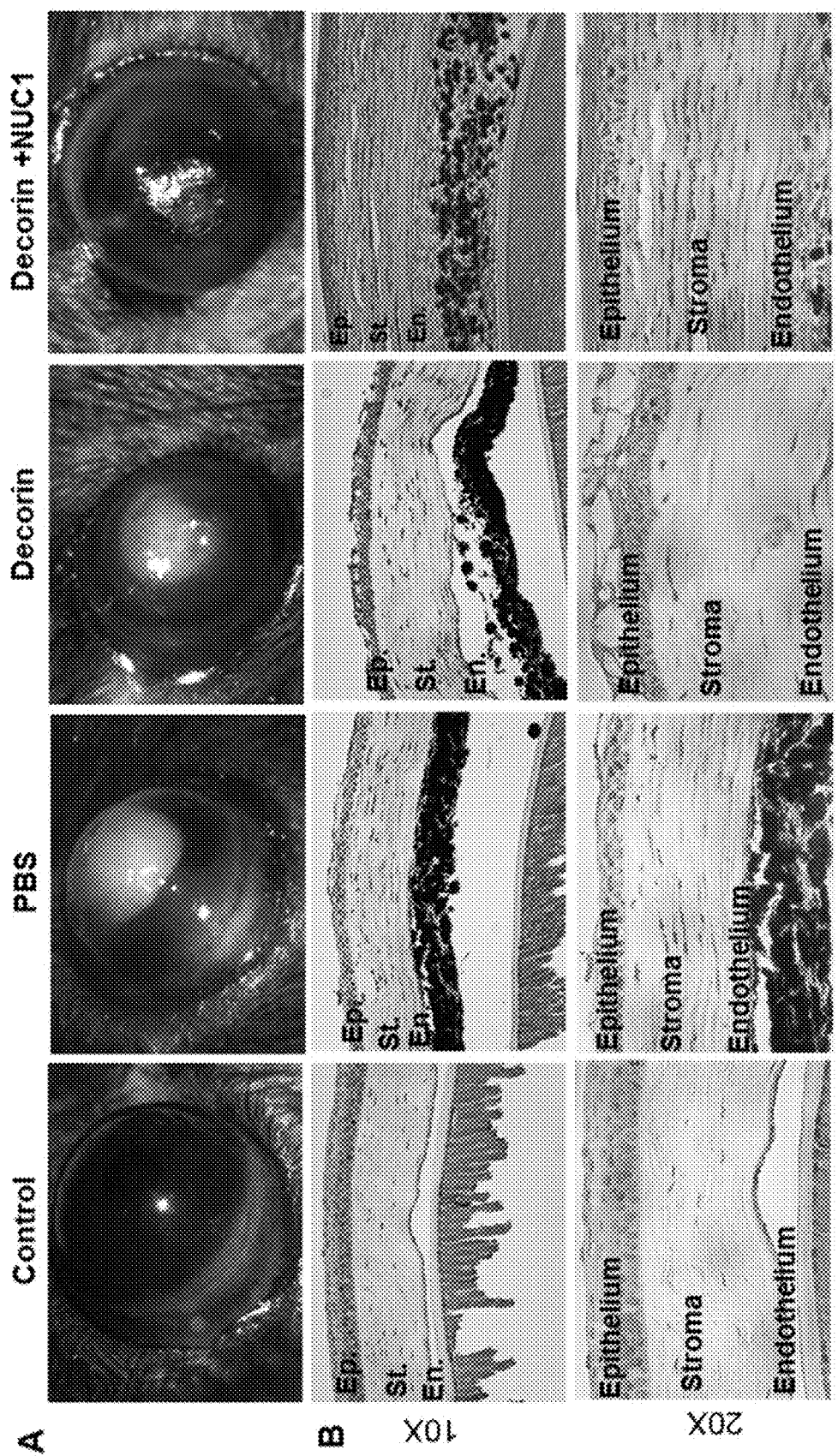
FIG. 14 shows that topical application of decorin co-delivered with Nuc1 (decorin+Nuc1) reduces corneal opacity and attenuates corneal thickening following alkali burn. (A) Representative images of eyes of mice unexposed to alkali burn and treatment (Control) or exposed to alkali burn and one of the topical treatments: phosphate buffered saline (PBS), decorin alone, or decorin+Nuc1. (B) Hematoxylin (nuclei; blue) and eosin (extracellular matrix and cytoplasm; pink) stained transverse paraffin sections (10× and 20× magnification) of cornea of mice unexposed to alkali burn and treatment (Control) or exposed to alkali burn and one of the topical treatments: PBS, decorin alone, or decorin+Nuc1. Ep, epithelium; St, stroma; En, endothelium.

Nuc1 Enhances the Ability of Decorin to Reduce Corneal Opacity and Cellular Infiltration To test the effect of topical application of decorin only and decorin coupled with Nuc1 (decorin+Nuc1) on corneal opacity, mice were exposed to alkali burn, as described in methods. At 24 hours post alkali burn, decorin only, decorin+Nuc1, or PBS were applied once daily for 7 days. On day 7, mice were sacrificed for imaging of corneas (FIG. 14A). The corneas of control mice, unexposed to alkali burn or drug treatment, were observed to be smooth and transparent (FIG. 14A). In contrast, corneas of alkali burn exposed mice treated with PBS for 7 days were observed to have a diffuse "cloudiness" throughout the surface of the cornea. In addition, the cornea had an irregular surface with conspicuous blood vessels present (FIG. 14A). Mice exposed to alkali burn followed by topical application of decorin alone showed corneas similar in appearance to those treated with PBS, with evident opacity, irregular surface and blood vessels (FIG. 14A). Mice exposed to alkali burn followed by decorin+Nuc1, however, manifested a smoother corneal surface and an obvious reduction in corneal opacity relative to the alkali burn exposed mice treated with PBS and had no conspicuous blood vessels (FIG. 14A). Mice were scored for clinical opacity based on method described by Anderson et al. [19]. According to the scoring system, the mice that received PBS treatment after alkali burn scored 4 (completely opaque with no view of pupil), mice that received decorin scored 2.8 (opaque, pupils hardly detectable) and the mice that received decorin+Nuc1 scored 1.5 (slightly hazy, iris and pupil still detectable).

Transverse sections of the corneas of alkali burn exposed mice treated with each of the above were stained with hematoxylin and eosin (H+E; FIG. 14B). Relative to the corneas of untreated control mice, the corneas of alkali burn exposed mice treated with PBS showed a thinner cornea and loss of cells of the epithelial cell layer (FIG. 14B). In addition, there was a marked cellular infiltration within and below the cornea. An increase in thickness of the epithelium was observed in the corneas of alkali burn exposed mice treated with decorin relative to corneas treated with PBS (FIG. 14B). However, vacuolization was apparent in corneas treated with decorin. In contrast, in corneas of alkali burn exposed mice treated with decorin+Nuc1, a restoration of the upper cellular layers of the epithelium was apparent, with increased integrity of the corneal surface (FIG. 14B).

Decorin+Nuc1 Significantly Reduces Neovascularization and Fibrosis in Alkali Burn Cornea Following alkali burn, the cornea is prone to neovascularization and fibrosis. Upregulation of transforming growth factor beta (TGF-β) promotes migration of corneal epithelial cells and keratocytes to the site of the alkali burn where the keratocytes differentiate into myofibroblasts [20]. Uncontrolled and persistent activation of myofibroblasts leads to pathological fibrosis. We documented the presence of vascular endothelial cells and the expression of alpha smooth muscle actin (SMA), a marker of myofibroblasts, in corneas post alkali burn [21]. In order to determine the effect of decorin alone or decorin+Nuc1 on alkali burn-induced corneal neovascularization and fibrosis, mice were exposed to alkali burn and treated as described above. At 7 days post-treatment, the mice were sacrificed and their corneas were harvested for cryosectioning and stained with FITC-conjugated Griffonia Simplificolia Lectin-1(GSL I)/Isolectin and an antibody against alpha smooth muscle actin (SMA).

Figure 15:
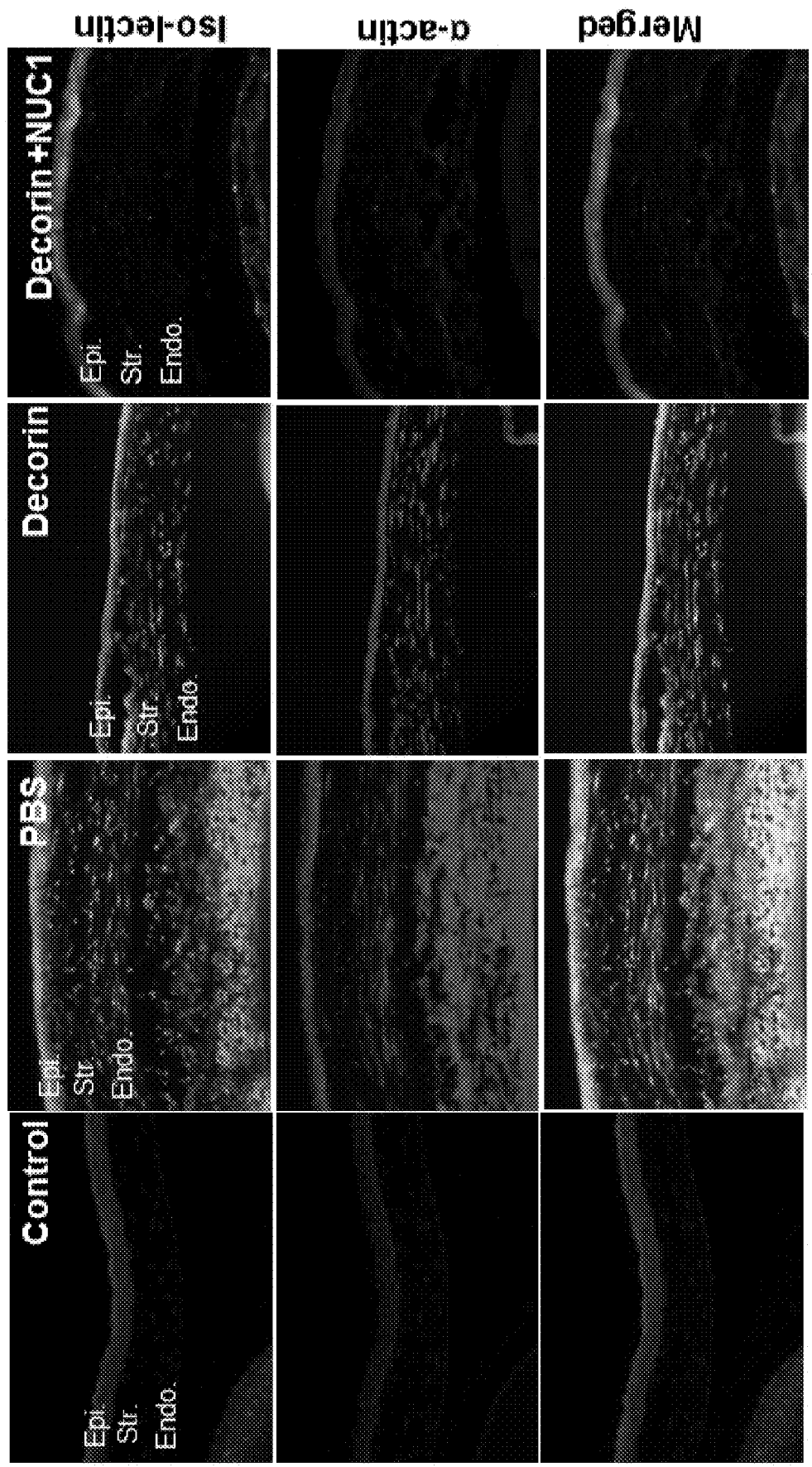
FIG. 15 shows that topical application of decorin+Nuc1 significantly reduces neovascularization and fibrosis in the cornea of mice exposed to alkali burn. (A) Representative images of cryosections of corneas of mice unexposed to alkali burn and treatment (Control) or exposed to alkali burn and one of the topical treatments: PBS, decorin alone, or decorin+Nuc1. The cryosections were stained for either GSL I (iso-lectin; green, top panels) or smooth muscle actin (SMA, α-actin; red, middle panels). Merged images are shown in the bottom panels. The nuclei of the corneal cells are stained with DAPI (blue). Epi, epthelium; Str, stroma; Endo, endothelium. (B) Bar graphs quantifying the staining. The first graph shows a quantification of GSL I (iso-lectin) staining, which is indicative of neovascularization and angiogenesis, in corneas from each of the 3 treatment groups: PBS, decorin alone, and decorin+Nuc1. The second graph shows a quantification of SMA (α-actin) staining, which is indicative of fibrosis, in corneas from each of the 3 treatment groups: PBS, decorin alone, and decorin+Nuc1.*$p<0.05$ (student t-test)
Figure 15:
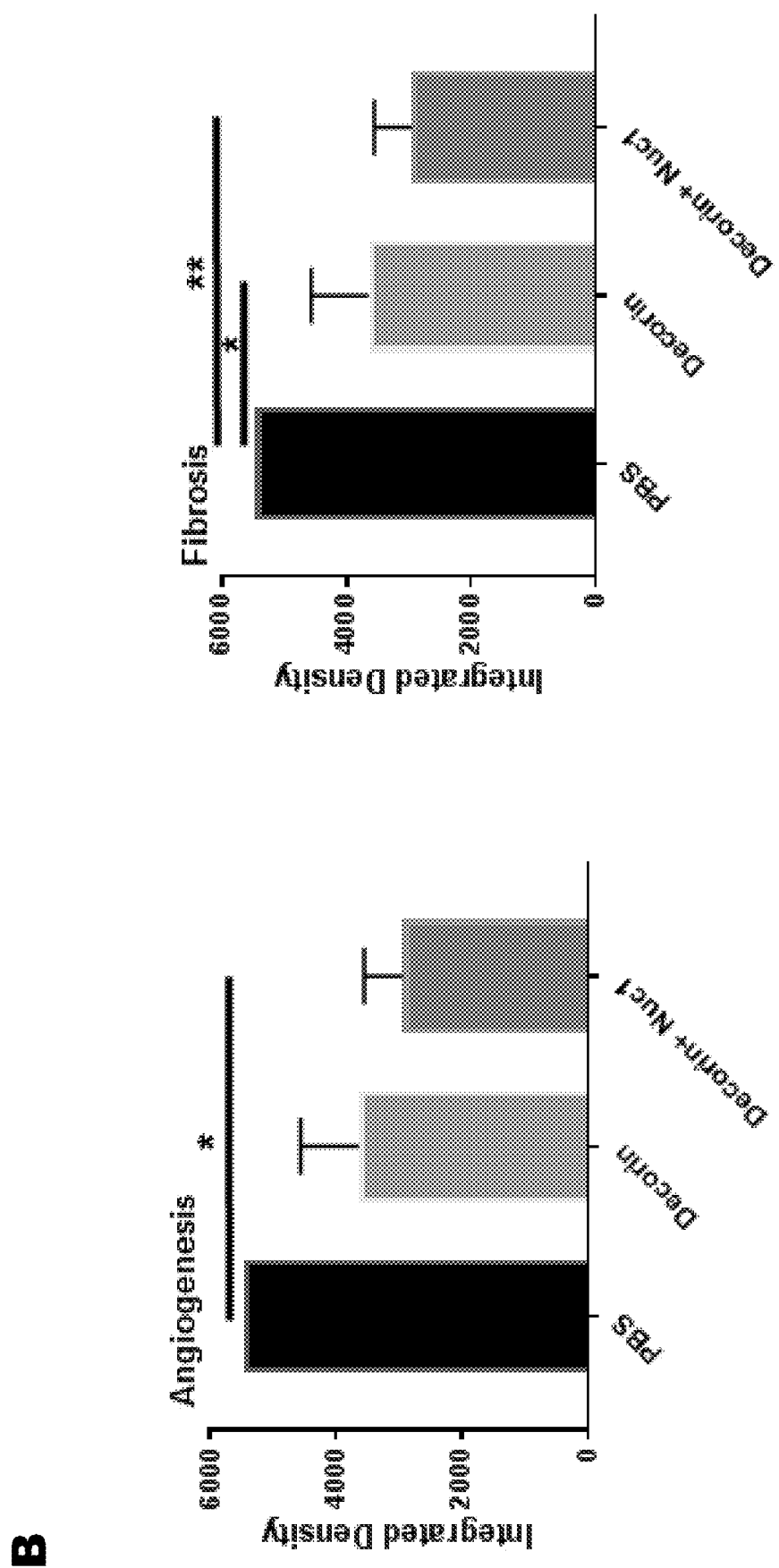

Little or no staining was observed for either isolectin (green) or SMA (red) in corneas of untreated control mice (FIG. 15A). Corneas of alkali exposed mice treated with PBS, however, showed extensive isolectin and SMA staining throughout all layers of the cornea, suggestive of extensive neovascularization and fibrosis. Topical application of decorin to alkali burn exposed corneas showed an obvious reduction in isolectin staining in the epithelium of the cornea, the stroma and endothelium, as well as in the aqueous humor (FIG. 15A), indicative of reduced neovascularization. Some modest reduction of SMA staining was evident in corneas treated with decorin, particularly in the posterior cornea and in the aqueous humor. However, topical application of decorin+Nuc1 to alkali burn exposed corneas exhibited almost complete elimination of both isolectin and SMA staining in the stroma, endothelium and aqueous humor, with considerable reduction of both stains in the epithelium (FIG. 15A). This suggests that decorin+Nuc1 mediates very significant protection from neovascularization and fibrosis in alkali burn exposed corneas.

Quantification of the isolectin staining of the corneas (FIG. 15B) showed that although topical application of decorin alone visibly reduced isolectin staining in the cornea, the amount of GSL I stain is not significantly different to that of PBS treated corneas. Topical application of decorin+Nuc1 to alkali burn exposed corneas, however, showed a significant 83.9% (p<0.042) reduction in isolectin staining relative to PBS treated corneas, indicating a significant reduction in neovascularization. Quantification of the SMA staining of the corneas showed that topical application of decorin alone significantly reduced SMA staining by 33.25% (p<0.025) relative to PBS treated corneas. Topical application of Nuc1+decorin to alkali burn exposed corneas, however, resulted in a more significant 46.22% (p<0.0028) reduction in SMA staining relative to PBS treated corneas (FIG. 15B), suggesting an enhanced ability of decorin+Nuc1 relative to decorin alone to protect against fibrosis.

Figure 16:
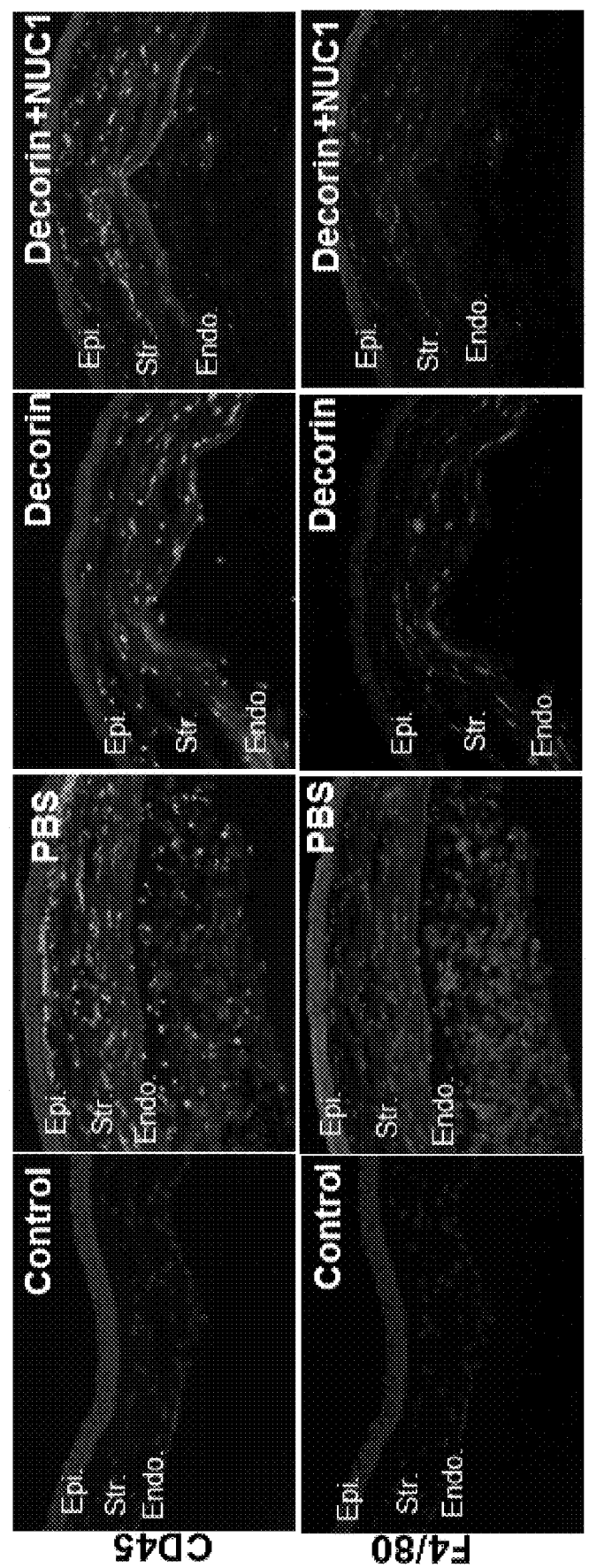
FIG. 16 shows that decorin+Nuc1 significantly reduces infiltration of inflammatory cells in the cornea of mice exposed to alkali burn. (A) Representative images of cryosections of corneas of mice unexposed to alkali burn and treatment (Control) or exposed to alkali burn and one of the topical treatments: PBS, decorin alone, or decorin+Nuc1. The cryosections were stained for the inflammatory markers CD45 (green, top panels) and F4/80 (red, bottom panels). The nuclei of the corneal cells are also stained with DAPI (blue). Epi, epithelium; Str, stroma; Endo, endothelium. (B) Bar graphs quantifying the staining. The first graph shows a quantification of CD45 staining in corneas from each of the 3 treatment groups: PBS, decorin alone, and decorin+Nuc1. The second graph shows a quantification of F4/80 staining in corneas from each of the 3 treatment groups: PBS, decorin alone, and decorin+Nuc1.
Figure 16:
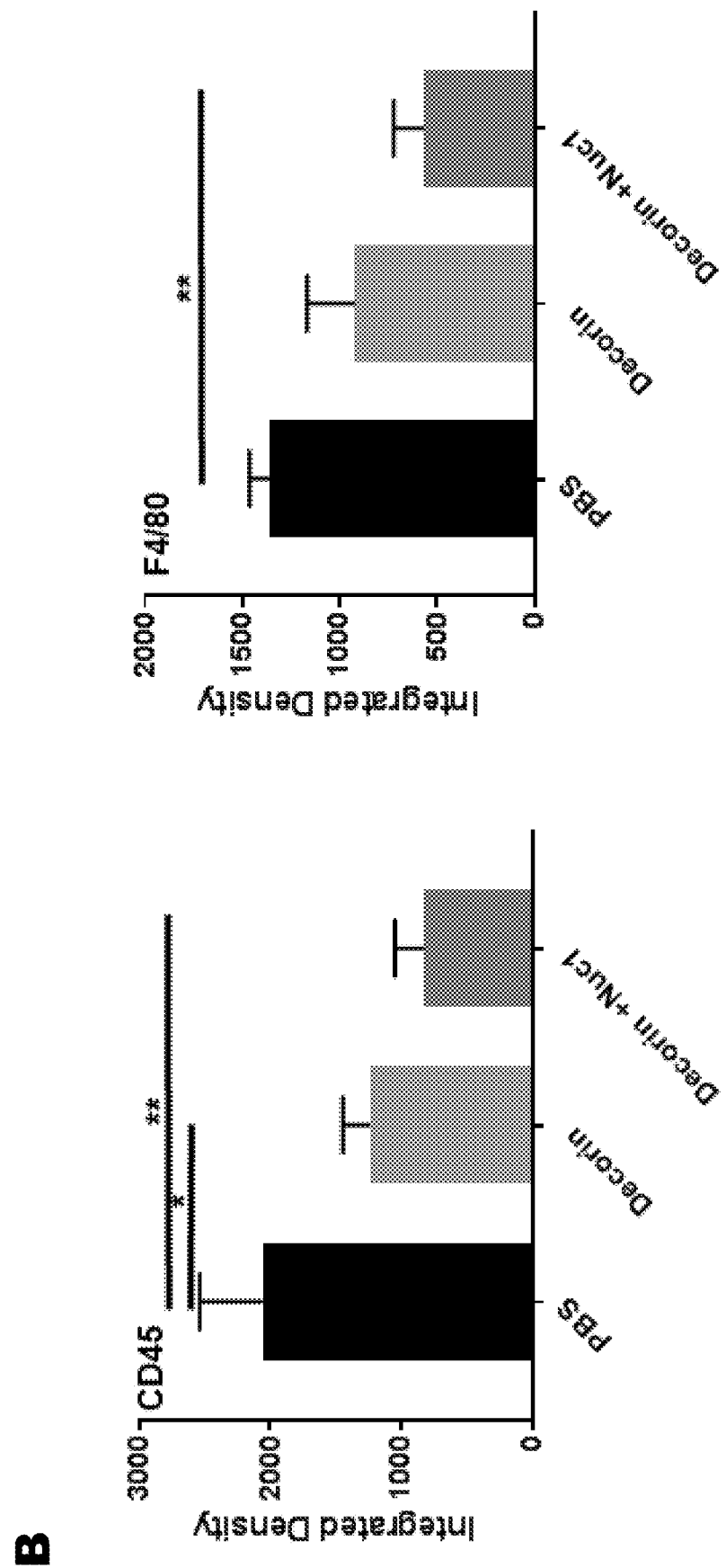

Decorin+Nuc1 Significantly Reduces Infiltration of Inflammatory Cells in the Cornea of Alkali Burn Model We next investigated inflammation in the corneas of alkali burn exposed mice following treatment with PBS, decorin alone or decorin+Nuc1. Transverse sections of corneas were stained for CD45 and F4/80 to determine the presence of leukocytes and, specifically, macrophages. In corneas of untreated control mice, there was little or no staining with either CD45 or F4/80 antibodies in the cornea, as expected (FIG. 16A). In the corneas of mice exposed to alkali burn and subsequently treated with PBS, there was extensive staining with CD45 (green channel) and F4/80 (red channel) antibodies throughout the stroma (FIG. 16A), indicative of considerable infiltration of inflammatory cells in these corneas. Corneas of mice exposed to alkali burn subsequently treated topically with either decorin alone or decorin+Nuc1 showed a reduction in CD45 and F4/80 staining in the anterior region of the stroma, close to the epithelium. Quantification of the CD45 staining in the corneas showed a significant 39.6% (p<0.0147) reduction in the number of CD45-positive cells in the corneas treated with decorin alone relative to corneas treated with PBS (FIG. 16B). Corneas treated topically with decorin+Nuc1 also showed a significant 59.8% (p<0.0017) reduction in CD45 staining relative to corneas treated with PBS (FIG. 16B). However, there was no significant difference in CD45 staining between corneas treated with decorin alone and those treated with decorin+Nuc1 (FIG. 16B). Quantification of F4/80 staining in the corneas showed a significant 57.9% (p<0.0052) reduction in staining of corneas treated with decorin+Nuc1 relative to corneas treated with PBS (FIG. 16B), indicating a marked reduction in macrophage infiltration in these corneas. In contrast, there was no significant reduction in F4/80 staining in the corneas treated with decorin alone relative to corneas treated with PBS (FIG. 16B). This data suggests that the ameliorative effect of topically applied decorin+Nuc1 on infiltration of inflammatory cells in the cornea of alkali burn exposed mice is more efficient than that of topical application of decorin alone, particularly with regard to macrophages.

Figure 17:
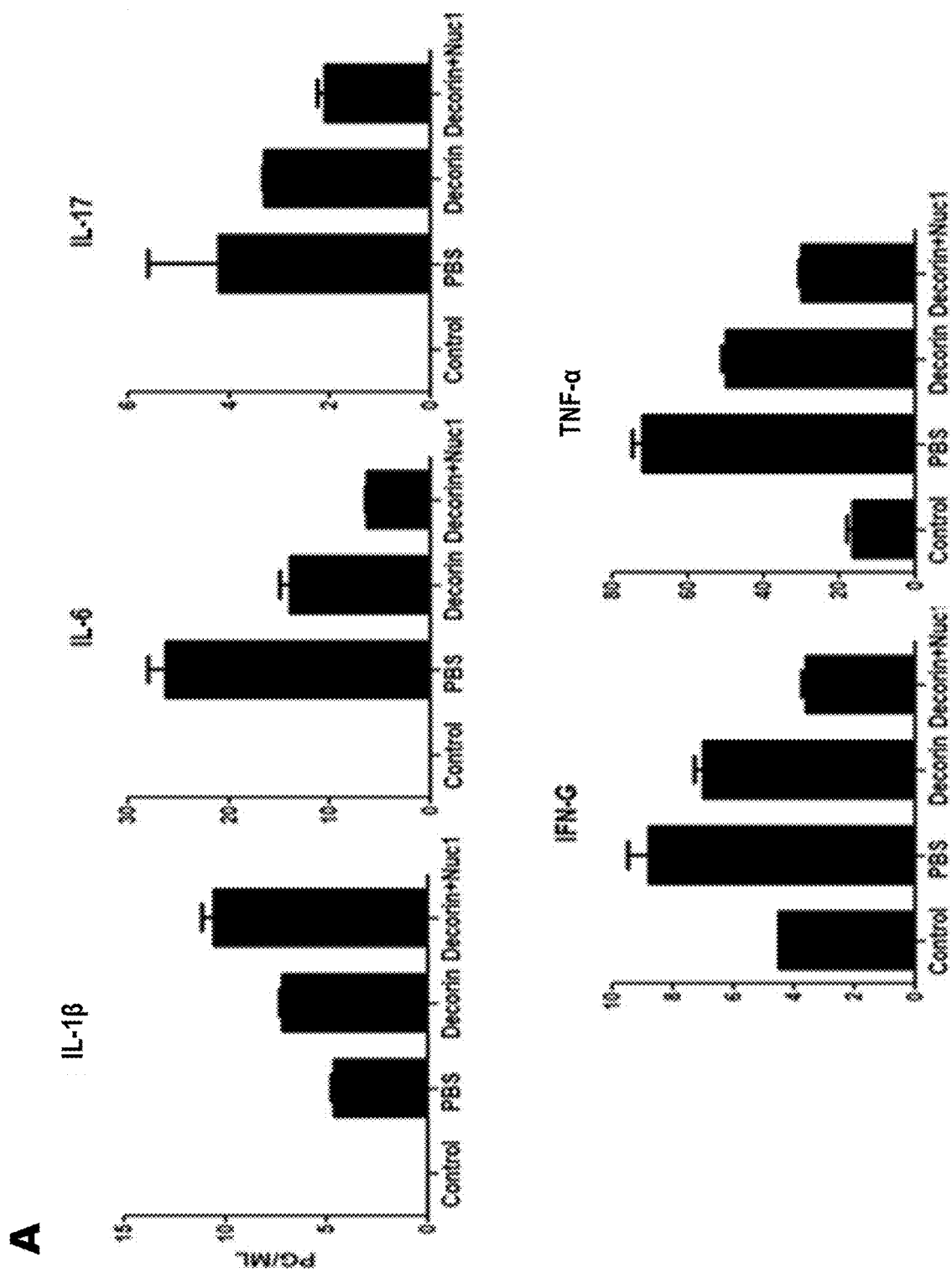
FIG. 17 shows that decorin+Nuc1 significantly reduces expression of cytokines (except for IL-1β) in the cornea of mice exposed to alkali burn. (A) Graphs showing the expression levels (picograms/milliliter, pg/ml) of the cytokines interleukin (IL)-1 beta (IL-1β), IL-6, IL-17, interferon-gamma (IFN-G) and tumor necrosis factor alpha (TNF-α) in lysate extracted from corneas of mice unexposed to alkali burn and treatment (Control) or exposed to alkali burn and one of the topical treatments: PBS, decorin alone, or decorin+Nuc1. (B) Representative images of cryosections of corneas of mice unexposed to alkali burn and treatment (Control) or exposed to alkali burn and one of the topical treatments: PBS, decorin alone, or decorin+Nuc1. The cryosections were stained with an antibody for the inflammatory cytokine transforming growth factor beta (TGF-β1, red). Epi, epithelium; Str, stroma; Endo, endothelium.
Figure 17:
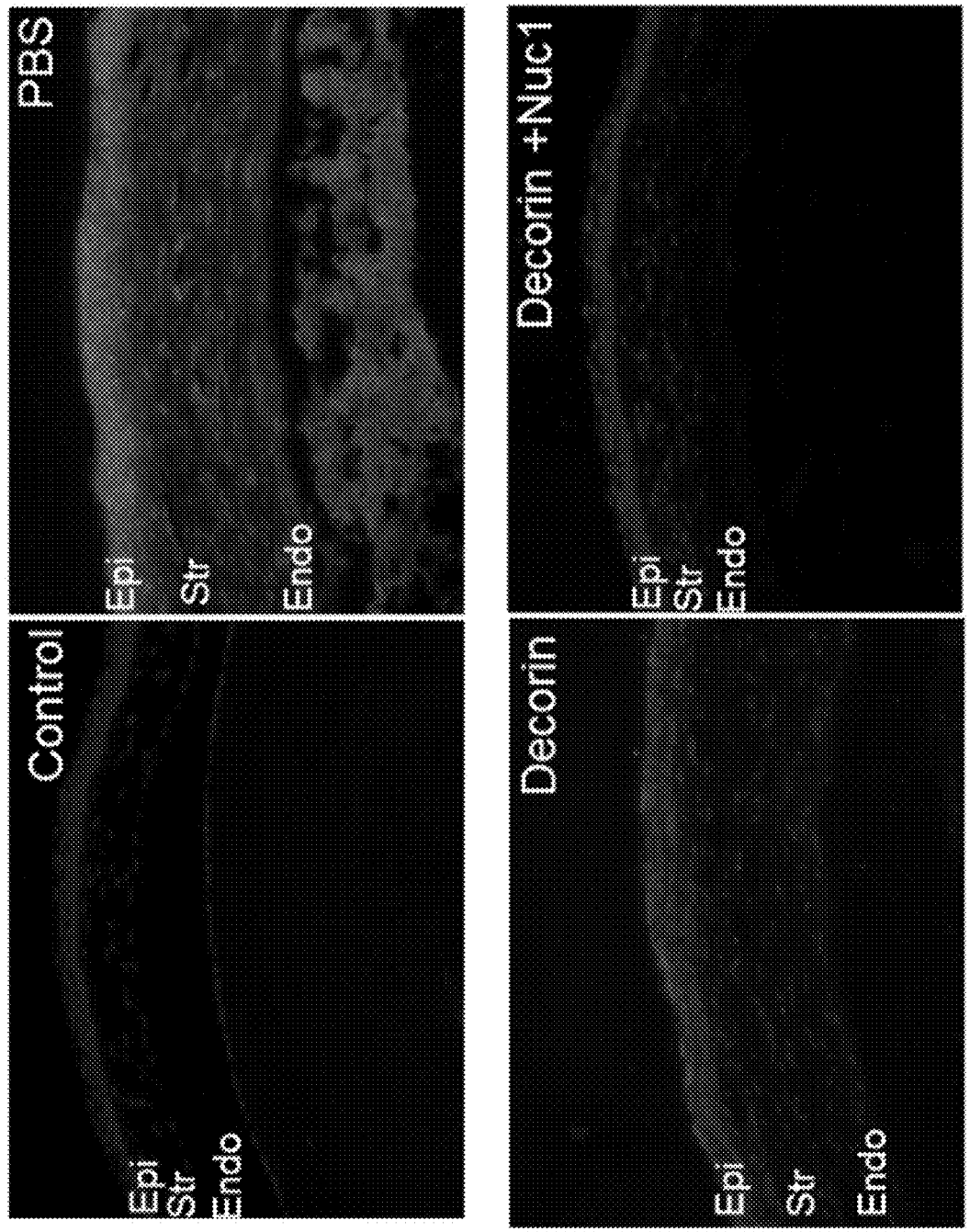

The inflammatory markers CD45 and F4/80 play an important role in the production of cytokines/chemokines at the site of injury, which are responsible for further tissue destruction and scarring. Thus, we further determined the levels of expression of Th17 cytokines using a Bioplex assay. Corneal lysates were harvested 7 days following treatment of mice exposed to alkali burn and assayed for levels of IL-1beta (IL-1β), IL-6, tumor necrosis factor alpha (TNF-α), interferon gamma (IFN-G), IL-17 and IL 10. Five of cytokines (TNF-α, IL-1β, IL-6, IL-17 and IFN-G) were observed to be elevated in the corneas of mice exposed to alkali burn and treated with PBS, relative to corneas of untreated control mice unexposed to alkali burn (FIG. 17A). The levels of the cytokine IL-10 were below the detection limits of the assay in the control and treated groups (data not shown). For TNF-α, IFN-G, IL-17 and IL-6, we observed a reduction in expression following treatment with either decorin alone or decorin+Nuc1 (FIG. 17A), relative to PBS treated mice. Notably, there was a greater reduction in expression in mice treated with decorin+Nuc1 than in those treated with decorin alone. Interestingly, an increased expression of IL-1β was observed in the corneas of mice treated with decorin alone and decorin+Nuc1 (FIG. 17A).

Alkali burn also results in production of the inflammatory cytokine transforming growth factor beta (TGF-β1), which plays an important role in differentiation of keratocytes to myofibroblasts, and aggravates the damage of the corneal tissue by inducing further expression of cytokines which in turn form an inflammation feed-back loop. Using antibody staining for TGF-β1, we observed significant expression of TGF-β1 in the epithelium, stroma, and endothelium of corneas following alkali burn in the corneas of mice treated with PBS (FIG. 17B). While treatment with decorin alone resulted in lower expression of TGF-β1, mice treated with decorin+Nuc1 had substantially lower levels of TGF-β1 relative to decorin alone (FIG. 17B).

Figure 18:
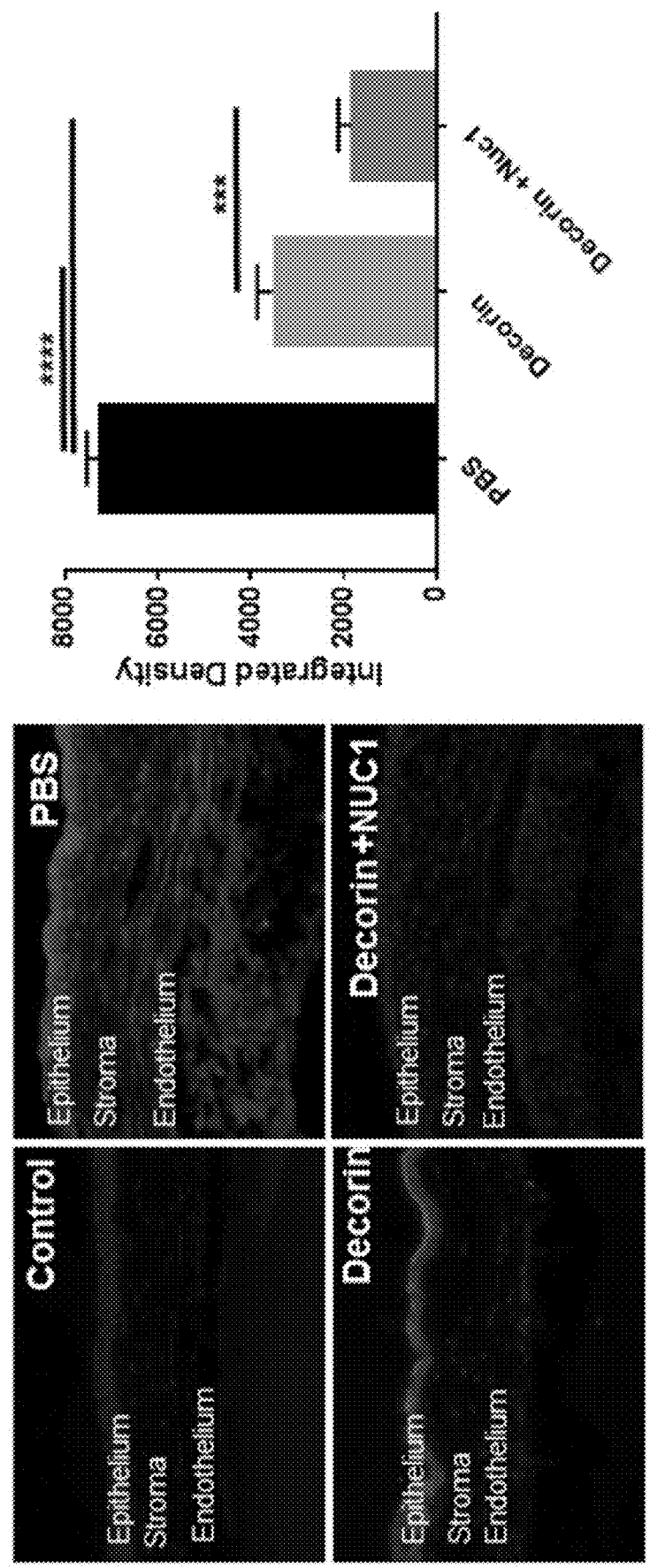
FIG. 18 shows that decorin+Nuc1 significantly reduces activation of Caspase-3 in the cornea of mice exposed to alkali burn. Representative images of cryosections of corneas of mice unexposed to alkali burn and treatment (Control) or exposed to alkali burn and one of the topical treatments: PBS, decorin alone, or decorin+Nuc1 are shown on the left. The cryosections were stained with an antibody against activated Caspase-3 (red). The nuclei of corneal cells are stained with DAPI (blue). The bar graph on the right shows quantification of activated Caspase-3 staining in corneas from each of the 3 treatment groups: PBS, decorin alone, and decorin+Nuc1.

Nuc1 Decorin+Nuc1 Significantly Reduces Cell Death in the Cornea of Alkali Burn Mouse Model Caspase-3 mediated apoptosis has been shown to occur in the corneas of mice exposed to alkali burn. In order to determine whether decorin alone or decorin+Nuc1 have an effect on alkali burn induced cell death, transverse cryosections of the corneas of mice harvested at 7 days post treatment were stained for activated Caspase-3 (FIG. 18). There was no detectable activated Caspase-3 in the corneas of untreated control mice unexposed to alkali burn (FIG. 18). However, activated Caspase-3 staining was observed in all layers of the cornea (epithelium, stroma, and endothelium) of alkali burn exposed mice treated with PBS (FIG. 18). In mice exposed to alkali burn and treated by topical application of decorin alone, there was a considerable reduction in the staining for activated Caspase-3 in the stroma and endothelium of the corneas, with possible reduction in the epithelium, relative to corneas of PBS treated mice (FIG. 18). However, in corneas of mice exposed to alkali burn and treated topically with decorin+Nuc1, there was a significant reduction in activated Caspase-3 staining in all three layers of the cornea, including the epithelium, relative to PBS treated mice. Quantification of the fluorescent signal from activated Caspase-3 staining in corneas from each of the treatment and "no treatment" groups revealed a significant reduction in activated Caspase-3 staining in the corneas of mice treated with decorin alone (51.5%) or with decorin+ Nuc1 (74.6% p<0.0001, FIG. 18). There was also a significant reduction in the amount of activated Caspase-3 staining in corneas treated with decorin+Nuc1 relative to those treated with decorin alone (47.6%, p=0.0001)(FIG. 18).

Figure 19:
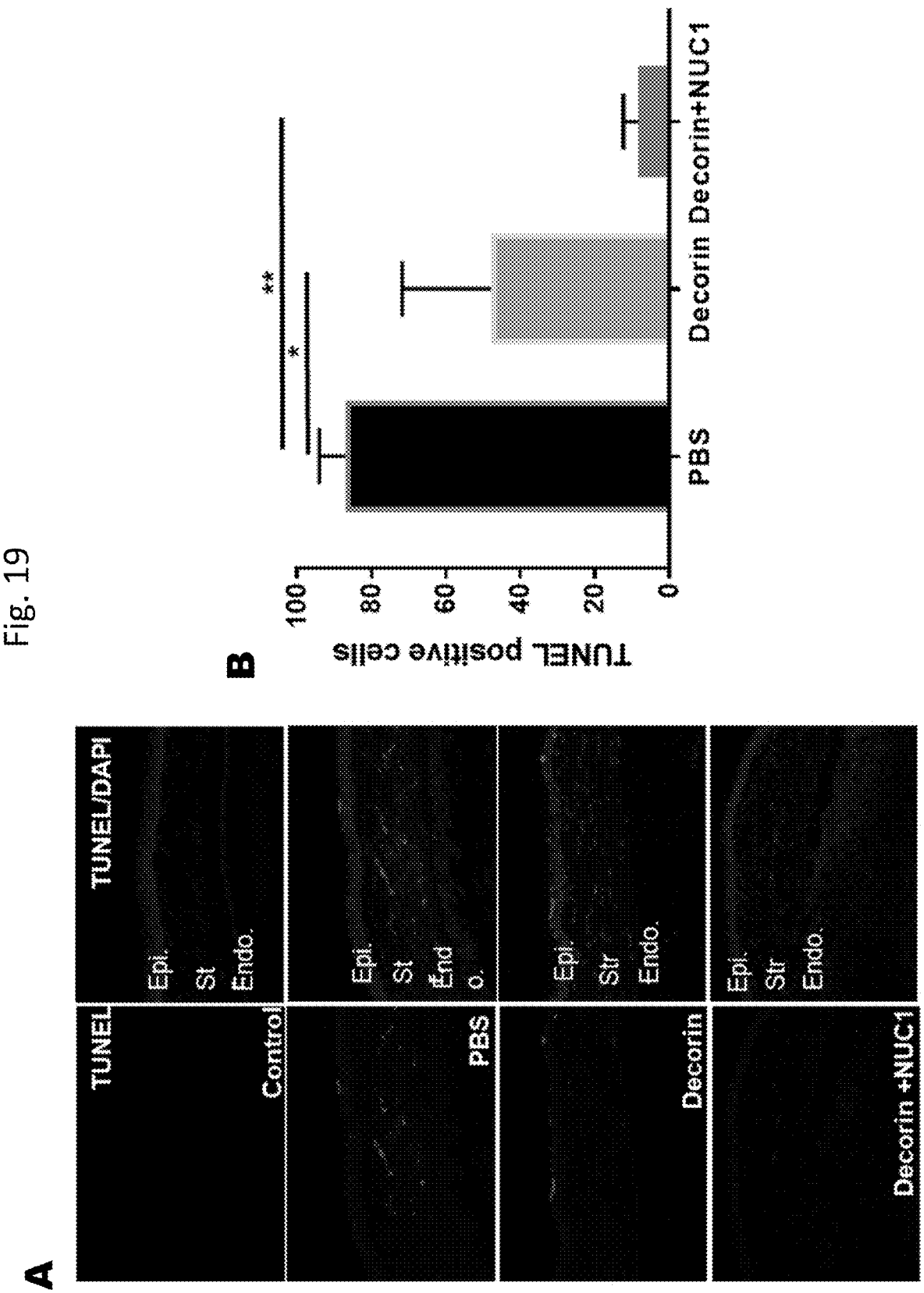
FIG. 19 shows that decorin+Nuc1 significantly reduces cell death in the cornea of mice exposed to alkali burn. (A) Representative images of cryosections of corneas of mice unexposed to alkali burn and treatment (Control) or exposed to alkali burn and one of the topical treatments: PBS, decorin alone, and decorin+Nuc1. The cryosections were stained by TUNEL assay (red). The nuclei of corneal cells are stained with DAPI (blue). For each of the treatments, an overlay of DAPI and TUNEL stain is shown in the left panel while TUNEL stain only is shown in the right panel. Epi, epthelium; Str, stroma; Endo, endothelium. (B) Bar graph quantifying TUNEL-positive cells in corneas from each of the 3 treatment groups: PBS, decorin alone, and decorin+Nuc1.

General cell death was also assessed in cryosections of cornea by TUNEL staining (FIG. 19A). There was little or no TUNEL staining observed in the untreated corneas of control mice unexposed to alkali burn (FIG. 19A). TUNEL staining, indicative of cell death, was observed in the stroma and epithelium of corneas of mice exposed to alkali burn and subsequently treated with PBS (FIG. 19A). There was a considerable reduction in TUNEL staining in the corneal stroma of mice exposed to alkali burn and treated with decorin alone (FIG. 19A), with little or no apparent reduction in TUNEL staining in the epithelium of these mice. In the corneas of mice exposed to alkali burn and treated with decorin+Nuc 1, there was little or no TUNEL staining in any of the corneal layers, suggesting almost complete protection against cell death in the corneas of these mice (FIG. 19B). Quantification of TUNEL staining in these corneas indicated a significant reduction in TUNEL staining in the corneas of mice exposed to alkali burn and treated with decorin alone (44.8%, p<0.0882) relative to those treated with PBS (FIG. 19B). A more substantial and significant reduction in TUNEL staining was observed, however, in corneas exposed to alkali burn and treated with decorin+Nuc1 (9045%, p<0.006), relative to those treated with PBS (FIG. 19B).

Figure 20:
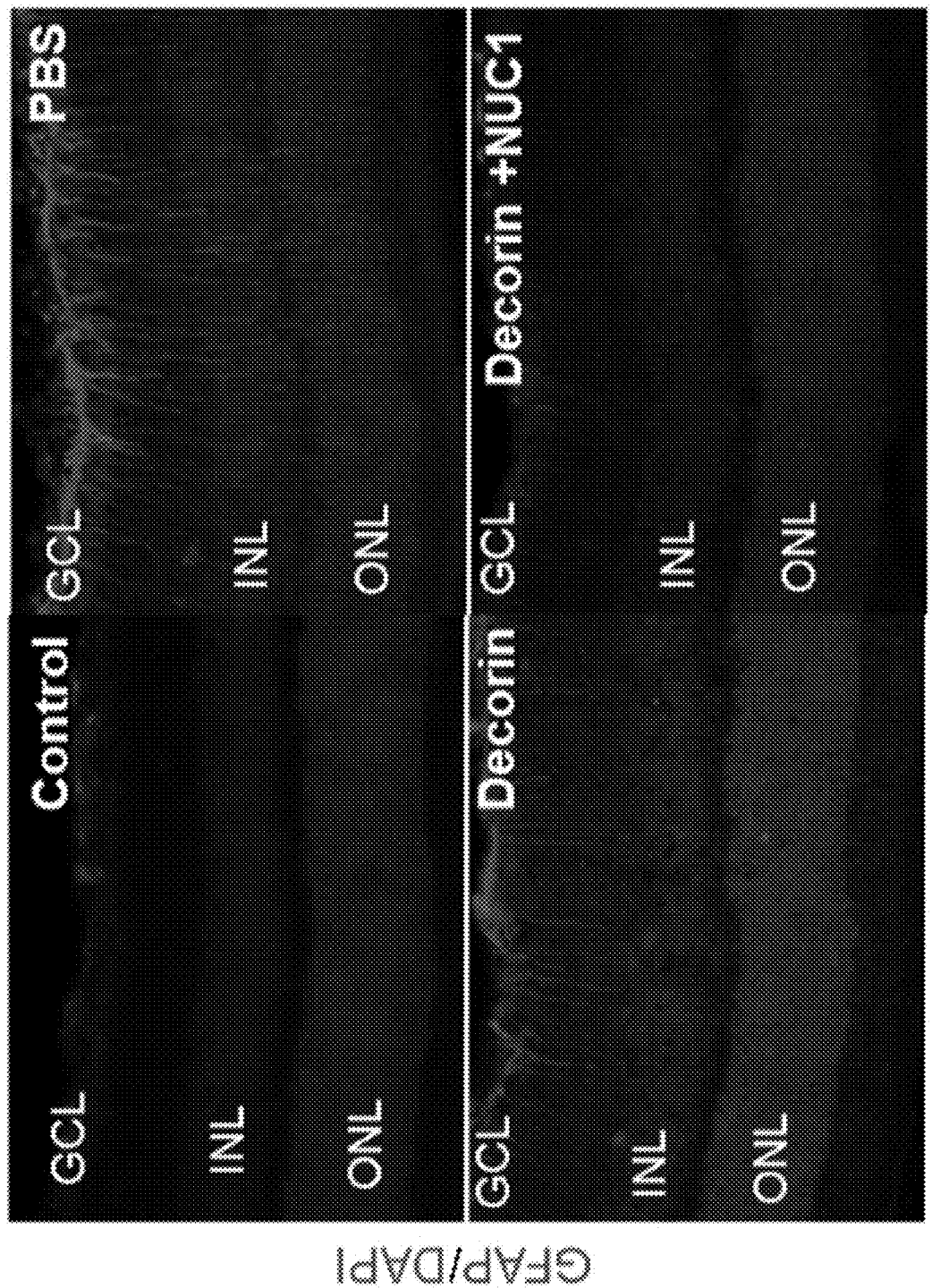
FIG. 20 shows that decorin+Nuc1 significantly reduces gliosis in the retina of mice exposed to alkali burn. Representative images of cryosections of retinas of mice unexposed to alkali burn and treatment (Control) or exposed to alkali burn and one of the topical treatments: PBS, decorin alone, or decorin+Nuc1 are shown. The cryosections were stained for glial fibrillary acidic protein (GFAP, red). The nuclei of retinal cells were stained with DAPI (blue). GCL, ganglion cell layer; INL/ONL, inner/outer nuclear cell layer.

Decorin+Nuc1 Significantly Reduces Gliosis in the Retina of Alkali Burn Mouse Model Gliosis, an activation of Muller glial cells in the retina, is a rapid stress response to alkali injury. An increase in the expression of glial fibrillary acidic protein (GFAP) is the hallmark of gliosis. Previous studies have shown that an increase in the proinflammatory cytokine TNF-A, in response to alkali burn, results in the induction of gliosis in the retina [22]. To determine whether topical treatment of the cornea of mice exposed to alkali burn with either decorin alone or decorin+Nuc1 results in protection of the retina against glial cell activation, we stained transverse cryosections of the retinas of mice subjected to alkali burn of the cornea for GFAP and treated them topically for 7 days with PBS, decorin alone, or decorin+Nuc1 (FIG. 20). Retinas of control mice, unexposed to alkali burn, were observed to have a pattern of GFAP staining consistent with a lack of activated of glial cells (FIG. 20). In the control retinas, GFAP was observed only in astrocytes and Muller cell end feet of the anterior retina. Retinas of mice exposed to alkali burn and treated with PBS were observed to have a pattern of GFAP staining consistent with activation of Muller glia (FIG. 20), with GFAP observed throughout the Muller cells, extending from the ganglion cell layer (GCL) through the inner nuclear layer and into the outer nuclear layer (INL/ONL). Retinas of mice exposed to alkali burn and treated with decorin alone also had a pattern of GFAP staining consistent with Muller cell activation, but with a reduced staining relative to the retinas of mice treated with PBS (FIG. 20). In these retinas, GFAP staining was observed to extend through the Muller cells from the GCL into the inner plexiform layer, but was not observed in the INL or ONL of these retinas. However, in retinas of mice exposed to alkali burn and treated with decorin+Nuc, GFAP staining was substantially reduced relative to the retinas of mice treated with decorin alone. In these retinas, the staining was mostly confined to the end feet of Muller cells in the GCL, with some occasional Muller cell staining in the inner plexiform layer (FIG. 20). These data suggest that both decorin alone and decorin+Nuc1 mediated a reduction in retinal gliosis in mice exposed to alkali burn. We could not, however, exclude the possibility of a direct effect of decorin alone and decorin+Nuc1 on the activation of retinal Muller cells.

Discussion

Increasing the retention and efficacy of drugs delivered to the eye is the key to increasing both bio-efficiency and therapeutic response to topical therapies. Due to the high turnover of the pre-corneal tear film, rapid elimination of aqueous drugs is a major challenge as it decreases the efficacy of drugs delivered to the cornea. Intensive topical routes of drug administration or invasive methods of drug delivery, including subconjunctival or intravitreal injections, are often associated with complications. In the instances where drugs are ineffective, surgery is often required to treat or remove the resulting corneal scar, increasing the risk of morbidity and the duration of patient discomfort subsequent to treatment.

Ocular burns are commonly associated with sight threatening complications and represent a clinical challenge for ophthalmologists. Current medical treatment aims to control inflammation by cautious use of corticosteroids or prophylactic antibiotics. The mouse model of alkali burn is well documented and provides a robust, clinically relevant means of evaluating the anti-scarring and anti-fibrotic effects of recombinant human decorin. Topical administration of the decorin protein, either with or without the cell penetrating peptide Nuc1, resulted in significantly reduced levels of corneal opacity after 7 days of topical treatments. Such reductions in corneal opacity could be of long-term benefit to patients, resulting in preservation of sight. Interestingly, we observed that the treatment not only prevented fibrosis but was also associated with a substantial reduction in inflammation and, thus, prevention of gliosis in the retina. Our results are consistent with previous studies, which indicate that production of the proinflammatory cytokine TNF-α by the cornea following alkali burn causes gliosis [22-24]. This reduction in inflammation is also beneficial in that it protects the epithelial and stromal layers of the cornea by inhibiting the activation of caspase-3 dependent apoptotic pathways. Topical administration of decorin was also able to regulate pathologies associated with alkali burn, likely due to its ability to penetrate the disrupted microenvironment of the damaged cornea. Furthermore, use of decorin in combination with Nuc1 resulted in a substantial decrease in haze, opacity, fibrosis and inflammation following alkali burn. Our results demonstrate that Nuc1 boosts the intrinsic ability of decorin protein to hasten the healing process, likely by improving its retention time and thereby increasing its therapeutic efficiency.

Alkali burn causes several disruptions of the corneal structure, including thinning of epithelial layers, stromal edema, and deposition of cellular infiltrates. Along with tear film and apical mucosa, the epithelium is a first line of defense for the eye. Topical administration of decorin with the peptide Nuc1 restored the epithelial morphology, and reduced stromal edema as well as the overall thickness of the cornea. Furthermore, previous studies have reported that decorin modulates several growth factors and signaling pathways (SMAD2 and SMAD3 via TGF-β) of corneal fibroblasts and thus attenuates scar formation in fibrosis. Since alkali burn injury is acute in nature, it is possible that endogenous decorin is not able to neutralize the hyperactive TGF-β molecule, thus allowing for activation of the downstream fibrotic cascade.

The massive inflammation of the anterior segment that results from alkali burns causes widespread damage to the inner and outer retina as well as the optic nerve. A recent report documented that alkali burn patients that underwent implantation of Boston keratoprosthesis exhibited an increase in intraocular pressure (i.e. glaucoma). There was an accelerated deterioration in the eyes of burn patients relative to non-burn implantation patients, despite aggressive therapeutic measures and surgery. The mechanism of damage to the retina after alkali burn has not been elucidated, though a few studies suggest the possibility of posterior alkali diffusion. There are also reports that suggest that the damage to the retina is due to the production of inflammatory cytokines, specifically TNF-α, and not simply diffusion [25]. Furthermore, proinflammatory cytokines, TNF-α and IL-1β, contribute to inflammation in several infectious and non-infectious ocular pathologies. IL-6 also plays an important role in corneal inflammatory disease, as IL-6R antagonists reduce corneal inflammation and neovascularization [25]. An increase in inflammation creates a feedback loop that causes further upregulation of pro-inflammatory genes [26]. The inflammatory environment disrupts the blood-retinal barrier and results in infiltration of immune cells from the blood, mainly neutrophils and macrophages [26]. These infiltrating immune cells activate the resident immune cells in the eye. Additionally, synaptic signaling from the Muller glia [27] triggers cytokine production in the retina, causing cellular stress in the anterior and posterior segments of the eye. Previous studies have reported apoptosis in the INL and ONL of mice and rabbit retinas due to an elevated pH in the anterior chamber, causing inflammation in uveitis [27, 28]. In our study, we observed robust gliosis in the retina and apoptosis in the cornea seven days after alkali burn, which was accompanied by increased levels of inflammatory cytokines TNF-α, IL-6 and IFN-G in the corneal lysates. Topical administration of decorin facilitated a reduction in inflammation and in turn, controlled gliosis and apoptosis. Although these results are encouraging, the multiple protective roles of decorin in treatment of alkali burn injury need further investigation.

In summary, although extensive preclinical safety studies are warranted, we have demonstrated that topical delivery of the anti-fibrotic protein decorin in conjunction with Nuc1 is likely safe and that Nuc1 can penetrate the inflamed cornea and deliver cargo proteins into corneal tissue. Decorin coupled with Nuc1 could efficiently rescue the corneal surface following alkali burn. Alkali burn falls in the category of severe ocular injuries and currently has very few treatment options. In our study, decorin retained its therapeutic potential and remained in contact with the surface of the eye long enough that it could significantly reduce corneal scarring. Thus, with the ability to combat ocular fibrosis, inflammation and cell death, topical application of decorin in combination with Nuc1 is a promising treatment for alkali burns.

Example 3

Nuc1 Enhances Retinal Delivery of Gene Editing Agents

To complement gene therapy and protein therapy, there is significant interest in the field of gene editing. One commonly used protein for gene editing is Cas9. In contrast to gene therapy, where long-term expression of a transgene is desirable, off-targeting effects can be avoided by transient expression of gene editing proteins such as Cas9. Furthermore, Cas9 and its functional relatives are bacterial proteins, and are thus immunogenic and toxic if expressed indefinitely in human cells. Gene therapy approaches in which transgene expression is regulated in vivo are complex. Thus, a more practical solution to the above issues is to transiently deliver gene editing proteins into the nucleus of cells. Once those exogenously delivered proteins have performed their function of gene-editing, they ought to be naturally degraded within the cell in a manner common to essentially all intracellular proteins. For this approach to succeed, it is essential to overcome cellular barriers to allow Cas9 to be delivered to target cells. We hypothesized that the CPP Nuc1 could be utilized for this purpose.

Nuc 1 Enhances Retinal Uptake of Cre Recombinase and Facilitates Gene Editing

Figure 21:
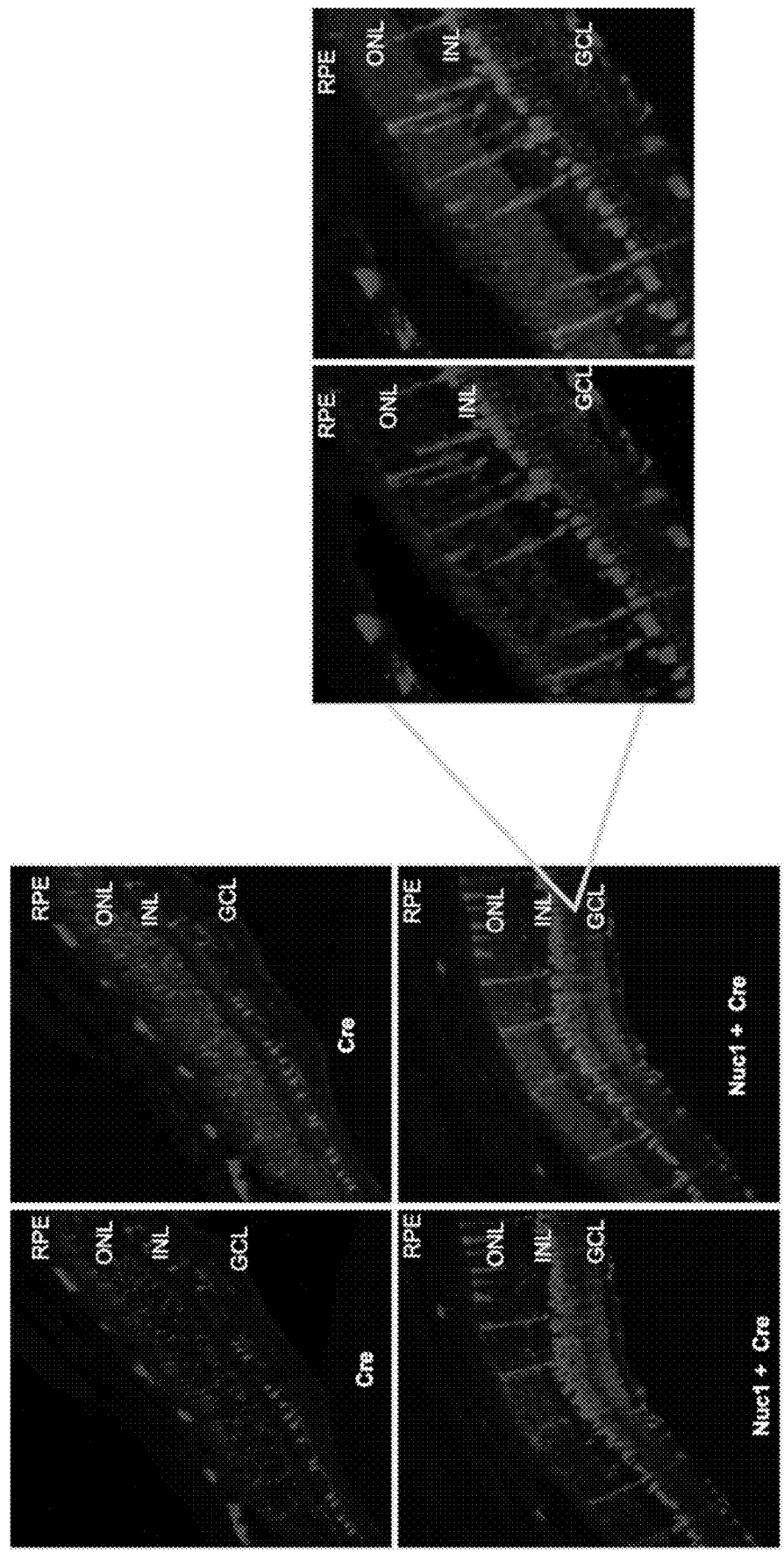
FIG. 21 shows representative confocal microscopy images of cryosections of retinas of Ai9 mice following intravitreal injection of 4 µg Cre recombinase with and without Nuc 1 (1 µg). Uptake, indicated by tdTomato expression from a reporter transgene (red), was observed in the ganglion cell layer (GCL), inner nuclear layer (INL), outer nuclear layer (ONL) and retinal pigment epithelium (RPE). Higher magnification images of a retina treated with Nuc1+Cre are shown on the right.

To test this hypothesis, we first investigated if Nuc1 could enable or enhance the uptake of Cre recombinase protein in Ai9 mice. In these mice, a reporter tdTomato transgene expression cassette is turned on when a foxed stop codon is excised by Cre recombinase. We injected adult (~6 week old) Ai9 mice intravitreally with 4 micrograms of Cre recombinase protein either by itself or in combination with 1 microgram of Nuc 1. We found that whereas there was detectable tdTomato expression in Ai9 mice injected with Cre recombinase alone, a significantly greater number and more types of cells were displayed reporter expression when Cre recombinase was co-injected with Nuc1. Specifically, there was a significantly greater number of Muller cells that were tdTomato positive when Cre recombinase was co-injected with Nuc1 (FIG. 21). Indeed, there were almost no Muller cells expressing tdTomato with Cre recombinase alone. Thus, our data demonstrate that Nuc1 enhances the uptake of exogenously delivered Cre recombinase, and that Nuc1-delivered Cre recombinase is functional in the nucleus. The observation that Cre recombinase can enter cells by itself was surprising. However, the above assay is highly sensitive due to the fact that one gene editing event is substantially amplified through the continuous production of protein that accumulates in the cell. Thus, the ability of Nuc1 to enhance the uptake of Cre recombinase is functionally consequential.

Nuc 1 Facilitates Retinal Uptake of Cas9 and Facilitates Gene Editing

Figure 22:
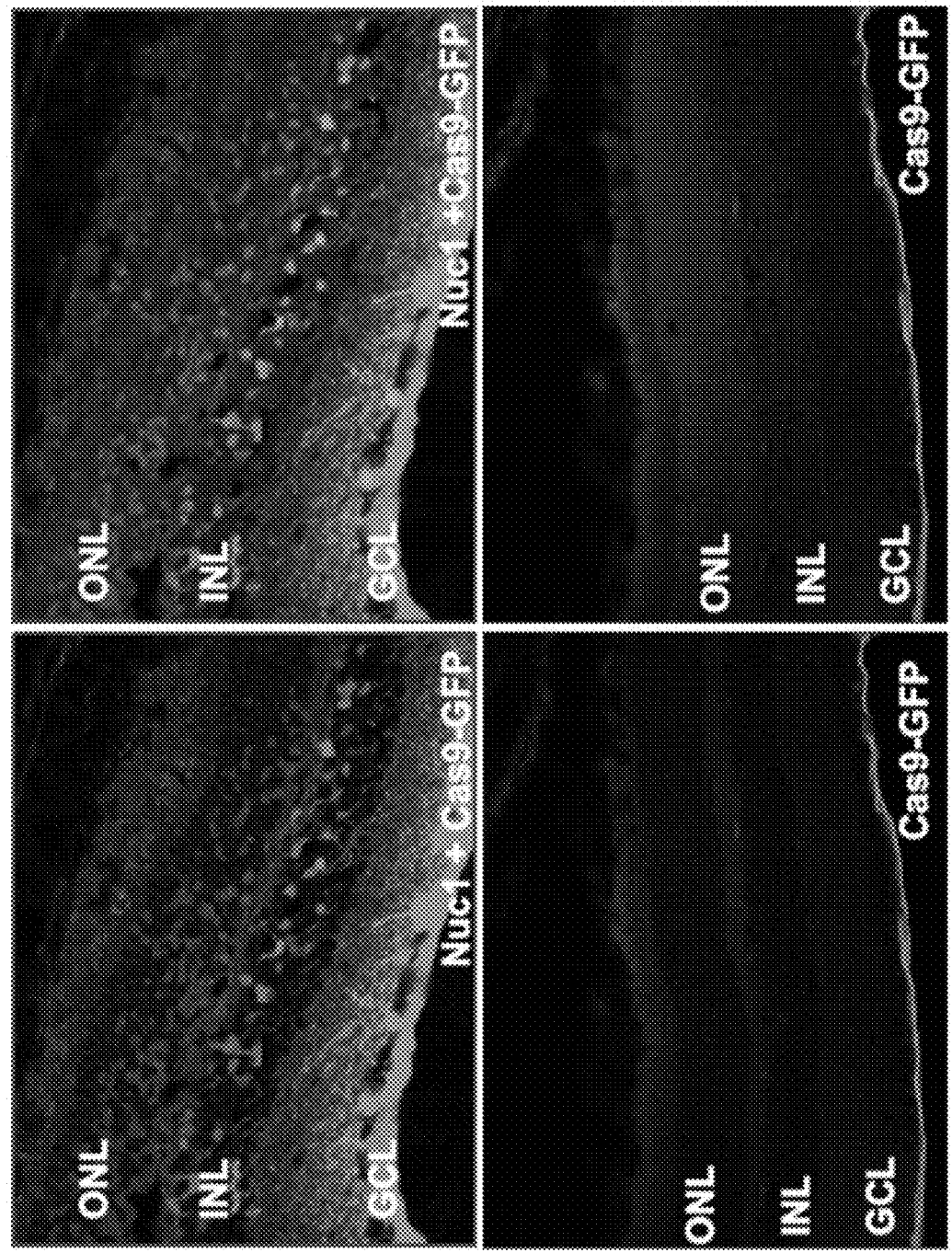
FIG. 22 shows representative confocal microscopy images of cryosections of retinas of C57BL/6J mice four hours post intravitreal injection with Cas9-GFP with and without Nuc1, GFP signal was observed in the ganglion cell layer (GCL), inner nuclear layer (INL), and outer nuclear layer (ONL).

Cre recombinase has a molecular weight of approximately 38 Kd and is substantially smaller than Cas9 which weighs approximately 160 Kd. To determine whether gene editing could be achieved with a significantly larger protein, we intravitreally injected a Cas9-GFP fusion protein into C57BL/6J mice. Cas9-GFP by itself failed to penetrate the retina and localized to the inner limiting membrane (FIG. 22). This indicates that whereas smaller proteins such as Cre recombinase can enter the retina on their own, larger, more therapeutically relevant Cas9-GFP proteins cannot. However, when co-injected with Nuc1 Cas9-GFP localized to various cell types in the retina including the outer nuclear layer (ONL), inner nuclear layer (INL), and ganglion cell layer (GCL) (FIG. 22).

Figure 23:
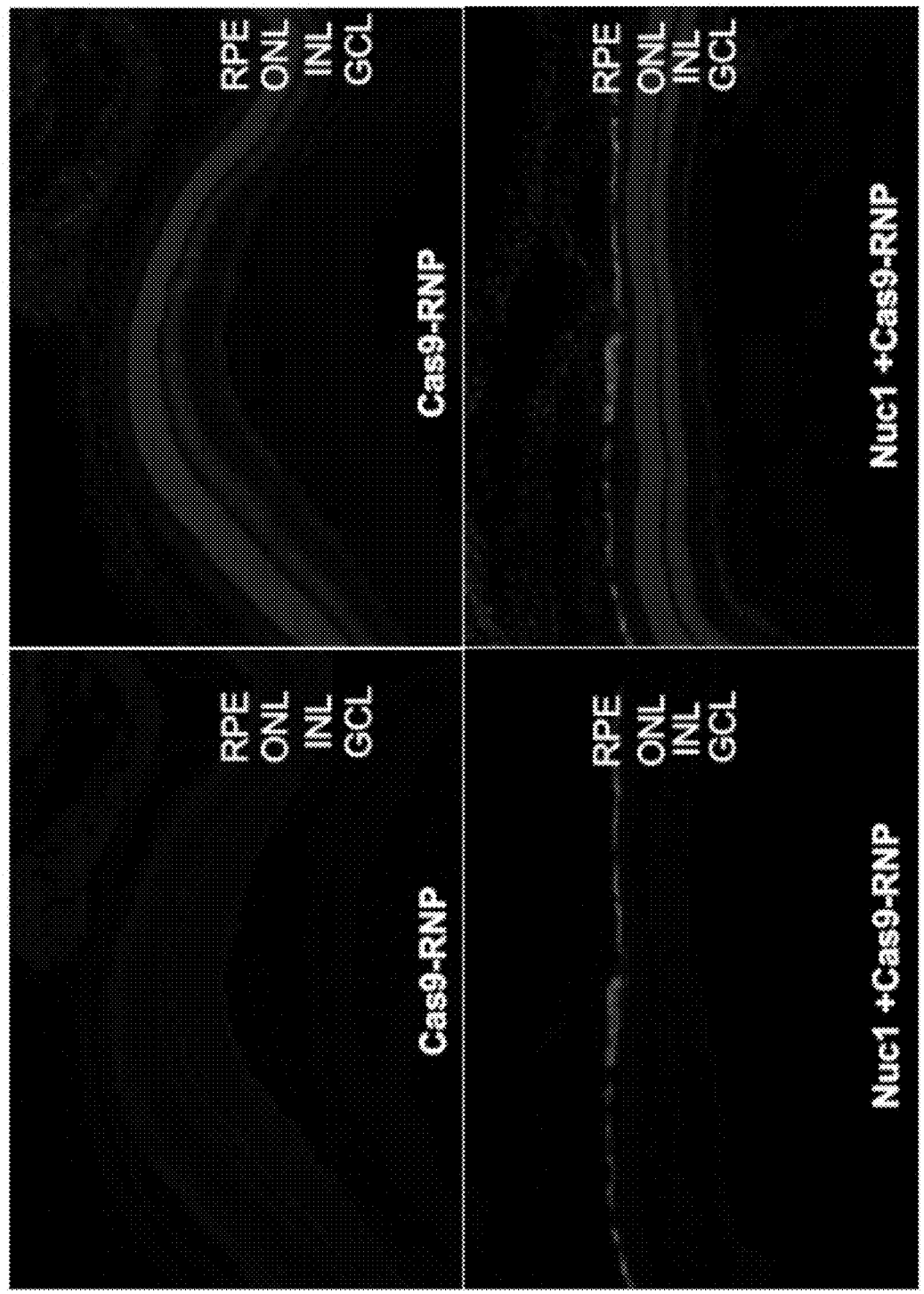
FIG. 23 shows representative confocal microscopy images of cryosections of retinas of Ai9 mice following subretinal injection of Cas9 coupled to ribonucleoprotein particles (Cas9-RNPs). Td-Tomato expression was localized in the retinal pigment epithelium (RPE) and few photoreceptors six weeks post injection. (A) 10× magnified images. (B) 40× magnified images.
Figure 23:
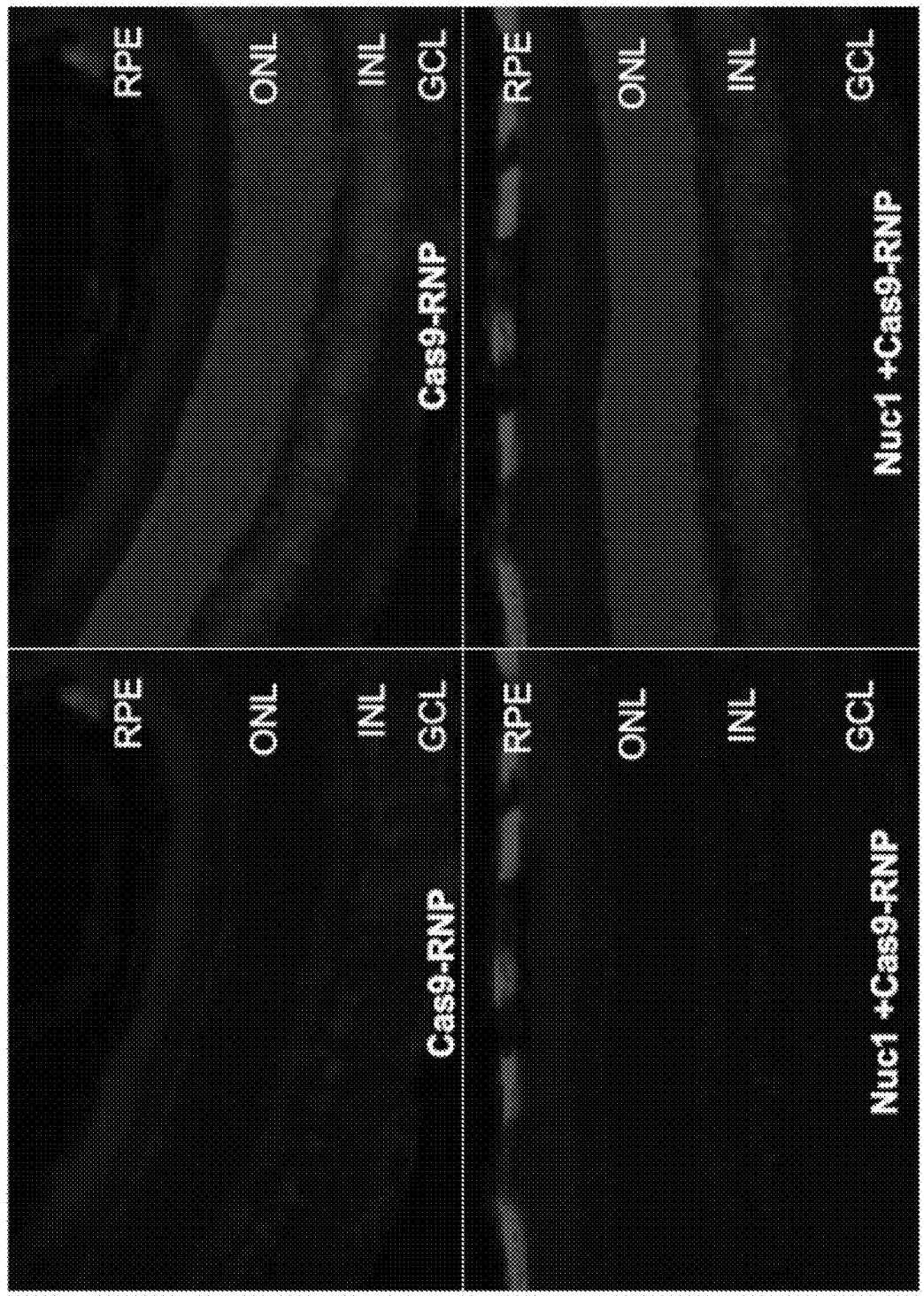
Figure 24:
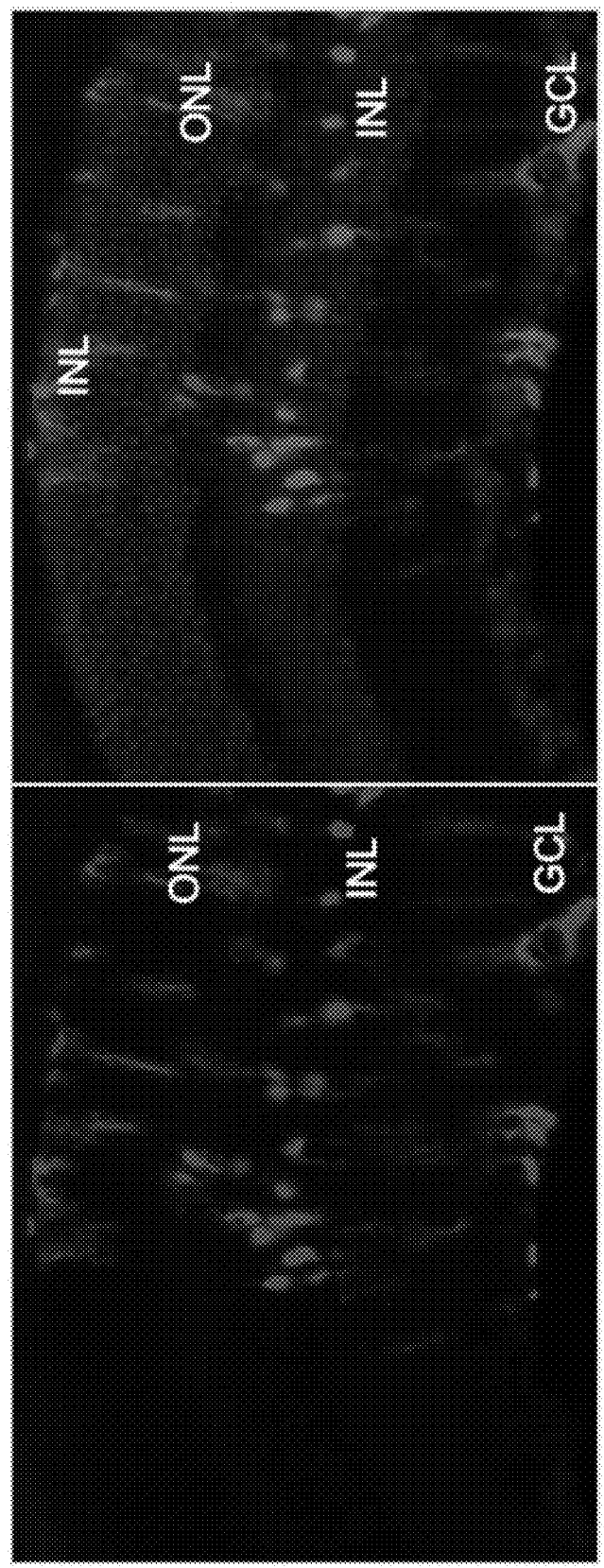
FIG. 24 shows representative confocal microscopy images of cryosections of retinas of Ai9 mice following intravitreal injection of Cas9 coupled to ribonucleoprotein particles (Cas9-RNPs). Td-Tomato expression was localized in the ganglion cell layer (GCL) and inner nuclear layer (INL).

Subsequently, we wished to address if Nuc1 could enhance the uptake of Cas9 coupled to ribonucleoprotein particles (RNPs) in the retina of Ai9 mice. Thus, we intravitreally or subretinally co-injected Nuc1 and Cas9 complexed with RNPs targeting the foxed stop codon in the tdTomato reporter described above. Following subretinal injection, there was significant expression of tdTomato in the retinal pigment epithelium (RPE, FIG. 23A-23B), indicating successful targeting of the RNPs. However, when Cas9-RNPs were injected without Nuc1, there was no expression of tdTomato, confirming that Nuc1 was necessary for efficient delivery of Cas9-RNPs in the retina. At higher concentrations, intravitreal injection of Nuc1 with Cas9-RNPs also turned on tdTomato expression in cells. With intravitreal injection, the cell types that exhibited reporter expression were variable in different parts of the retina, but included Muller cells and photoreceptors (FIG. 24).

REFERENCES

1. Griffith, G. L., et al., Treatment of corneal chemical alkali burns with a cross/inked thiolated hyaluronic acid film. Burns, 2018. 44(5): p. 1179-1186.
2. Clare, G., et al., Amniotic membrane transplantation for acute ocular burns. Cochrane Database Syst Rev, 2012(9): p. CD009379.
3. Behndig, A., et al., A case of unilateral acid burn. Acta Ophthalmol Scand, 2003. 81(5): p. 526-9.
4. Bron, A. J., The architecture of the corneal stroma. Br J Ophthalmol, 2001. 85(4): p. 379-81.
5. Strober, W., I. J. Fuss, and R. S. Blumberg, The immunology of mucosa! models of inflammation. Annu Rev lmmunol, 2002. 20: p. 495-549.
6. Fish, R. and R. S. Davidson, Management of ocular thermal and chemical injuries, including amniotic membrane therapy. Curr Opin Ophthalmol, 2010. 21(4): p. 317-21.
7. Tzeng, H. E., et al., lnterleukin-6 induces vascular endothelial growth factor expression and promotes angiogenesis through apoptosis signal-regulating kinase 1 in human osteosarcoma. Biochem Pharmacol, 2013. 85(4): p. 531-40.
8. Shin, Y. J., et al., Chemical injury-induced corneal opacity and neovascularization reduced by rapamycin via TGF-betal/ERK pathways regulation. Invest Ophthalmol Vis Sci, 2013. 54(7): p. 4452-8.
9. Dua, H. S., et al., Limbal epithelial crypts: a novel anatomical structure and a putative limbal stem cell niche. Br J Ophthalmol, 2005. 89(5): p. 529-32.
10. Gasymov, O. K., et al., Interaction of tear lipocalin with lysozyme and lactolerrin. Biochem Biophys Res Commun, 1999. 26 5(2): p. 322-5.
11. Glasgow, B. J., et al., Tear lipocalins: potential lipid scavengers for the corneal surface. Invest Ophthalmol Vis Sci, 1999. 40(13): p. 3100-7.
12. Mohan, R. R., et al., Decorin biology, expression, function and therapy in the cornea. Curr Mol Med, 2011. 11(2): p. 110-28.
13. Du, S., et al., Decorin inhibits angiogenic potential of choroid-retinal endothelial cells by downregulating hypoxia-induced Met, Racl, HIF-lalpha and VEGF expression in cocultured retinal pigment epithelial cells. Exp Eye Res, 2013. 116: p. 151-60.
14. Grant, D. S., et al., Decorin suppresses tumor cell-mediated angiogenesis. Onco gene, 2002. 21(31): p. 4765-77.
15. Mohan, R. R., et al., Targeted decorin gene therapy delivered with adeno-associated virus effectively retards corneal neovascularization in vivo. PLoS One, 2011. 6(10): p. e26432.
16. Iozzo, R. V., et al., Decorin antagonizes/GF receptor I (IGF-IR) function by interfering with IGF-IR activity and attenuating downstream signaling. J Biol Chem, 2011. 286(40): p.34712-21.
17. Bredrup, C., et al., Congenital stromal dystrophy of the cornea caused by a mutation in the decorin gene. Invest Ophthalmol Vis Sci, 2005. 46(2): p. 420-6.
18. Maidana, D. E., et al., A Novel lmageJ Macro for Automated Cell Death Quantitation in the Retina. Invest Ophthalmol Vis Sci, 2015. 56(11): p. 6701-8.
19. Anderson, C., Q. Zhou, and S. Wang, An alkali-bum injury model of corneal neovascularization in the mouse. J Vis Exp, 2014(86).
20. Chowdhury, S., et al., Pirfenidone nanoparticles improve corneal wound healing and prevent scarring following alkali burn. PLoS One, 2013. 8(8): p. e70528.
21. Chen, W. S., et al., Galectin-3 Inhibition by a Small-Molecule Inhibitor Reduces Both Pathological Corneal Neovascularizationand Fibrosis. Invest Ophthalmol Vis Sci, 2017. 58(1): p. 9-20.
22. Paschalis, E. I., et al., The Role of Microglia and Peripheral Monocytes in Retinal Damage after Corneal Chemical Injury. Am J Pathol, 2018. 188(7): p. 1580-1596.
23. Paranthan, R. R., et al., A robust model for simultaneously inducing corneal neovascularization and retinal gliosis in the mouse eye. Mal Vis, 2011. 17: p. 1901-8.
24. Zhou, C., et al., Sustained Subconjunctival Delivery of lnfliximab Protects the Cornea and Retina Following Alkali Burn to the Eye. Invest Ophthalmol Vis Sci, 2017. 58(1): p. 96-105.
25. Chen, Y., et al., MK2 inhibitor reduces alkali bum-induced inflammation in rat cornea. Sci Rep, 2016. 6: p.28145.
26. Ogura, S., et al., Sustained inflammation after pericyte depletion induces irreversible blood-retina barrier breakdown. JCI Insight, 2017. 2(3): p. e90905.
27. Wizeman, J. W. and R. Mohan, Expression of peptidyiarginine deiminase 4 in an alkali injury model of retinal gliosis. Biochem Biophys Res Commun, 2017. 487(1): p. 134-139.
28. Kumar, B., S. M. Cashman, and R. Kumar-Singh, Complement-Mediated Activation of the NLRP3 Jnflammasome and Its Inhibition by AAV-Mediated Delivery of CD59 in a Model of Uveitis. Mol Ther, 2018. 26(6): p. 1568-1580.

I claim:

1. A peptide comprising:
   an amino acid sequence having at least 90% sequence identity to SEQ ID NO: 3.
2. The peptide of claim 1, wherein the peptide comprises SEQ ID NO: 3.
3. A pharmaceutical composition comprising the peptide of claim 1 and an agent.
4. The pharmaceutical composition of claim 3, wherein the agent is selected from the group consisting of a peptide, recombinant protein, antibody, proteoglycan, steroid, virus, nucleic acid, ribonucleoprotein, small molecule therapeutic agent, and detectable label.
5. The pharmaceutical composition of claim 3, wherein the agent is a gene therapy or gene editing agent.
6. A method for delivering an agent to a cell or a tissue of a subject, the method comprising contacting the cell or the tissue with the composition of claim 3, wherein the agent is delivered to the cell or the cells of the tissue.
7. The method of claim 6, wherein the peptide is not conjugated or physically linked to the agent.
8. The method of claim 6, wherein the subject has an ocular degenerative disease or an eye injury.
9. The method of claim 6, wherein the cell or the tissue is selected from the group consisting of ocular, photoreceptors, retinal pigment epithelium, ganglion cells, bipolar cells, Muller cells, choroidal endothelial cells, lens epithelium, corneal endothelium, corneal stroma, trabecular meshwork, and iris.
10. The method of claim 9, wherein the ocular cell or the ocular tissue is retinal or corneal.
11. The method of claim 6, wherein the peptide increases the delivery of the agent to the cell or the cells of the tissue as compared to the agent alone.
12. A polynucleotide encoding the peptide of claim 1.
13. The polynucleotide of claim 12, wherein the polynucleotide is inserted within a sequence encoding a viral capsid protein.
14. A nucleic acid construct comprising the polynucleotide of claim 12, wherein the polynucleotide is operably connected to a promoter.
15. A method of delivery to a cell or tissue comprising contacting the cell with the peptide of claim 1, wherein the peptide is a cell penetrating peptide and the peptide enters the cell.
16. The method of claim 15, further comprising contacting the cell or the tissue with an agent, wherein the peptide increases delivery of the agent to the cell or the tissue or allows for transduction of the agent into the cell or the tissue as compared to delivery into the cell in the absence of the peptide.
17. A virus comprising a modified viral capsid protein, wherein the modified viral capsid protein comprises a peptide consisting of (a) SEQ ID NO: 6 or (b) an amino acid sequence having at least 90% sequence identity to SEQ ID NO: 6.
18. The virus of claim 17, wherein the peptide consists of SEQ ID NO: 6.
19. The virus of claim 17, wherein the virus is adeno-associated virus (AAV).
20. The virus of claim 19, wherein the AAV is AAV9.
21. The virus of claim 17, further comprising a polynucleotide encoding a polypeptide agent.
22. The virus of claim 21, wherein the polypeptide agent is selected from the group consisting of decorin and NRF2.
23. A method for delivering an agent to a cell or a tissue of a subject, the method comprising contacting the cell or the tissue with the virus of claim 21, wherein the agent is transduced into the cell or the cells of the tissue.
24. A method for delivering a virus to a cell or a tissue, the method comprising contacting the cell or the tissue with the virus of claim 17, wherein the virus is delivered to or transduced into the cell or the tissue at an increased rate as compared to a cell or a tissue contacted with a virus that does not express the modified viral capsid protein.
25. The method of claim 24, further comprising contacting the cell or tissue with a peptide comprising:
   (a) a first portion consisting of SEQ ID NO: 4 linked via a flexible linker to a second portion consisting of SEQ ID NO: 5, or
   (b) an amino acid sequence having at least 90% sequence identity to SEQ ID NO: 3.

* * * * *

SEQUENCE LISTING

<160> NUMBER OF SEQ ID NOS: 8

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide- Generalized Nuc1 peptide
      with variable linker

```
<220> FEATURE:
<221> NAME/KEY: MISC_FEATURE
<222> LOCATION: (10)..(11)
<223> OTHER INFORMATION: Xaa is any amino acid

<400> SEQUENCE: 1

Ala Ser Ile Lys Val Ala Val Ser Ala Xaa Xaa Asp Lys Pro Arg Arg
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide- Generalized IKV peptide
      flanked by variable linkers
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid

<400> SEQUENCE: 2

Xaa Ala Ser Ile Lys Val Ala Val Ser Ala Xaa
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide- Nuc1 peptide

<400> SEQUENCE: 3

Ala Ser Ile Lys Val Ala Val Ser Ala Gly Gly Asp Lys Pro Arg Arg
1               5                   10                  15

<210> SEQ ID NO 4
<211> LENGTH: 9
<212> TYPE: PRT
<213> ORGANISM: Homo sapiens

<400> SEQUENCE: 4

Ala Ser Ile Lys Val Ala Val Ser Ala
1               5

<210> SEQ ID NO 5
<211> LENGTH: 5
<212> TYPE: PRT
<213> ORGANISM: Homo sapiens

<400> SEQUENCE: 5

Asp Lys Pro Arg Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide- Partial sequence from
      laminin-1 flanked by glycine linkers

<400> SEQUENCE: 6

Gly Ala Ser Ile Lys Val Ala Val Ser Ala Gly
```

-continued

```
<210> SEQ ID NO 7
<211> LENGTH: 6
<212> TYPE: PRT
<213> ORGANISM: Homo sapiens

<400> SEQUENCE: 7

Cys Asp Lys Pro Arg Arg
1               5

<210> SEQ ID NO 8
<211> LENGTH: 19
<212> TYPE: PRT
<213> ORGANISM: Homo sapiens

<400> SEQUENCE: 8

Cys Ser Arg Ala Arg Lys Gln Ala Ala Ser Ile Lys Val Ala Val Ser
1               5                   10                  15

Ala Asp Arg
```